US 11,648,277 B2

(12) United States Patent
Wang et al.

(10) Patent No.: US 11,648,277 B2
(45) Date of Patent: May 16, 2023

(54) COMBINATION THERAPY WITH GOLD CONTROLLED TRANSGENES

(71) Applicant: Chimera Bioengineering, Inc., Pacifica, CA (US)

(72) Inventors: Benjamin Wang, Menlo Park, CA (US); Scott Dylla, Portola Valley, CA (US); Gusti Zeiner, Pacifica, CA (US)

(73) Assignee: Chimera Bioengineering, Inc., Pacifica, CA (US)

( * ) Notice: Subject to any disclaimer, the term of this patent is extended or adjusted under 35 U.S.C. 154(b) by 0 days.

(21) Appl. No.: 17/718,095

(22) Filed: Apr. 11, 2022

(65) Prior Publication Data

US 2022/0257658 A1 Aug. 18, 2022

Related U.S. Application Data

(63) Continuation of application No. 16/993,782, filed on Aug. 14, 2020.

(60) Provisional application No. 62/965,569, filed on Jan. 24, 2020, provisional application No. 63/054,721, filed on Jul. 21, 2020, provisional application No. 62/888,524, filed on Aug. 18, 2019.

(51) Int. Cl.
*A61K 35/17* (2015.01)
*C07K 14/715* (2006.01)
*A61P 35/00* (2006.01)
*C07K 14/705* (2006.01)

(52) U.S. Cl.
CPC ............. *A61K 35/17* (2013.01); *A61P 35/00* (2018.01); *C07K 14/70578* (2013.01); *C07K 14/7155* (2013.01); *C07K 14/7156* (2013.01)

(58) Field of Classification Search
CPC ..................................................... A61K 35/17
See application file for complete search history.

(56) References Cited

U.S. PATENT DOCUMENTS

| | | | |
|---|---|---|---|
| 2009/0048191 | A1 | 2/2009 | Rakoczy et al. |
| 2010/0316609 | A1 | 12/2010 | Dewhurst |
| 2011/0003385 | A1 | 1/2011 | Crabtree |
| 2013/0245096 | A1 | 9/2013 | Abitbol |
| 2014/0120622 | A1 | 5/2014 | Gregory et al. |
| 2014/0242701 | A1 | 8/2014 | Shiku et al. |
| 2014/0271583 | A1 | 9/2014 | Allen-Hoffmann et al. |
| 2014/0286987 | A1 | 9/2014 | Spencer et al. |
| 2014/0349402 | A1 | 11/2014 | Cooper et al. |
| 2015/0307564 | A1 | 10/2015 | Young et al. |
| 2016/0040126 | A1 | 2/2016 | Baik et al. |
| 2018/0044424 | A1 | 2/2018 | June et al. |
| 2018/0057822 | A1* | 3/2018 | Wang .................. C12Q 1/6897 |
| 2018/0273618 | A1 | 9/2018 | Murriel et al. |
| 2019/0270817 | A1 | 9/2019 | Ali et al. |
| 2019/0365810 | A1 | 12/2019 | Wang et al. |
| 2019/0367612 | A1 | 12/2019 | Chaen et al. |
| 2020/0289565 | A1 | 9/2020 | Green et al. |

FOREIGN PATENT DOCUMENTS

| | | |
|---|---|---|
| WO | WO 2015092440 | 6/2015 |
| WO | WO 2015123527 | 8/2015 |
| WO | WO 2015123642 | 8/2015 |
| WO | WO 2015140268 | 9/2015 |
| WO | WO 2015142661 | 9/2015 |
| WO | WO 2015142675 | 9/2015 |
| WO | WO 2015193406 | 12/2015 |
| WO | WO 2016028896 | 2/2016 |
| WO | WO 2016126608 | 8/2016 |
| WO | WO 2016/149254 | 9/2016 |
| WO | WO 2017/149515 | 9/2017 |

OTHER PUBLICATIONS

Posey et al., 2016, Immunity 44, 1444-1454 (Year: 2016).*
Koneru et al. Journal of Translational Medicine (2015) 13:102, pp. 1-11. DOI 10.1186/s12967-015-0460-x (Year: 2015).*
Auslander et al, A ligand-dependent hammerhead ribozyme switch for controlling mammalian gene expression, 2010, Molc Biosys vol. 6, pp. 807-814.
Budde et al., Combining a CD20 chimeric antigen receptor and an inducible caspase 9 suicide switch to improve the effriciacy amd safety of . . . , 2013, PLoS ONE vol. 8, pp. 1-10.
Cooper et al, T-cell immunotherapies for treating breast cancer, 2011, URL:http://www.dtic.mil/dtic/tr/fulltext/u2/a55488253.pdf.
Grada et al, TanCAR: a novel bispecific chimeric antigen receptor for cancer immunotherapy, 2013, Mole Therapy—Nucl Acids vol. 2, pp. e105.
Iwamoto et al, A general chemical method to regulate protein stability in the mammalian central nervous system, Chem Biol vol. 17, pp. 981-988.
Liu et al, Genetically modified adenoviral vector with the protein transduction domain of Tat improves transfer to CAR-deficient cells, 2009, Biosc Rep vol. 29, p. 103.
Win et al, A modular and extensible RNA-based gene-regulatory platform for engineering cellular function, 2007, Proc Natl Acad Sci vol. 104, pp. 14283-14288.
White et al., A dimer interface mutation in glyceraldehyde-3-phosphate dehydrigenase regulates its binding to AU-rich RNA, 2015, J. Biol. Chem. vol. 290, pp. 1770-1785.

(Continued)

*Primary Examiner* — Scott Long
(74) *Attorney, Agent, or Firm* — HelixIP LLP

(57) ABSTRACT

Control Devices are disclosed including RNA destabilizing elements (RDE) combined with transgenes, including Chimeric Antigen Receptors (CARs) in eukaryotic cells. These RDEs can be used to optimize expression of transgenes, e.g., CARs, in the eukaryotic cells so that, for example, effector function is optimized. CARs and transgene payloads can also be engineered into eukaryotic cells so that the transgene payload is expressed and delivered at desired times from the eukaryotic cell. Such CAR T-cells with transgene payloads can be combined with the administration of other molecules, e.g., other therapeutics such as anticancer therapies.

20 Claims, 11 Drawing Sheets

Specification includes a Sequence Listing.

(56) References Cited

OTHER PUBLICATIONS

Anonymous, Treatment of relapsed and/or chemotherapy refractory advanced malignancies by CART133, 2015, ClinicalTrials.gov.
Feng et al, Theophylline-dependent aptazyme as a novel tool for transgene expression regulation in mammalian cells, 2015, Molc Therap vol. 23, pp. s66.
Jensen et al, Design and implementation of adoptive therapy with chimeric antigen receptor-modified T cells, 2013, Immunol Rev vol. 257, pp. 127-144.
Kenderian et al, CD33-specific chimeric antigen receptor T cells exhibit potent preclinical activity against human acute myeoloid . . . , 2015, Blood Cancer J vol. 29, pp. 1637-1647.
Mardiros et al, T cells expression CD123-specific chimeric antigen receptors edhibit specific cytolytic effector functions and antitumor . . . , 2013, Blood vol. 122, pp. 3138-3148.
Walter et al, Acute myeloid leukemia stem cells and CD33-targeted immunotherapy, 2012, Blood vol. 119, pp. 6198-6208.
Peng et al, Ectodomain shedding of Fcα receptor is mediated by ADAM10 and ADAM17, 2010, Immunology vol. 130, pp. 83-91.
Zhou et al, Codon usage is an important determinant of gene expression levels largely through effects on transcription, 2016, Proc Natl Acad Sci vol. 113, pp. E6117-E6125.
Christopherson et al., Classfication of AML using a monoclonal antibody microarray, 2006, Meth in Mocl Med vol. 125, pp. 241-251.
Kloss et al, Combinatorial antigen recognition with balanced signalling promotes selective tumor eradication . . . , 2013, Nat Biotechnol vol. 31, pp. 71-75.
Kondo et al., Binding of glyceraldehyde-3-phoisphate dehydrogenase to the cis-acting element of structure-anchored . . . , 2011, Biochem Biophys Res Comm vol. 405, pp. 382-387.
Palmer et al, Glucose metabolism regulates T cell activation, differentiation, and functions, 2015, Frontiers Immunol vol. 5, pp. 1-6.
Aldape et al., Glioblastoma: pathology, molecular mechanisms and markers, Acta Neuropathol., 2015, vol. 129, pp. 829-848.
Chester et al., 4-1BB agonism: adding the acelerator to cancer immunotherapy, 2016, Cancer Immunol Immunother vol. 65, pp. 1243-1248.
Garrett, Using patient-derived gliomaspheres to moleculary charaterize and dissect distinctive . . . , 2016, UCLA Electronic Theses and Dissertations.
Kovarik et al, Posttranscriptional regulation of cytokine expression, 2017, Cytokine vol. 89, pp. 21-26.
Mardiana et al., A multifunctional role for adjuvant anti-4-1BB therapy in augmenting antitumor responses by CAR T cells, 2018, AACR Ann Mtg Abst 1530.
Rodriguez et al., Chimeric antigen receptor T-cell therpy for glioblastoma, 2017, Translational Res Sep. 2017, pp. 93-102.
Wang et al, Metabolic checkpoints in activated T cells, 2012, Nature Immunol. vol. 13, pp. 907-915.
Wieten et al, A novel heat shock protein coinducer boosts stress protein Hsp70 to activate T cell regulation of inflammation . . . , 2010, Arth Rheum vol. 62, pp. 1026-1035.
Iwamoto et al., A general chemical method to regulate protein stability in the mammalian nervous system, 2010, Chem & Biol vol. 17, pp. 981-988.
Rakhit et al, Evaluation of FKBP and DHFR based destabilizing domains in *Saccharomyces cerivisiae*, 2011, Bioorg & Med Chem Lett vol. 21, pp. 4965-4968.
Jena et al., Redirecting T-cell specificity by introducing a tumor-specific chimeric antigen receptor, 2010, Blood vol. 116, pp. 1035-1044.
Nielsen et al., Split-receptors in the tachykinin neurokinin-1 system, 1998, Eur. J. Biochem. vol. 251, pp. 217-226.
Adusumilli et al., Regional Delivery of Mesothelin-Targeted CAR T-cell Therapy Generates Potent . . . Tumor Immunity, Nov. 2014, Sci. Transl. Med. 6:261ra151.
Aranda et al., Adoptive Cell Transfer for Anticancer Immunotherapy, Apr. 2015, OncoImmunol. 3:5, e28344.
Auslander, et al., From Gene Switches to Mammalian Designer Cells: Present and Future Prospects, Mar. 2013, Trends Biotechnol. 31:155-168.
Baker et al., Structural and Dynamic Control of T-cell Receptor Specificity, Cross-Reactivity, and Binding Mechanism, 2012, Immunol. Rev. 250:10-31.
Beilstein, et al., Conditional Control of Mammalian Gene Expression by Tetracycline-Dependent Hammerhead Ribozymes, Sep. 2014, Synth. Biol. 4:526-534.
Berens, et al., RNA Aptamers as Genetic Control Devices: The Potential of Riboswitches as Synthetic Elements for Regulating Gene Expression, 2015, Biotechnol. 10:246-257.
Bonifant, et al., Toxicity and Management in CAR T-cell Therapy, 2016, Oncolytics 3:16011.
Bray, et al., On-Site CAR Parking, 2015, Sci. Transl. Med. 7:275ra22.
Brayer et al., Developing Strategies in the Immunotherapy of Leukemias, Jan. 2013, Cancer Control 20:49-59.
Brentjens, et al., Adoptive Therapy of Cancer with T cells Genetically Targeted to Tumor Associated Antigens Through . . . , May 2011, Am Soc Gene Cell Therap., presentation.
Brudno et al., Allogenic T Cells That Express and Anti-CD19 Chimeric Antigen Receptor Induce Remissions of B-cell . . . , 2016, Am Soc Clin Oncol 34.
Buckley et al., Update on Antigen-Specific Immunotherapy of Acute Myeloid Leukemia, 2015, Curr. Hematol. Malig. Rep. 10:65-75.
Budde et al., Combining a CD20 Chimeric Antigen Receptor and an Inducible Caspace 9 Suicide Switch to Improve the Efficacy . . . , Dec. 2013, PLoS ONE 8:e82742.
Cantelmo, et al., Inhibition of the Glycolytic Activator PFKFB3 in Endothelium Induces Tumor Vessel Normalization . . . , Dec. 2016, Cancer Cell 30:968-985.
Caruso et al., Tuning Sensitivity of CAR to EGFR Density Limits Recognition of Normal Tissue While Maintaining . . . , 2015, Cancer Res. 75:3505-3518.
Chakravarti et al., Synthetic Biology in Cell-Based Cancer Immunotherapy, 2015, Trends Biotechnol. 33:449-461.
Chang et al., Posttranscriptional Control of T Cell Effector Function by Aerobic Glycolysis, Jun. 2013, Cell 153:1239-1251.
Chang et al., Identification and Selective Expansion of Functionally Superior T cells Expressing Chimeric Antigen Receptors, 2015, J. Transl. Med. 13:161.
Cheadle et al., CAR T cells: Driving the Road from the Laboratory to the Clinic, 2013, Immunol. Rev. 257:91-106.
Chen et al., Genetic Control of Mammalian T-cell Proliferation with Synthetic RNA Regulatory Systems, 2010, Proc. Natl Acad. Sci. 107:8531-8536.
Chen et al., Efficient Gene Editing in Primary Human T cells, Nov. 2015, Trends Immunol. 36:667-669.
Cooper et al., Moving from Tinkering in the Garage to Assembly Line Production: the Manufacture of Genetically Modified T cells . . . , 2015, Cancer Gene Therap. 22:64-66.
Darcy et al., Adoptive Immnotherapy: a New Era for the Treatment of Cancer, 2015, Immunotherap. 7:469-471.
Davila et al., Efficacy and Toxicity Management of 19-28z CAR T cell Therapy in B cell Acute Lymphoblastic Leukemia, Feb. 2014, Sci Transl Med 6:224ra25.
Di Stasi et al., Inducible Apoptosis as a Safety Switch for Adoptive Cell Therapy, 2011, N. Engl. J. Med. 265:1673-83.
Dotti et al., Design and Development of Therapies Using Chimeric Antigen Receptor-Expressing T cells, Jan. 2014, Immunol. Rev. 257:107-126.
Elert et al., Calling Cells to Arms, Dec. 2013, Nature 504:S2-S3.
Elfakess et al., Unique Translation Initiation of mRNAs-Containing TISU Element, Jun. 2011, Nucl. Acids. Res. 39:7598-7609.
Ellebrecht et al., Reengineering Chimeric Antigen Receptor T cells for Targeted Therapy of Autoimmune Disease, Jul. 2016, Science 353:179-184.
Farajnia et al., Development Trends for Generation of Single-Chain Antibody Fragments, Aug. 2014, Immunopharmacol. Immunotoxicol. 36:297-308.

(56) References Cited

OTHER PUBLICATIONS

Federov et al., PD-1 and CTLA-4 Based Inhibitory Chimeric Antigen Receptors (iCARs) Divert Off-Target Immunotherapy . . . , Dec. 2013, Sci. Transl. Med. 5:215ra172.
Festuccia et al., Allogenic Stem Cell Transplantation in Multiple Myeloma: Immunotherapy and New Drugs, Jun. 2015, Expert Opin. Biol. Therapy 15:857-872.
Garber et al., Adoptive T-cell Therapy for Leukemia, 2014, Molc. Cell. Therap. 2:25-.
Garcia-Sanz et al., Translational Control: a General Mechanism for Gene Regulation During T cell Activation, 1998, FASEB J. 12:299-306.
Ghorashian et al., CD19 Chimeric Antigen Receptor T cell Therapy for Haematological Malignancies, Mar. 2015, Brit, J. Haematol. 169:463-478.
Grada et al., TanCAR: A Novel Bispecific Chimeric Antigen Receptor for Cancer Immunotherapy, 2013, Molc. Therap. Nucl. Acids 2:e105.
Hamilton et al., Delineation of a Novel Pathway that Regulates CD154 (CD40 Ligand) Expression, 2003, Molc. Cell. Biol. 23:510-525.
Hjelm et al., Mifepristone-Inducible Transgene Expression in Neural Progenitor Cells in vitro and in vivo, 2016, Gene Therap. 23:424-437.
Horton et al., Recent Advances in Acute Myeloid Leukemia Stem Cell Biology, 2012, Haematolog. 97:966-974.
Huang et al., Driving an Improved CAR for Cancer Immunotherpy, 2016, J. Clin. Invest. 126:2795-2798.
Hudecek et al., The Nonsignaling Extracellular Spacer Domain of Chimeric Antigen Receptors is Decisive for In Vivo . . . , Sep. 2014, Cancer Immunol. Res. 3:125-135.
Hurton et al., Tethered IL-15 Augments Antitumor Activity and Promotes a Stem-Cell Memory Subset in Tumor-Specific T cells, Nov. 2016, Proc. Natl Acad Sci 113:E7788-E7797.
Hussaini et al., Targeting CD123 in AML Using a T-cell Directed Dual-Affinity Re-Targeting (DART) Platform, Nov. 2015, Blood 127:122-131.
Iwamoto et al., A General Chemical Method to Regulate Protein Stability in the Mammalian Central Nervous System, 2010, Chem Biol 17:981-988.
Jensen et al., Enhancing the IQ of CAR Modified T Cells, 2015, Powerpoint Slides.
Jensen et al., Mathematical Modeling of Chimeric TCR Triggering Predicts the Magnitude of target Lysis and its Impairment by TCR . . . , 2010, J. Immunol. 184:4284-4294.
Jensen et al., Design and Implementation of Adoptive Therapy with Chimeric Antigen Receptor-Modified T cells, 2014, Immunol. Rev. 257:127-144.
Jensen, Synthetic Immunobiology Boosts the IQ of T cells, Oct. 2015, Science 350:514-515.
Jensen et al., Designing Chimeric Antigen Receptors to Effectively and Safely Target Tumors, 2015, Curr. Opin. Immunol. 33:9-15.
Johnson et al., Rational Development and Characterization of Humanized Anti-EGFR Variant III Chimeric Antigen Receptor . . . , Feb. 2015, Sci. Transl. Med. 7:275ra22.
Juillerat et al., Design of Chimeric Antigen Receptors with Intergrated Controllable Transient Functions, 2016, Sci. Rep. 6:18950.
June, Drugging the Undruggable Ras—Immunotherapy to the Rescue? 2016, N. Eng. J. Med. 375:2286-2289.
Kakarla et al., CAR T cells for Solid Tumors: Armed and Ready to Go? Mar.-Apr. 2014, Cancer J. 20:151-155.
Kalos et al., Adoptive T cell Transfer for Cancer Immunotherapy in the Era of Synthetic Biology, Jul. 2013, Immunity 39:49-60.
Kawalekar et al., Distinct Signaling of Coreceptors Regulates Specific Metabolism Pathways and Impacts Memory Development . . . , 2016, Immunity 44:380-390.
Kebriaei et al., Future of Therapy in Acute Lymphoblastic Leukemia (ALL)—Potential Role of Immune-Based Therapies, 2015, Curr. Hematol. Malig. Rep. 10:76-85.

Kebriaei et al., Phase I Trials Using Sleeping Beuaty to Generate CD19-Specific CAR T cells, 2016, J. Clin. Invest. 126:3363-3376.
Kershaw et al., Clinical Application of Genetically Modified T cells in Cancer Therapy, May 2014, Clin. Transl. Immunol. 3:e16.
Kim et al., Highly Efficient RNA-Guided Genome Editing in Human Cells Via Delivery of Purified Cas9 Ribonucleoproteins, Jun. 2014, Gen. Res. 24:1012-1019.
Kis et al., Mammalian Synthetic Biology: Emerging Medical Applications, Mar. 2015, J. R. Soc. Interface 12:20141000.
Kochenderfer et al., Chemotherapy-Refractory Diffuse Large B-cell Lymphoma and Indolent B-cell Malignancies can be Effectively . . . , Aug. 2014, J. CLin. Oncol. 33:540-549.
Ledford, T-cell Therapy Extends Cancer Survival to Years, Dec. 2015, Nature 516:156.
Liang et al., Engineering Biological Systems with Synthetic RNA Molecules, 2011, Molc. Cell 43:915-926.
Lynn et al., Targeting of Folate Receptor-beta on Acute Myeloid Leukemia Blasts with Chimeric Antigen Receptor-Expressing T cells, May 2015, Blood 125:3466-3476.
Lindsten et al., Regulation of Lymphokine Messenger RNA Stability by a Surface-Mediated T Cell Activation Pathway, 1989, Science 244:339-343.
Liu et al., Affinity Tuned ErbB2 or EGFR Chimeric Antigen Receptor T Cells Exhibit an Increased Therapeutic Index Against Tumors in Mice, Sep. 2015, Cancer Res. 75:3596-3607.
Long et al., 4-1BB Cotimulation Ameliorates T cell Exhaustion Induced by Tonic Signaling of Chimeric Antigen Receptors, Jun. 2015, Nat Med 21:581-590.
Marcus et al., Allogenic Chimeric Antigen Receptor-Modified Cells for Adoptive Cell Therapy of Cancer, Mar. 2014, Expert Opin Biol Therap 14:947-954.
Mardiros et al., T cells Expressing CD123-Specific Chimeric Antigen Receptors Exhibit Specific Cytolytic Effector Functions . . . , Sep. 2013, Blood 122:3138-3148.
Maude et al., Chimeric Antigen Receptor T cells for Sustained Remissions in Leukemia, Mar. 2014, N. Eng. J. Med. 371:1507-1517.
Maus et al., Antibody-Modified T cells: CARs Take the Front Seat for Hematologic Malignancies, Apr. 2014, Blood 123:2625-2635.
Mayer, Nucleic Acid Aptamers: Selection, Characterization and Application, 2016, Humana Press, Springer Science.
Morgan et al., Case Report of a Serious Adverse Event Following the Administration of T cells Transduced with a Chimeric Antigen Receptor . . . , 2010, Molc Therap 18:843-851.
Nagy et al., Glyceraldehyde-3-phosphate Dehydrogenase Selectively Binds AU-Rich RNA in the NAD+-Binding Region, 1995, J Biol Chem 270:2755-2763.
Neeson, Lewis-Y Chimeric Antigen Receptor T cells Traffic and Persist in the Bone Marrow of Patients with Lewis-Y Positive AML, undated, Powerpoint SLides.
Nelson et al., Novel Immunotherapies for Hematologic Malignancies, Jan. 2015, Immunol. Rev. 263:90-105.
Newick et al., CAR T cell Therapy for Solid Tumors, Jul. 2016, Ann. Rev. Med. 68:3.1-3.14.
Norelli et al., Clinical Pharmacology of CAR-T cells: Linking Cellular Pharmacodynamics to Pharmacokinetics and Antitumor Effects, 2016, Biochim Biophys Acta 1865:90-100.
Okoye et al., The Protein LEM Promotes CD8+ T cell Immunity Through Effects on Mitochondrial Respiration, May 2015, Science 348:995-1001.
Paszkiewicz et al., Targeted Antibody-Mediated Depletion of Murine CD19 CAR T cells Permanently Reverses B cell Aplasia, 2016, J Clin Ivest 126:4262-4272.
Perales-Puchalt et al., Follicle-Stimulating Hormone Receptor is Expressed by Most Ovarian Cancer Subtypes and is a Safe . . . , 2016, Clin. Cancer Res.
Pizzitola et al., Chimeric Antigen Receptors Against CD33/CD123 Antigens Efficiently Target Primary Acute Myeloid Leukemia Cells in vivo, Aug. 2014, Leukemia 28:1596-1605.
Poirot et al., Multiplex Genome-Edited T-cell Manufacturing Platform for "Off-the-Shelf" Adoptive T-cell Immunotherapies, 2015, Cancer Res 75:3853-3864.

(56) References Cited

OTHER PUBLICATIONS

Posey et al., Engineered CAR T cells Targeting the Cancer-Associated Tn-Glycoform of the Membrane Mucin MUC1 Control Adenocarcinoma, 2016, Immunity 44:1444-1454.
Qin et al., Systematic Comparison of Constitutive Promoters and the Doxycycline-Inducible Promoter, 2010, PLoS ONE 5:e10611.
Rakhit et al., Chemical Biology Strategies for Posttranslational Control of Protein Function, Sep. 2014, Chem Biol 21:1238-1252.
Reddy, Changing Landscape of Immuno-Oncology: CAR-T Therapy and PD1/PDL1 Blockade, 2016, Boston University Theses.
Renert, Novel Immunotherapeutic Approaches to the Treatment of Cancer: Drug Development and Clinical Application, 2016, Springer International Publishing.
Rodgers et al., Switch-Mediated Activation and Retargeting of CAR-T cells for B-cell Malignancies, 2016, Proc Natl Acad Sci 113:E459-E468.
Rosenberg, Cell Transfer Immunotherapy for Metastataic Solid Cancer—What Clinicians Need to Know, 2011, Nat Rev Clin Oncol 8:577-585.
Rosenberg et al., Adoptive Cell Transfer as Personalized Immunotherapy for Human Cancer, Apr. 2015, Science 348:62-68.
Roybal et al., Precision Tumor Recognition by T cells with Combinatorial Antigen-Sensing Circuits, 2016, Cell 164:770-779.
Roybal et al., Engineering T cells with Customized Therapeutic Response Programs Using Synthetic Notch Receptors, 2016, Cell 167:1-14.
Sadelain et al., Sage Harbours for the Integration of New DNA in the Human Genome, 2012, Nat. Rev. 12:51-58.
Sandberg et al., In Cancer Immunotherapy Legal Battle, *It's Now Juno v. Novartis*, Feb. 2014, Pharma MedTech Bus Intell. 2014900027.
Shi et al., Chimeric Antigen Receptor for Adoptive Immunotherapy of Cancer: Latest Research and Future Prospects, Sep. 2014, Molc Cancer 13:219.
Sommermeyer et al., Chimeric Antigen Receptor-Modified T cells Derived from Defined CD8+ and CD4+ Subsets Confer Superior Antitumor . . . , Feb. 2016 Leukemia 30:492-500.
Srivastava et al., Engineering CAR-T cells: Design Concepts, Aug. 2015, Trends Immunol 36:494-502.
Sun et al., The Quest for Spatio-Temporal Control of CAR T cells, Dec. 2015, Cell Res. 25:1281-1282.
Tettamanti et al., CD123 AML Targeting by Chimeric Antigen Receptors: A Novel Magic Bullet for AML Therapeutics? May 2014, Oncolimmunol 3:e28835.
Till et al., Adoptive Immunotherapy for Idolent Non-Hodgkin Lymphoma and Mantle Cell Lymphoma Using Genetically Modified . . . , 2008, Blood 112:2261-2271.
Turatti et al., Redirected Activity of Human Antitumor Chimeric Immune Receptors is Governed by Antigen and Receptor Expression Levels . . . , 2007, J Immunotherap 30:684-693.
Turtle et al., CD19 CAR-T cells of Defined CD4+:CD8+ Composition in Adult B cell ALL Patients, 2016, J Clin Ivest 126:2123-2138.
Turtle et al., Immunotherapy of Non-Hodgkin's Lymphoma with a Defined Ratio of CD8+ and CD4+ CD19-Specific Chimeric Antigen Receptor . . . , 2016, Sci Transl Med 8:355ra116.
Vanderlugt et al., Epitope Spreading in Immune-Mediated Diseases: Implications for Immunotherapy, 2002, Nat Rev 2:85-95.
Vigano et al., Functional Avidity: a Measure to Predict the Efficacy of Effector T cells? 2012, Clin Develop Immunol 2012:153863.
Wang et al., ZAP-70: An Essential Kinase in T-cell Signaling, 2010, Cold Spring Barb Perspect Biol 2:a002279.
Wang et al., One-Step Generation of Mice Carrying Mutations in Multiple Genes by CRISPR/Cas-Mediated Genome Engineering, 2013, Cell 153:910-918.
Wang et al., Manufacture of tumor- and virus-specific T lymphocytes for adoptive cell therapies, Feb. 2015, Cancer Gene Therapy 22:85-94.
Watanabe et al., Target Antigen Density Governs the Efficacy of Anti-CD20-CD28-CD3 Zeta Chimeric Antigen Receptor-Modified . . . , Dec. 2014, J Immunol 194:911-920.
Weigand et al., Tetracycline Aptamer-Controlled Regulation of Pre-mRNA Splicing in Yeast, 2007, Nucl Acids Res 35:4179-4185.
Win et al., A Modular and Extensible RNA-Based Gene-Regulatory Platform for Engineering Cellular Function, 2007, Proc Natl Acad Sci 104:14283-14288.
Win et al., Frameworks for Programming Biological Function Through RNA Parts and Devices, 2009, Chem Biol 16:298-310.
Wu et al., Remote Control of Therapeutic T cells Through a Small Molecule-Gated Chimeric Receptor, Sep. 2015, Science 350:aab4077.
Xie et al., Mammalian Designer Cells: Engineering Principles and Biomedical Applications, Jul. 2015, Biotechnol J 10:1005-1018.
Xie et al., Synthetic Biology—Application-Oriented Cell Engineering, 2016, Curr. Opin. Biotechnol. 40:139-148.
Ye et al., Synthetic Mammalian Gene Circuits for Biomedical Applications, 2013, Curr. Opin. Chem Biol 17:910-917.
Zhao et al., Structural Design of Engineered Costimulation Determines Tumor Rejection Kinetics and Persistence of CAR T cells, Oct. 2015, Cancer Cell 28:415-428.
Zheng et al., Protein L: A Novel Reagent for the Detection of Chimeric Antigen Receptor (CAR) Expression by Flow Cytometry, 2012, J Transl Med 10:29.
Muti, ASH Conference Review, 2014.
Zhong et al., Rational Design of Aptazyme Riboswitches for Efficient Control of Gene Expression in Mammalian Cells, Nov. 2016, eLife 5:e18858.
Auslander et al., A ligand-dependent hammerhead ribozyme switch for controlling mammalian gene expression, Molc. Biosys. vol. 6, pp. 807-814 (2010).
Chen et al, Selective degradation of early-response gene mRNAs: functional analysis of sequence features of the AU-rich elements, 1994, Mol Cell Biol vol. 14, pp. 8471-8482.
Drury et al, FasL expression in activated T-lymphocytes involves HuR mediated stabilization, 2010, J. Biol. Chem. vol. 285, pp. 31130-31138.
Larsen et al., Sensitivity to restimulation-induced cell death is linked to glycolytic metabolism in human T-cells, 2016, J. Immunol. vol. 198, pp. 147-155.
U.S. Appl. No. 15/800,621, filed Nov. 1, 2017. Ligand Matched Transcriptional Control, Control Devices, and Solute Carriers.
U.S. Appl. No. 15/850,288, filed Dec. 21, 2017. Smart CAR Devices, DE CAR Polypeptides, Side CARs and Uses Thereof.
U.S. Appl. No. 16/655,175, filed Oct. 16, 2019, Gold Optimized CAR T-cells.
U.S. Appl. No. 16/940,180, filed Jul. 27, 2020. Gold Optimized CAR T-cells.
U.S. Appl. No. 16/993,782, filed Aug. 14, 2020. Combination Therapy with Gold Controlled Transgenes.
U.S. Appl. No. 16/999,623, filed Aug. 21, 2020. Gold Optimized CAR T-cells.
U.S. Appl. No. 17/331,398, filed May 26, 2021. Gold Optimized CAR Natural Killer cells.
U.S. Appl. No. 17/331,423, filed May 26, 2021. Coordinating Gene Expression Using RNA Destabilizing Elements.
U.S. Appl. No. 17/365,912, filed Jul. 1, 2021. Ligand Matched Transcriptional Control, Control Devices, and Solute Carriers.
U.S. Appl. No. 17/379,514, filed Jul. 19, 2021. Methods for Making Novel Antigen Binding Domains.
U.S. Appl. No. 17/355,693, filed Jun. 23, 2021. Coordinating Gene Expression Using RNA Destabilizing Elements.
U.S. Appl. No. 17/504,317, filed Oct. 18, 2021. Mercury Controlled Gene Expression.
U.S. Appl. No. 17/683,075, filed Feb. 28, 2022. Gold Optimized CAR T-cells.
U.S. Appl. No. 17/693,802, filed Mar. 14, 2022. Gold Optimized CAR T-cells.
U.S. Appl. No. 17/702,544, filed Mar. 23, 2022. Gold Optimized CAR T-cells.

\* cited by examiner

COMBINATION THERAPY WITH GOLD CONTROLLED TRANSGENES

This application is continuation of U.S. application Ser. No. 16/993,782 filed Aug. 14, 2020, which claims priority to U.S. provisional application Ser. No. 62/888,524 filed Aug. 18, 2019, U.S. provisional application Ser. No. 62/965,569 filed Jan. 24, 2020, and U.S. provisional application Ser. No. 63/054,721 filed Jul. 21, 2020.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CBIO046_ST25.txt", a creation date of Jan. 24, 2020, and a size of 9 kilobytes. The Sequence Listing filed via EFS-Web is part of the specification and is incorporated in its entirety by reference herein.

BACKGROUND OF THE INVENTION

Chimeric Antigen Receptors are human engineered receptors that may direct a T-cell to attack a target recognized by the CAR. For example, CAR T cell therapy has been shown to be effective at inducing complete responses against acute lymphoblastic leukemia and other B-cell-related malignancies and has been shown to be effective at achieving and sustaining remissions for refractory/relapsed acute lymphoblastic leukemia (Maude et al., NEJM, 371:1507, 2014). However, dangerous side effects related to cytokine release syndrome (CRS), tumor lysis syndrome (TLS), B-cell aplasia and on-tumor, off-target toxicities have been seen in some patients.

There are currently two extant strategies to control CAR technology. The first is an inducible "kill switch." In this approach, one or more "suicide" genes that initiate apoptotic pathways are incorporated into the CAR construct (Budde et al. PLoS1, 2013 doi:10.1371/journal.pone.0082742). Activation of these suicide genes is initiated by the addition of AP1903 (also known as rimiducid), a lipid-permeable tachrolimus analog that initiates homodimerization of the human protein FKBP12 (Fv), to which the apoptosis-inducing proteins ace translationally fused. In the ideal scenario, these kill switches endeavor to sacrifice the long-term surveillance benefit of CAR technology to safeguard against toxicity. However, in vivo, these suicide switches are not likely to realize this goal, as they are operating against powerful selection pressures for CAR T-cells that do not respond to AP1903, a situation worsened by the inimical error-prone retroviral copying associated with the insertion of stable transgenes into patient T-cells. In this scenario, non-responsive CAR T-cell clones will continue to proliferate and kill target cells in an antigen-dependent manner. Thus, kill switch technology is unlikely to provide an adequate safeguard against toxicity.

The second CAR regulatory approach is transient CAR expression, which can be achieved in several ways. In one approach, T-cells are harvested from unrelated donors, the HLA genes are deleted by genome-editing technology and CAR-encoding transgenes are inserted into the genome of these cells. Upon adoptive transfer, these CAR T-cells will be recognized by the recipient's immune system as being foreign and destroyed, thus the CAR exposure in this system is transient. In another transient CAR exposure approach, mRNA of a CAR-encoding gene is introduced into harvested patient T-cells (Beatty, G L 2014. Cancer Immunology Research 2 (2): 112-20. doi:10.1158/2326-6066.CIR-13-0170). As mRNA has a short half-life and is not replicated in the cell or stably maintained, there is no permanent alteration of the CAR-expressing T-cell, thus the CAR expression and activity will be for a short period of time. However, as with the kill-switch approach, these transient CAR exposure approaches sacrifice the surveillance benefit of CARs. Additionally, with these transient systems acute toxicity can be difficult to control.

SUMMARY OF THE INVENTION

In an aspect, the description discloses new chimeric antigen receptors (CARs) that use a knottin (an inhibitor cystine-knot protein or cysteine knot protein) as the antigen recognition portion of the CAR. Knottins can be engineered to recognize targets of interest as knottins have a core structure (scaffold) with peptide loops around the core structure which peptide loops can be engineered to produce different binding properties and specificities. Knottins can be small and so have the properties of a small molecule with the binding affinity of a biologic (such as an antibody). Knottins have high stability to pH, heat, and enzymes.

In an aspect, the description discloses a eukaryotic cell with a CAR, T-cell receptor, or other targeting polypeptide and a transgene under the control of an RNA Destabilizing Element (RDE). The RDE may control multiple transgenes or multiple RDEs may control multiple transgenes. The multiple transgenes may be arranged serially and/or as a concatemer and/or in other arrangements. Multiple RDEs may be used to regulate a transgene, and these multiple RDEs can be organized as a concatemer, interspersed within a region of the transcript, or located in different parts of the transcript. Multiple transgenes can be regulated by an RDE or a combination of RDEs. The RDEs can be localized in the 3'-UTR, the 5'-UTR and/or an intron. RDEs can include, for example, the RDEs from AU 1 (CD40L), AU 2 (CSF2), AU 3 (CD247), AU 4 (CTLA4), AU 5 (EDN1), AU 6 (IL2RA), AU 7 (SLC2A1), AU 8 (TRAC), AU 9 (CD274), AU 10 (Myc), AU 11 (CD19), AU 12 (IL4), AU 13 (IL5), AU 14 (IL6), AU 15 (IL9), AU 16 (IL10), AU 17 (IL13), AU 18 (FOXP3), AU 19 (TMEM-219), AU 20 (TMEM-219snp), AU 21 (CCR7), AU 22 (SEM-A4D), AU 23 (CDC42-SE2), AU 24 (CD8), AU 27 (bGH), and/or AU 101 (Interferon gamma or IFNg). Other RDEs are disclosed in the following description. RDE control can also be combined with codon optimization of the transgene to increase the GC content of the wobble position (third position of the codon) in some or all of the codons of the transgene. This codon optimization can increase efficiency of expression (the on signal) by up to 100-fold. Such codon optimized transgenes can be linked to an RDE and produce a larger dynamic range of expression from the RDE control compared to the transgene-RDE without codon optimization.

In an aspect, the RDE can be under the control of a RNA control device. Such, Smart RDEs place the RDE control under the regulation of the RNA control device which introduces ligand control to the RDE. The RNA control device can disrupt the RDE when ligand is bound (or not bound) resulting in loss of the RDE control, and when ligand is added (or removed) the RNA control device is inhibited and the RDE structure is available for interaction with RNA binding proteins. The RNA control device could also act upon a portion of the transcript that disrupts the RDE (e.g., the portion of the transcript could form secondary structures with the RDE that inhibit RNA binding proteins from binding to the RDE), when the RNA control device binds (or is free from ligand) the RNA control device disrupts the inhibitory portion of the transcript so it is not available to interact with the RDE, and the RDE is now available to interact with RNA binding proteins. This RNA control device regulation allows the activity of the RDE to be ligand controlled through the action of the RNA control device.

In an aspect, a therapy utilizing a CAR T-lymphocyte with or without an RDE controlled transgene(s) is combined or in an order of succession with another therapy. The other therapy can include any therapeutic molecule including, for example, a polypeptide, lipid, carbohydrate, nucleic acid, small molecule drug, biological drug, antibody, antibody-drug-conjugate, or combinations of the foregoing. Suitable molecules are described below. The other therapy can be administered to a subject at the same time as the CAR therapy (with or without a RDE controlled transgene(s)), before the administration of the CAR therapy (with or without a RDE controlled transgene(s)), or after the administration of the CAR therapy (with or without a RDA controlled transgene(s)). For example, a subject could be treated with chemotherapy and/or an immunotherapy (e.g., an antibody-drug conjugate), followed by treatment with a CAR T-cell with optionally a RDE controlled payload. The CAR T-cell treatment can be given the subject at varying times after the chemotherapy and/or immunotherapy, e.g., one, two, three, four, five, or six weeks. The chemotherapy and/or immunotherapy (e.g., ADC) can be cycled with the CAR T-cell treatment for multiple cycles of treatment. Treatment with CAR T-cells may also be boosted with target X peptide, or virus or cells loaded with target X peptide (target X is the target bound by the CAR).

In an aspect, an RDE, combination of RDEs, and/or modified RDEs can be used to provide desired kinetic parameters to the regulation of a gene product including, for example, amount of expression, steady state concentration, $C_{max}$ (maximal concentration of gene product obtained), $T_{max}$ (time to reach $C_{max}$), baseline expression, speed of induction (acceleration), induction rate (velocity), dynamic range also known as fold regulation (induced expression/basal expression), maximal dynamic range ($DR_{max}$), time to $DR_{max}$, area under the curve (AUC), etc. A RDE construct can be made that has a desired set of kinetic parameters to provide the level, degree, temporal, and amount of regulation that is desired. In addition, RDE concatemers can be used to alter the kinetic performance of a construct.

Combinations of RDEs can be used to provide temporal regulation between two or more transgenes. RDEs can be selected to provide maximal rates of expression (and different amounts of maximal expression) at different times following activation of a cell (or induction of expression). This temporal control allows a first transgene encoded polypeptide to alter the state of the cell so that the cell is prepared to be acted upon by a second polypeptide encoded by a second transgene with an RDE that provides later in time expression. This temporal control can also be used to time the expression of two, three or more transgenes following activation of a cell. If the transgene encoded polypeptides are secreted, they can act in a temporal fashion upon target cells. For example, a first transgene polypeptide (with an early expression RDE) could be secreted and act upon a target cell to change its state (e.g., induce the expression of receptor). The second transgene polypeptide is expressed at a later time (under the control of a later expression RDE) and acts upon the target cell with the changed state (e.g., the second protein can be a ligand for the induced receptor).

In an aspect, the RDE can be engineered to increase or decrease the binding affinity of RNA binding protein(s) that interact with the RDE. Altering the affinity of the RNA binding protein can change the timing and response of transgene expression as regulated by the RNA binding protein. In an aspect, the RNA binding protein binding at the RDE is altered by the metabolic state of the cell and changing the binding affinity of the RDE for the RNA binding protein alters the response to and/or timing of transgene expression with the metabolic state of the cell. In an aspect, the RNA binding protein binding at the RDE is altered by the redox state of the cell and changing the binding affinity of the RDE for the RNA binding protein alters the response to and/or timing of transgene expression with the redox state of the cell.

In an aspect, the CAR, T-cell receptor, B-cell receptor, innate immunity receptor, or other targeting receptor or targeting polypeptide recognizes an antigen at the target site (e.g., tumor cell or other diseased tissue/cell) and this activates the cell. The transgene can be another CAR that recognizes a second antigen at the target site and activation of the cell by the first CAR, T-cell receptor or other targeting polypeptide induces the second CAR allowing the eukaryotic cell to recognize the target site by a second antigen. In an aspect, the eukaryotic cell has a first CAR that recognizes an antigen at a target site and this activates a transgene (through an RDE) that encodes a polypeptide that directly or indirectly reduces the activation state of the cell. For example, the transgene may encode a second CAR that recognizes an antigen on healthy tissue so that when the first CAR reacts with antigen at a nontarget cell, the eukaryotic cell will be de-activated by the second CAR interaction with the healthy cell antigen (that is not present or is present in reduced amounts at the target site).

In some aspects, the eukaryotic cell is an immune cell, e.g., a T-cell, a natural killer cell, a B-cell, a macrophage, a dendritic cell, or other antigen presenting cell. In these aspects, activation of the cell by the CAR or changing the metabolic state of the immune cell in other ways can induce expression of the transgene through the RDE. The RDE that controls the transgene can have microRNA binding sites and can be engineered to remove one or more of these microRNA binding sites. The RDE can be bound by the Hu Protein R (HuR). Without wishing to be bound by theory it is expected that HuR can bind to some RDEs, and act to stabilize the mRNA, leading to enhanced translation. Some RDEs can be tied to the glycolytic state of the eukaryotic cell through the enzyme glyceraldehyde 3-phosphate dehydrogenase (GAPDH), other dehydrogenases, other oxidoreductases, or other glycolytic enzymes that can bind to an RDE when the eukaryotic cell is not activated (low glycolytic activity), quiescent, or at rest. When GAPDH or the other enzymes bind to the RDE this can reduce half-life of the RNA with the RDE. In this aspect, CAR activation of the eukaryotic cell (e.g., T-lymphocyte) can induce glycolysis in the cell which reduces GAPDH binding of the RNA, increases half-life of the RNA, which produces increased expression of the transgene encoded in the RNA and controlled by the RDE. Without wishing to be bound by theory, as GAPDH vacates the RDE, HuR or other RDE binding proteins may subsequently bind either the same RDE, or a previously inaccessible RDE (sterically hindered by presence of GAPDH), further stabilizing the mRNA, increasing half-life of the mRNA, and producing further increased expression of the transgene encoded by the RNA and controlled by said RDE. Thus, CAR activation can induce expression of the transgene. In other aspects, other activation of the immune cell can cause GAPDH to engage in glycolysis and so induce expression of the transgene under the control of the RDE. Examples of RDEs bound by GAPDH include, for example, AU 19 (TMEM-219), AU 20 (TMEM-219snp), AU 21 (CCR7), AU 22 (SEM-A4D), and AU 23 (CDCl42-SE2).

Expression from the transcript with the RDE(s) can respond to the metabolic state of the cell. For example, the RDE can be bound by metabolic or glycolytic enzymes which couples expression of the transgene to the activation state of the cell through these metabolic or glycolytic enzymes. Some metabolic or glycolytic enzymes bind to RDEs in the transcript and degrade or target for degradation the transcript. When those metabolic or glycolytic enzymes become active, the enzymes no longer bind to the RDEs, the transcripts are stable for a longer period of time, and the transcripts can be translated for this longer period of time. Cells expressing transgenes under the control of such RDEs can also be engineered to express a CAR that can alter the metabolic state of the cell at desired times resulting in expression of the transgene at the desired time. Alternatively, other stimuli can be used to alter the metabolic state of the eukaryotic cell resulting in expression of the transgene. For example, the metabolic state of the cell can be altered to cause transgene expression (or to inhibit expression) by stimuli including, for example, small molecules (e.g., PMA/ionomycin), cytokines, a TCR and costimulatory domain engagement with ligand, oxygen levels, cellular stress, temperature, or light/radiation.

GAPDH binding to the RDE can be increased by introducing into the cell a small molecule that inhibits glycolysis such as, for example, dimethylfumarate (DMF), rapamycin, 2-deoxyglucose, 3-bromophyruvic acid, iodoacetate, fluoride, oxamate, ploglitazone, dichloroacetic acid, or other metabolism inhibitors such as, for example, dehydroepiandrosterone. Other small molecules can be used to reduce GAPDH binding to the RDE. Such small molecules may block the RDE binding site of GAPDH including, for example, CGP 3466B maleate or Heptelidic acid (both sold by Santa Cruz Biotechnology, Inc.), pentalenolactone, or 3-bromopyruvic acid. Other small molecules can be used to analogously inhibit other enzymes or polypeptides from binding to RDEs. Other small molecules can be used to change the redox state of GAPDH, leading to an altered affinity of GAPDH for the RDE. Other small molecules known to interact with GAPDH function, such as vitamin C, saframycin, salicylic acid, insulin, vitamin d3, metformin, or suramin can modify the binding of GAPDH for the RDE. Other molecules can modify the binding of GAPDH for the RDE including trehalose, galactose and other saccharides. Other molecules known to alter GAPDH structure can modify the binding of GAPDH for the RDE including nitric oxide and hydrogen sulfide.

GAPDH binding of RDEs can also be modified by acetyl-CoA. GAPDH can be acetylated at a number of Lysines in the GAPDH sequence. Bond et al, FASEB J. 31:2592-2602 (2017), which is incorporated by reference in its entirety for all purposes. Acetylation at Lysine 254 can increase GAPDH activity in response to glucose. ATP citrate lyase (ACLY) can increase the level of acetyl-CoA in a cell thereby increasing the acetylation of GAPDH. ACLY can be expressed in eukaryotic cells (e.g., an immune cell such as a T-cell) at a desired time which can increase acetylation of GAPDH which can increase expression from RDE controlled transcripts. For example, ACLY can be used as a payload regulated by an RDE. In this example, a eukaryotic cell (e.g., an immune cell) is activated and the RDE controlled ACLY is expressed. The ACLY can increased acetylation of GAPDH which can cause more expression from RDE controlled transcripts. In this example, if another payload is under control of an RDE the increase in expression that payload can be increased by the co-expression of ACLY as acetylation reduces the GAPDH bound to RDEs.

In an aspect, alternative splicing is used to complement or in lieu of RDE control to tie cell activation and/or change in metabolic state to the expression of a transgene. For example alternative splicing mediated by hnRNPLL can be used. hnRNPLL is expressed when immune cells (e.g., T-cells or B-cells) are activated. hnRNPLL binds to RNA transcripts and can cause the retention or excision of introns and/or exons resulting in alternative splicing of RNAs (e.g., mRNAs). hnRNPLL alternative splicing control can be used alone or in combination with RDE control to regulate the expression of transgenes. When a cell is activated (e.g., by ligand binding at a receptor which can change a cell's metabolic state) it can induce expression of hnRNPLL, which can produce alternative splicing products in transcripts with hnRNPLL binding sites. As discussed above and below, such cell activation also induces expression in transcripts with RDE sites. By combining RDE control with hnRNPLL control the dynamic range of control for a transgene upon cell activation (e.g., receptor binding of ligand) can be increased.

In an aspect, activation of the immune cell induces expression of the transgene that can encode a payload to be delivered at the target (activation) site. The transgene can encode a payload for delivery at the site of CAR activation and/or immune cell activation and/or other receptor activation. The payload can be a cytokine, an antibody, a reporter (e.g., for imaging), a receptor (such as a CAR), or other polypeptide that can have a desired effect at the target site. The payload can remain in the cell, or on the cell surface to modify the behavior of the cell. The payload can be an intracellular protein such as a kinase, phosphatase, metabolic enzyme, an epigenetic modifying enzyme, a gene editing enzyme, etc. The payload can be a gene regulatory RNA, such as, for example, siRNA, microRNAs (e.g., miR155), shRNA, antisense RNA, ribozymes, and the like, or guide RNAs for use with CRISPR systems. The payload can be a nucleic acid (e.g., a vector, or a human artificial chromosome (HAC)). The payload can also be a membrane bound protein such as GPCR, a transporter, etc. The payload can be an imaging agent that allows a target site to be imaged (target site has a desired amount of target antigen bound by the CAR). The payload can be a checkpoint inhibitor, and the CAR and/or other binding protein (e.g., T-cell receptor, antibody or innate immunity receptor) can recognize a tumor associated antigen so the eukaryotic cell preferentially delivers the checkpoint inhibitor at a tumor. The payload can be a cytotoxic compound including, for example, a granzyme, an apoptosis inducer, a cytotoxic small molecule, or complement. The payload can be an antibody, such as for example, an anti-4-1BB agonist antibody (an anti-CD137 antibody), an anti-IL 1b antibody (anti-inflammatory), anti-CD29/anti-VEGF antibody, an anti-CTLA4 antibody, a bispecific antibody (e.g., BiTE), or an anti-CD11b antibody. The payload can be an immune polypeptide, including for example, cytokines (e.g., IL-2, IL-12, IL-15, IL-18), chemokines (e.g., CXCL12), perforins, granzymes, and other immune polypeptides. The payload can be an enzyme including for example, hyaluronidase, or heparinase. The payload can be a polypeptide including for example, ApoE (e.g., ApoE2, ApoE3 and ApoE4), NO synthase (e.g., iNOS, nNOS, eNOS), HSV-thymidine kinase (HSV-TK), antagonists of CSF1 receptor, CCR2, CCR4, a BiTE (activates immunosuppressed T-cells), soluble CD40 ligand, HSP70, and HSP60. The payload can be fused or associated with Decorin, Biglycan, fibromodulaon/Lumican so that the payload binds to the collagen near or in the target site. This strategy is particularly useful for keeping cytotoxic payloads localized to the target cells (e.g., a tumor). The payload can be a transgene(s) which delivers a virus as a payload. For example, the RDE can control a master control element that controls the expression of the virus genes for replication and coat/envelope proteins. Alternatively, the Rep and coat/envelope proteins can be placed under the control of inducible promoters that are controlled by a regulatory protein, and that regulatory protein can be controlled by an RDE. Still alternatively, the Rep proteins of the virus can be placed under the control of an RDE, and/or the coat/envelope proteins of the virus can be placed under the control of an RDE. As with other payloads this complex payload can use CAR T-cell regulation or any other regulation that induces glycolysis in a cell. Helper constructs in a T cell, or other delivery cell can encode the genes needed for viral replication and viral packaging.

In some aspects, the expression of CAR, DE-CAR and/or Side-CAR polypeptide is controlled, at least in part, by an RDE that interacts with a glycolytic enzyme with RDE binding activity, e.g., GAPDH. The glycolytic enzyme can bind to the RDE and reduce production of the CAR, DE-CAR, Side-CAR polypeptide, and/or other transgene product. This reduction in polypeptide production can occur because of an inhibition of translation and/or an increase in the rate of mRNA degradation (RDE binding can shorten the half-life of the mRNA). Some RDE binding proteins may reduce translation and enhance degradation of RNA to reduce the level of polypeptide made. The RDE can be an AU rich element from the 3' UTR of a transcript (e.g., a transcript encoding IL-2 or IFN-γ), or can be a modified 3' UTR that has been engineered to remove one or more microRNA sites (e.g., modified 3'-UTRs of IL-2 or IFN-γ). In an aspect, the expression of the transgene, CAR, DE-CAR and/or Side-CAR polypeptide under the control of an RDE bound by a glycolytic enzyme(s), e.g., GAPDH, is increased by increasing the activity of the enzyme(s) in prosecuting glycolysis. The activity of enzymes in glycolysis can be increased by providing the cell with increased glucose in the cell medium, increasing triose isomerase activity in the cell, or providing the cell with a compound that increases glycolysis in the cell, e.g., tamoxifen or glucose. The RDE can bind to Hu Protein R (HuR). Without wishing to be bound by theory it is expected that HuR binds to some AU-rich RDEs and U-rich RDEs, and can act to stabilize the mRNA, leading to enhanced translation. Thus, cell conditions that result in increased HuR expression can increase expression of transgenes with appropriate AU-rich elements and/or U-rich elements, and conditions that reduce HuR expression can decrease expression of these transgenes. HuR interaction with the 3' UTR of the transgene (or native genes) can also be altered by expressing a recombinant transcript containing HuR binding sites. Expression of these transcripts will reduce the amount of HuR available to bind to the transgene transcript or native HuR regulated transcripts and reduce the half-lives of these transcripts resulting in decreased expression.

In an aspect, RDE control can be used to lower CAR expression in a subject which can reduce the availability of CAR polypeptide for immune reactions. This can lower the immunogenicity of transgenic immune cells with the CAR. In part, this lower immunogenicity occurs because the CAR peptide has lower exposure to the immune system.

In an aspect, nucleic acids can be used to boost the response of immune cells upon stimulation of the immune cell. For example, the immune cell can produce higher amounts of immune polypeptides (greater $C_{max}$) with faster kinetics of production. The immune polypeptides can include, for example, cytokines, perforins, granzymes, apoptosis inducing polypeptides, etc. The nucleic acids that boost the immune response can comprise control regions operably linked to nucleic acids encoding RDEs for selected RDE binding proteins, so that upon expression of the nucleic acid into RNA the RDEs in the RNA bind the RDE binding proteins that repress expression of a polypeptide, for example, cytokines, perforins, granzymes, and other immune polypeptides. The expression of the RNAs with the RDEs can poise the eukaryotic cell for expression of polypeptide controlled by RDEs. For example, the expression of RNAs with the RDEs may be done in immune cells to poise the cell for expression of immune polypeptides upon stimulation of the immune cell.

In an aspect, the CAR, DE-CAR, Side-CAR polypeptides, and/or other receptor can be directed against antigens found on acute myeloid leukemia (AML) cells including, for example, CD 33, CD 34, CD 38, CD43, CD 44, CD 45, CD 45RA, CD 47, CD 64, CD 66, CD 123, CD 133, CD 157, CLL-1, CXCR4, LeY, PR1, RHAMM (CD 168), TIM-3, and/or WT1. The monoclonal antibody 293C3-SDIE can be used as the extracellular element for the CAR, DE-CAR and/or Side-CAR polypeptides. (Rothfelder et al., 2015, at ash.confex.com/ash/2015/webprogram/Paper81121.html, which is incorporated by reference in its entirety for all purposes) Other antigens for AML are known in the art and may be the target of the CAR, DE-CAR, Side-CAR, and/or other receptor. An onco-sialylated CD 43 has been associated with acute myeloid leukemia (AML) and this onco-sialylated CD 43 is not found on normal cells and tissue. This onco-sialylated CD 43 is bound by the monoclonal antibody AT14-013, and the variable region of this antibody is used to make an anti-onco sialylated CD 43 CAR. AT14-013 recognizes the unique sialylation epitope found on this onco-sialylated CD 43. This CAR is specific for AML and does not have side reactivity with normal tissue in a subject. In an aspect, the CAR, DE-CAR, Side-CAR polypeptides, and/or other receptor can be directed against antigens found on diffuse large cell B-cell lymphoma (DLBCL) cells including, for example, CD19, CD20, CD22, CD79a, CD5, CD10, and CD43. Other antigens for DLBCL are known in the art and may be the target of the CAR, DE-CAR, Side-CAR, and/or other receptor.

Other antigens that can be targeted by the CAR, DE-CAR, side-CAR or other receptor include, for example, DLL3, HER2, PSCA, CSPG4, EGFRvIII, MSLN (mesothelin), FAP, MUC16 (CA-125), CEA, CD133 (PROM1), IL13Ra, CD171 (L1CAM), CD123, (IL3R), CD33 (SIGLEC3), LeY, GUCY2C, BCMA and/or EPHA2. Eukaryotic cells with CAR, DE-CAR, side-CAR or other receptors targeting these antigens can include a payload such as, for example, one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-12, IL-15, IL-18, INFγ, miRNA (e.g., mir155), CD40 ligand, ApoE3, ApoE4, TNFα, CCR2, CCR4/CXCL12, ACLY, antagonists of CSF1 receptor, siRNA, other antisense RNAs, and/or anti-CD28 antibody (including full length and fragments such as single chain antibodies). The payload can be presented as a fusion protein with a Small Leucine Rich Proteoglycans (SLRPs) such as Decorin, Biglycan and/or Lumican (all of which can anchor the fusion protein to the cellular matrix in or near the target site). Fusions with Decorin and/or Biglycan can also bind TGF-beta in and around the target site which can reduce immune suppression. Myeloid modifying payloads ("MM payloads") which reduce immune suppression or inhibition caused by myeloid cells may be delivered including, for example, ApoE3, ApoE4, Hsp60, Hsp70, TNFα, antagonists of CSF1 receptor, CD40L (CD154) and/or IL-12. Two or more MM payloads can also be delivered by the CAR, DE-CAR, side-CAR and/or other receptor cell (e.g., T-cell) using RDEs that produce different pharmacokinetics for delivery. For example, the different MM payloads could be controlled by different RDEs so that the $C_{max}$ of delivery for the different MM payloads occurs at different times.

AB toxins can be used to engineer fusion payloads that deliver a desired protein product into a target cell. AB toxins include, for example diphtheria toxin, tetanus toxin, exotoxin A of *P. aeruginosa*, iota toxin Ia of *C. perfringens*, C2 toxin CI of *C. botulinum*, ADP-ribosyltransferase of *C. difficile*, etc. The AB toxin can be engineered to replace the catalytic (toxic) component (A domain) of the AB toxin with the desired protein so that the modified AB toxin binds its receptor and delivers the desired protein into a target cell through the B domain of the AB toxin. These B toxin fusions can also be engineered to replace the receptor binding portion of the B domain with a binding domain (e.g., ligand) that binds to a desired antigen and/or receptor on a desired target cell. These modified B toxin fusions can deliver a desired protein payload into a target cell using the B domain of the toxin.

The CAR, DE-CAR, Side-CAR polypeptides, and/or other receptor can be directed against antigens found on solid tumors such as, for example, integrins such as αvβ6 (found on numerous solid tumors (including, for example, oral squamous cell cancer, colon cancer, pancreatic cancer, gastric cancer, breast cancer, ovarian cancer, cervical cancer, lung cancer, etc.).

In an aspect, small molecules and other molecules that affect the availability of GAPDH or other RDE binding proteins to bind RDEs can be used to regulate gene expression by GAPDH, other RDE binding glycolysis enzymes, and/or other RDE binding enzymes involved in energy and cell metabolism. Molecules that increase glycolysis in a cell can reduce the amount of GAPDH available for binding to RDEs which can increase translation from transcripts under GAPDH control. Similarly, other glycolysis enzymes and metabolic enzymes can bind to RDEs and activating glycolysis and other energy pathways in the cell can reduce the amount of these enzymes that are available to bind their corresponding RDEs. This reduced binding can increase translation from transcripts controlled by these RDE binding proteins (enzyme binding to the RDE decreases expression) or can decrease translation if enzyme binding has a positive effect on expression. These molecules can also be useful in the treatment of certain types of neural degeneration associated with inflammation and/or autoimmune diseases. These molecules can be used to alter the amount of GAPDH in immune cells so that RDEs are bound and the immune cells reduce expression of RDE regulated genes. Some genes under RDE control in immune cells are associated with inflammation and so, molecules that increase the amount of RDE binding proteins that inhibit the inflammatory associated transcripts could reduce inflammation.

A nucleic acid construct encoding a transcript with selected RDEs can be expressed in an immune cell, for example, a T-lymphocyte. The recombinant transcript with the selected RDEs can bind to and deplete the levels of RDE binding proteins in the T-lymphocyte so that transcripts encoding polypeptides regulated by the depleted RDE binding proteins are expressed at different threshold points of activation for other cellular signals. The use of the RDE constructs can increase the kinetics of expression and/or the Cmax of expression of the polypeptides whose expression is controlled by the RDE.

In an aspect, CAR T-lymphocytes are modified to reduce or prevent graft versus host reactions. This is done by knocking out the ability of the T-cell receptors to activate the T-lymphocyte. When a dominant CD3 epsilon chain mutant is introduced to the T-lymphocyte it can knockout the ability of the T-cell receptors to activate the T-lymphocyte. One such CD3 epsilon mutant is a double mutant that replaces the Cysteine residues of the C-X-X-C motif with Serine residues (a C119S and C122S mutant). This mutant CD3 epsilon chain disrupts signaling from the T-cell receptor and prevents ligand induced activation of the T-lymphocyte through the T-cell receptor. By expressing an excess of the CD3 epsilon C119S/C122S mutant in a T-lymphocyte, the T-lymphocyte will not activate in response to host antigens binding to the T-lymphocyte receptor of the CAR T-lymphocytes. This allows the use of allogenic CAR T-lymphocytes in a subject with reduced graft versus host reactions.

In an aspect, an expression vector has a CAR cassette and a CD3 epsilon mutant (a dominant mutant such as C119S/C122S) cassette. These two expression cassettes are operably linked to a strong promoter (e.g., with a strong enhancer active in T-lymphocytes). The two cassettes can have different promoters or can be expressed from the same promoter. The expression construct can also include a transgene under control of a different promoter, which transgene is operably linked to a RDE that activates transgene expression upon stimulation of the cell by the CAR.

In an aspect, Tox expression in a T-lymphocyte or T-cell is regulated to produce either an effector state (low Tox) or an exhausted state ($T_{ex}$ with high Tox). Tox can be down regulated in activated T-lymphocytes with a miRNA, siRNA or antisense RNA targeted at Tox. The Tox locus in an engineered T-lymphocyte can also be knocked out so that it does not produce a functional product. Conversely, Tox can be expressed in an engineered T-lymphocyte to exhaust the cell and turn it off (an off switch).

BRIEF DESCRIPTION OF THE DRAWINGS

FIG. 1 shows a diagram for optimal CAR activity where the three variables are CAR copy number, target epitope copy number and CAR binding affinity.

FIG. 2 shows a graph for the bioluminescence from T-cells with luciferase controlled by an RDE following activation of the T-cell by Raji target cells (activate CAR) or by CD3/CD28 beads (activate TCR) as compared to bioluminescence of T-cells at resting.

FIG. 3 shows a graph for bioluminescence from T-cells with luciferase controlled by the RDEs Gold1, Gold2, or Gold3 following activation of the T-cell by Raji target cells (activate CAR) as compared to bioluminescence of T-cells at resting.

FIG. 4 shows a graph for the IL-12 expression from T-cells with IL-12 expression controlled by an RDE following activation of the T-cell by Raji target cells (activate CAR) as compared to IL-12 expression of T-cells at resting.

FIG. 5 shows basal luciferase expression and activated luciferase expression for luciferase constructs utilizing different RDEs as control elements in Jurkat cells.

DETAILED DESCRIPTION OF THE INVENTION

Figure 1:
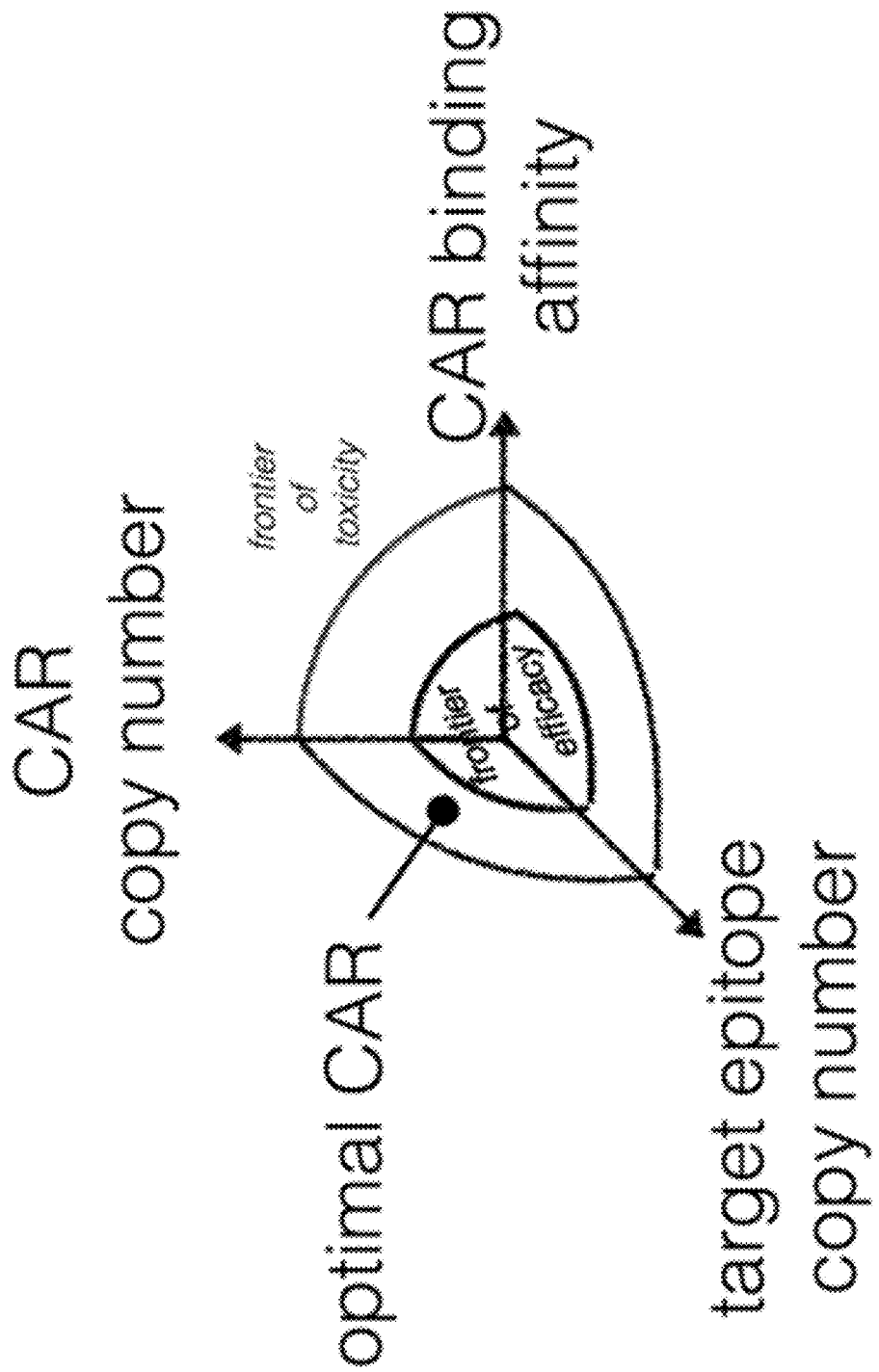

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 µg, it is intended that the concentration be understood to be at least approximately or about 10 µg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, an "actuator element" is defined to be a domain that encodes the system control function of the RNA control device. The actuator domain can optionally encode the gene-regulatory function.

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multi-specific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or can be a macromolecule besides a polypeptide. Such a biological sample can include, but is not limited to a tissue sample, a tumor sample, a cell or a fluid with other biological components.

As used herein, the terms "Chimeric Antigen Receptor" and the term "CAR" are used interchangeably. As used herein, a "CAR" is defined to be a fusion protein comprising antigen recognition moieties and cell-activation elements.

As used herein, a "CAR T-cell" or "CAR T-lymphocyte" are used interchangeably, and are defined to be a T-cell containing the capability of producing CAR polypeptide, regardless of actual expression level. For example a cell that is capable of expressing a CAR is a T-cell containing nucleic acid sequences for the expression of the CAR in the cell.

As used herein, a "costimulatory element" or "costimulatory signaling domain" or "costimulatory polypeptide" are defined to be the intracellular portion of a costimulatory polypeptide. A costimulatory polypeptide can be represented in the following protein families: TNF receptor proteins, Immunoglobulin-like proteins, cytokine receptors, integrins, signaling lymphocytic activation molecules (SLAM proteins), and activating natural killer cell receptors. Examples of such polypeptides include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, MyD88, and the like.

As used herein, a "Cmax" is defined to mean the maximum concentration of a polypeptide produced by a cell after the cell is stimulated or activated to produce the polypeptide.

As used herein, a "cytokine $C_{max}$" is defined to mean the maximum concentration of cytokine produced by an immune cell after stimulation or activation to produce the cytokine.

As used herein, a "cytotoxic polypeptide $C_{max}$" is defined to mean the maximum concentration of cytotoxic polypeptide produced by an immune cell after stimulation or activation to produce the cytotoxic polypeptide.

As used herein, an "effective amount" or "therapeutically effective amount" are used interchangeably, and defined to be an amount of a compound, formulation, material, or composition, as described herein effective to achieve a particular biological result.

As used herein, an "epitope" is defined to be the portion of an antigen capable of eliciting an immune response, or the portion of an antigen that binds to an antibody. Epitopes can be a protein sequence or subsequence that is recognized by an antibody.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will be an expression vector or expression construct.

As used herein, an "extracellular element" is defined as the antigen binding or recognition element of a Chimeric Antigen Receptor.

As used herein, a "hematopoietic cell" is defined to be a cell that arises from a hematopoietic stem cell. This includes but is not limited to myeloid progenitor cells, lymphoid progenitor cells, megakaryocytes, erythrocytes, mast cells, myeloblasts, basophils, neutrophils, eosinophils, macrophages, thrombocytes, monocytes, natural killer cells, T lymphocytes, B lymphocytes and plasma cells.

As used herein, "heterologous" is defined to mean the nucleic acid and/or polypeptide are not homologous to the host cell. For example, a construct is heterologous to a host cell if it contains some homologous sequences arranged in a manner not found in the host cell and/or the construct contains some heterologous sequences not found in the host cell.

As used herein "hnRNPLL" is defined to mean heterogeneous nuclear ribonucleoprotein L like.

As used herein, an "intracellular element" is defined as the portion of a Chimeric Antigen Receptor that resides on the cytoplasmic side of the eukaryotic cell's cytoplasmic membrane, and transmits a signal into the eukaryotic cell. The "intracellular signaling element" is that portion of the intracellular element which transduces the effector function signal which directs the eukaryotic cell to perform a specialized function.

As used herein, a "knottin" or "inhibitor cystine-knots" or "cysteine-knot" are a structural family of ultra-stable peptides with diverse functions. Knottins contain three disulfide bonds connected in a particular arrangement that endows these peptides with high thermal, proteolytic, and chemical stability. Knottins have a core scaffold structure with peptide loops that can confer binding specificity to the peptide. Knottins have been engineered to introduce diversity into the loops to create binding specificity for desired targets.

As used herein, "RNA destabilizing element" or "RDE" are used interchangeably and both are defined as a nucleic acid sequence in an RNA that is bound by proteins and which protein binding changes the stability and/or translation of the RNA. Examples of RDEs include Class I AU rich elements (ARE), Class II ARE, Class III ARE, U rich elements, GU rich elements, and stem-loop destabilizing elements (SLDE). Without wishing to be bound by theory, RDE's may also bind RNA stabilizing polypeptides like HuR.

As used herein, a "single chain antibody" (scFv) is defined as an immunoglobulin molecule with function in antigen-binding activities. An antibody in scFv (single chain fragment variable) format consists of variable regions of heavy ($V_H$) and light ($V_L$) chains, which are joined together by a flexible peptide linker.

As used herein, a "T-lymphocyte" or T-cell" is defined to be a hematopoietic cell that normally develops in the thymus. T-lymphocytes or T-cells include, but are not limited to, natural killer T cells, regulatory T cells, helper T cells, cytotoxic T cells, memory T cells, gamma delta T cells and mucosal invariant T cells.

As used herein, "Tox" is defined to mean thymocyte selection associated high mobility group box.

As used herein, "transfected" or "transformed" or "transduced" are defined to be a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

As used herein, a "transmembrane element" is defined as the element between the extracellular element and the intracellular element. A portion of the transmembrane element exists within the cell membrane.

Combination Therapies

This disclosure provides compositions and methods for providing a CAR T-lymphocyte expressing a transgene under the control of an RDE in combination or in an order of succession with another therapy. The other therapy can include, for example, a chemotherapeutic, an antibody, and antibody-drug conjugate, a radiotherapy, an alkylating agent, a plant alkaloid, an antitumor antibiotic, an antimetabolite, a topoisomerase inhibitor, and/or an anti-neoplastic. For example, the other therapy can be an antibody drug conjugate that has the same or different specificity as the CAR T-lymphocyte.

Antibodies and antibody-drug conjugates (ADC) can bind to a tumor associated antigen, including, for example, any of the tumor associate antigens described herein as targets for a CAR. The drug component of the ADC can be, for example, a chemotherapeutic, a radionucleotide, an alkylating agent, a plant alkaloid, an antitumor antibiotic, an antimetabolite, a topoisomerase inhibitor, and/or an anti-neoplastic. The drug component of the ADC can be attached to the antibody through a linker which can be cleavable or non-cleavable in nature.

Alkylating agents can include, for example, mustard gas derivatives (e.g., mechlorethamine, cyclophosphamide, chlorambucil, melphalan, or ifosfamide), ethylenimines (e.g., thiotepa or hexamethylmelamine), alkylsulfonates (e.g., busulfan), hydrazines and triazines (e.g., altretamine, procarbazine, dacarbazine, or temozolomide), nitrosoureas (e.g., carmustine, lomustine or streptozocin), and metal salts (e.g., carboplatin, cisplatin, or oxaliplatin). Plant alkaloids can include, for example, *Vinca* alkaloids (e.g., vincristine, vinblastine, or vinorelbine), taxanes (e.g., paclitaxel or docetaxel), podophyllotoxins (e.g., etoposide or tenisopide), and camptothecan analogs (e.g., irinotecan or topotecan). Antitumor antibiotics can include, for example, anthracyclines (e.g., doxorubicin, daunorubicin, epirubicin, mixoantrone, or idarubicin), and chromomycins (e.g., dactinomycin or plicamycin). Antimetabolites can include, for example, folic acid antagonists (e.g., methotrexate), pyrimidine antagonists (e.g., 5-flurouracil, foxuridine, cytarabine, capecitabine, or gemcitabine), purine antagonists (e.g., 6-mercaptopurine or 6-thioguanine), and adenosine deaminase inhibitors (e.g., cladribine, fludarabine, nelarabine, or pentostatin). Topoisomerase inhibitors can include, for example, topoisomerase I inhibitors (e.g., irinotecan or topotecan) and topoisomerase II inhibitors (e.g., amsacrine, etoposide, etoposide phosphate, or tenipside). Anti-neoplastics can include, for example, ribonucleotide reductase inhibitors (e.g., hydroxyurea), adrenocortical steroid inhibitors (e.g., mitotane), enzymes (e.g., asparaginase or pegaspargase), antimicrotubule agents (e.g., estramustine), and retinoids (e.g., bexarotene, isotretinoin, or tretinoin).

The drug component can also be an anthracycline, a camptothecin, a tubulin inhibitor, a maytansinoid, a calicheamycin, a pyrrolobenzodiazepine dimer (PBD), an auristatin, a nitrogen mustard, an ethylenimine derivative, an alkyl sulfonate, a nitrosourea, a triazene, a folic acid analog, a taxane, a COX-2 inhibitor, a pyrimidine analog, a purine analog, an antibiotic, an enzyme inhibitor, an epipodophyllotoxin, a platinum coordination complex, a *vinca* alkaloid, a substituted urea, a methyl hydrazine derivative, an adrenocortical suppressant, a hormone antagonist, an antimetabolite, an alkylating agent, an antimitotic, an anti-angiogenic agent, a tyrosine kinase inhibitor, an mTOR inhibitor, a heat shock protein (HSP90) inhibitor, a proteosome inhibitor, an HDAC inhibitor, a pro-apoptotic agent, and a combination thereof.

Specific drugs of use may be selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyanomorpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839. Preferably, the drug is SN-38.

In an aspect the combination therapy is a protein conjugate. The protein conjugate can carry a payload that can be a therapeutic, diagnostic, or a reporter. A single molecule of the therapeutic, diagnostic or reporter may be present or two or more molecules may be present. The therapeutic can be a chemotherapeutic including, for example, any of those described herein such as a radionucleotide, an alkylating agent, a plant alkaloid, an antitumor antibiotic, an antimetabolite, a topoisomerase inhibitor, and/or an anti-neoplastic. The payload of the conjugate can be any one or more of these therapeutics, diagnostics and/or reporters. The protein can be a fragment, a monomer, a dimer, or a multimeric protein. The protein can be an antibody, an antibody fragment or derivative, a single chain antibody, an enzyme, cytokine, chemokine, receptor, blood factor, peptide hormone, toxin, and/or transcription factor.

Many conjugating reagents can be used to conjugate a payload to a protein. Such reagents may contain at least one functional group capable of reacting with a protein or peptide. For example, the conjugating reagent may comprise a functional group capable of reacting with at least one electrophile or, especially, nucleophile, present in the protein, the functional group being attached to the payload via the linker. Any type of known conjugation reaction may be used to form the conjugate. For example, the reaction can be carried out using the known methods of thiol bonding, amine conjugation, or click chemistry. The reagent may contain a maleimide group, an N-hydroxysuccinimide group, a click-chemistry group, for example an azide or alkyne group, an amine group, a carboxyl group, a carbonyl group, or an active ester group. Other possible approaches include the use of proteins that have been recombinantly engineered with an amino acid specifically for conjugation such as engineered cysteines or non-natural amino acids, and enzymatic conjugation through a specific enzymatic reaction such as with transglutaminase. The reaction site on the protein may be either nucleophilic or electrophilic in nature. Common protein conjugation sites are at lysine or cysteine amino acid residues or carbohydrate moieties. Alternatively, conjugation may occur at a polyhistidine tag which has been attached to a binding protein.

A conjugating reagent can be advantageously capable of reacting with a nucleophile in a protein and hence becoming chemically bonded thereto. In these examples, the conjugating reagent typically includes at least one leaving group which is lost on reaction with a nucleophile. The conjugating reagent may, for example, include two or more leaving groups. The conjugating reagent can be capable of reacting with two nucleophiles. The conjugating reagent can comprise at least two leaving groups. When two or more leaving groups are present, these may be the same or different. Alternatively, a conjugating reagent may contain a single group which is chemically equivalent to two leaving groups and which single group is capable of reacting with two nucleophiles. Nucleophilic groups include, for example, sulfur atoms and amine groups, and nucleophilic groups in proteins are for example provided by cysteine, lysine or histidine residues. Nucleophilic groups can be a sulfur atom present in a cysteine residue of a protein. Such structures may be obtained by reduction of a disulfide bond in the protein. The nucleophilic group may be an imidazole group in a histidine residue of the protein, e.g., as present in a polyhistidine tag.

The conjugates can contain a linker which connects the therapeutic, diagnostic or labelling agent to the protein or peptide in the conjugate. The backbone of the linker can be a continuous chain of atoms which runs from the therapeutic, diagnostic or labelling agent at one end to the protein or peptide at the other end. The linker may contain a degradable group, i.e. it may contain a group which breaks under physiological conditions, separating the payload from the protein to which it is, or will be, bonded. Alternatively, the linker is not cleavable under physiological conditions. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited).

Where the linker contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. The degradable linker can also be an acid-cleavable linker or a reducible linker. The reducible linker may comprise a disulfide group. The linker may also contain a group which is susceptible to enzymatic degradation, for example it may be susceptible to cleavage by a protease (e.g. a lysosomal or endosomal protease) or peptidase. For example, it may contain a peptidyl group comprising at least one, for example at least two, or at least three amino acid residues (e.g. Phe-Leu, Gly-Phe-Leu-Gly, Val-Ala, Val-Cit, Phe-Lys, Glu-Glu-Glu). For example, it may include an amino acid chain having from 1 to 5, for example 2 to 4, amino acids. The enzyme cleavable linker can also comprise a chemical group which can be cleaved or degraded by one or more lysosomal enzymes. Suitable groups include, for example, a valine-citrulline dipeptide group, a phenylalanine-lysine dipeptide group, and a β-glucuronide group.

When the protein in the protein conjugate is an antibody (e.g., full length, fragment, and/or single chain) one end of the first linker can be covalently attached to the antibody. The antibody-reactive end of the linker can be a site that is capable of conjugation to the antibody through a cysteine thiol or lysine amine group on the antibody, and so can be a thiol-reactive group such as a double bond (as in maleimide) or a leaving group such as a chloro, bromo, or iodo, or an R-sulfanyl group, or an amine-reactive group such as a carboxyl group.

The CAR therapy (e.g., with a GOLD-controlled transgene) and the other therapy can be provided to a subject at the same time, or one can be provided to the subject before the other, or the CAR therapy and the other therapy can be provided in alternating cycles, or the CAR therapy together with the other therapy can be provided in cycles, or other combinations of administration can be used. The CAR therapy can be combined with an antibody conjugate (ADC) therapy where the CAR and the ADC bind to the same antigen or bind to different antigens. When the CAR and ADC bind to the same antigen, the CAR and the ADC can bind to the same or different epitopes on the antigen. One of the ADC or the CAR therapy can be provided to the subject first, and followed by the other after a period of treatment with the first. The ADC, either alone or in combination with another approved therapy (e.g. chemotherapy and/or immune checkpoint inhibitors) can be provided to the subject first to reduce the tumor burden in the subject prior to the administration of the CAR therapy. Alternatively, the ADC and CAR therapy can be provided to the subject at the same time. Or the CAR therapy can be provided first followed by the ADC therapy.

RNA Destabilizing Elements

RNA destabilizing elements (RDE) are nucleic acids that affect or maintain the stability of an RNA molecule or the translation kinetics of an RNA molecule. Some RDEs are bound by polypeptides which destabilize (e.g., cleave) the RNA, or prevent translation, leading to loss of function for the RNA. Some RDE binding polypeptide stabilizes the RNA increasing the half-life of the RNA. RDEs can be used to control the expression of a transgene, e.g., a transgene encoding a chimeric antigen receptors. RDEs can be used with RNA control devices, DEs, and/or Side CARs to regulate the expression of a transgene. The RDEs can also be used to control expression of transgenes encoding polypeptides other than a CAR. Other transgenes may encode, for example, a cytokine, an antibody, a checkpoint inhibitor, a granzyme, an apoptosis inducer, complement, a cytotoxic small molecule, other cytotoxic compounds, a polypeptide for imaging, or other polypeptide that can have a desired effect. The RDE can control the delivery of a transgene payload. Examples of RDEs include, for example, AU rich elements, U rich elements, GU rich elements, and certain stem-loop elements. Exemplary RDEs are described in Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gki1012 (2006); Meisner et al., ChemBioChem 5:1432-1447 (2004); Guhaniyogi et al., Gene 265:11-23 (2001), all of which are incorporated by reference in their entirety for all purposes.

The RDE can be a Class I AU rich element (dispersed AUUUA (SEQ ID NO:1) in U rich context), a Class II AU rich element (overlapping $(AUUUA)_n$), a Class III AU rich element (U-rich stretch), a stem-loop destabilizing element (SLDE), a cytokine 3' UTR (e.g., INF-γ, IL-2, T-cell receptor a chain, TNFα, IL-6, IL-8, GM-CSF, G-CSF etc.), and a sequence of AUUUAUUUAUUUA (SEQ ID NO: 2). Khabar, WIREs RNA 2016, doi: 10.1002/wrna.1368 (2016); Palanisamy et al, J. Dent. Res. 91:651-658 (2012), both of which are incorporated by reference in their entirety for all purposes. The RDE can also be a GU rich element comprised of one or more of, for example, UUGUU (SEQ ID NO: 3), UGGGGAU (SEQ ID NO: 4), or GUUUG (SEQ ID NO: 5). The RDE can be a U-rich element comprised of one or more of, for example, UUUGUUU (SEQ ID NO: 6), U (SEQ ID NO: 7), UUUAUUU (SEQ ID NO: 8), UUU-GUUU (SEQ ID NO: 9), UUAGA (SEQ ID NO: 10), or AGUUU (SEQ ID NO: 11). In some aspects, multiple RDEs can be combined to make a regulatory unit, for example, multiple RDEs that have the same sequence can be arranged in a concatemer or can be arranged with intervening sequence in between some or all of the RDEs. The RDE sequence can be modified to increase or decrease the affinity of an RNA binding protein(s) for the RDE. For example, an AU rich RDE can be changed to alter the affinity of glyceraldehyde phosphate dehydrogenase (GAPDH) to the RDE. This change in affinity can alter the GAPDH-activation threshold for expression of a transgene regulated by the RDE to which GAPDH binds.

The disclosure assigns AU #designations to some RDEs and these RDEs can be referred to by the AU #or the gene name from which the RDE is derived. Some AU #s and the corresponding gene from which the RDE is derived include, for example, AU 1 (CD40LG), AU 2 (CSF2), AU 3 (CD247), AU 4 (CTLA4), AU 5 (EDN1), AU 6 (IL2RA), AU 7 (SLC2A1), AU 8 (TRAC), AU 9 (CD274), AU 10 (Myc), AU 11 (CD19), AU 12 (IL4), AU 13 (IL5), AU 14 (IL6), AU 15 (IL9), AU 16 (IL10), AU 17 (IL13), AU 18 (FOXP3), AU 19 (TMEM-219), AU 20 (TMEM-219snp), AU 21 (CCR7), AU 22 (SEM-A4D), AU 23 (CDCl42-SE23), AU 24 (CD8), AU 27 (bGH), and AU 101 (IFNg).

The RDE can be from the 3' UTR of a gene encoding, for example, IL-1, IL-2, IL-3, IL-4, IL-6, IL-8, IL-10, GM-CSF, G-CSF, VEGF, $PGE_2$, COX-2, MMP (matrix metalloproteinases), bFGF, c-myc, c-fos, betal-AR, PTH, interferon-gamma, MyoD, p21, Cyclin A, Cyclin B1, Cyclin D1, PAI-2, NOS HANOS, TNF-alpha, interferon-alpha, bc1-2, interferon-beta, c-jun, GLUT1, p53, Myogenin, NF-M, or GAP-43, lymphocyte antigen 96, SUPV3L1, SFtPA2, BLOC1S2, OR10A6, OR8D1, TRPT1,CIP29, EP400, PLE2, H3ST3A1, ZNF571, PPP1R14A, SPAG4L, OR10A6 and KIR3DL. Other RDEs are found in, for example, the 3'-UTRs from GLMN, AMY2B, AMY2A, AMY2A, AMY1A, TRIM33, TRIM33, TRIM33, CSRP1, PPP1R12B, KCNH1, Reticulon 4, MRPL30, Nav1.2, Tissue_factor_pathway_inhibitor, EEF1B2, CRYGB, ARMC9, RPL15, EAF2, MRPS22, MRPS22, COPB2, PDCD10, RE1-silencing_transcription_factor, Amphiregulin, AP1AR, TLR3, SKP2, Peptidylglycine_alpha-amidating_monooxygenase, TNFAIP8, Interleukin 9, PCDHA2, PCDHA12, Aldehyde_dehydrogenase_5_family, _member_A1, KCNQ5, COX7A2, Monocarboxylate_transporter_10, MLLT4, PHF10, PTPN12, MRNA_(guanine-N7-)-methyltransferase, WHSC1L1, Tricho-rhino-phalangeal_syndrome_Type_1, Interferon alpha-1, ZCCHC6, Retinitis_pigmentosa_GTPase_regulator, MED14, CLCN5, DNA2L, OR52D1, NELL1, SLC22A25, SLC22A10, TRPC6, CACNA2D4, EPS8, CT2 (gene), Mitochondrial_ribosomal_protein_L42, TAOK3, NUPL1, Endothelin_receptor_type_B, Survival_of_motor_neuron_protein-interacting_protein_1, POLE2, Hepatic_lipase, TPSG1, TRAP1, RPS15A, HS3ST3A1, CROP_(gene), Apolipoprotein_H, GRB2, CEP76, VPS4B, Interleukin_28B, IZUMO1, FGF21, PPP1R15A, LIN7B, hnRNPLL, Tox, and CDCl45-related_protein.

Still other RDEs can be found in, for example, the 3'UTRs of SCFD1, MAL2, KHSRP, IQCB1, CAMP responsive element modulator, MFAP5, SBF2, FKBP2, PDCD10, UBE2V2, NDUFAB1, Coiled-Coil Domain Containing Protein, ALG13, TPTE, Enaptin, Thymopoietin, Delta-like_1, C11orf30, Actinin_alpha_4, TMEM59, SP110, Dicer, TAR-DBP, IFNA17, IFNA16, IFNA14, ZMYM3, Interleukin_9_type_I, OPN1SW, THSD1, ERGIC2, CAMK2B, WDR8, FXR1, Thymine-DNA glycosylase, Parathyroid hormone-related_protein, OSBPL3, Ran, GYPE, AKAP4, LOC642658, L2HGDH, AKAP1, Zinc_finger_protein 334, TC2N, FKBPL, GRB14, CXorf67, CXorf66, CEP76, Gastricsin, CEP70, CYP26A1, NAA35, Aryl hydrocarbon receptor nuclear translocator, KLC4, GPR112, LARP4, NOVA1, UBE2D3, ITGA6, GPR18, MGST_type_A, RE1-silencing_transcription_factor, ASPM, ZNF452, KIR2DS4, AHSA1, TMTC4, VSX1, P16, MRPL19, CCL20, TRPT1, Hepatic_lipase, PDLIM5, CCDC153,'CCDC55, GAPVD1, HOXB2, KCNQ5, BRCC3, GTF2IRD1, CDK5RAP3, Transcription_factor_II_B, ZEB1, IRGM, SLC39A6, RHEB, PSIP1, RPS6KA5, Uro-kinase_receptor, GFM1, DNAJC7, Phosphoinositide-dependent_kinase-1, LMOD3, TTC35, RRP12, ATXN2, ACSM3, SOAT1, FGF8, HNRPH3, CTAGE5, POLG2, DYRK3, POLK, Cyclin-dependent_kinase inhibitor 1C, CD137, Calmodulin_1, ZNF571, CNOT2, CRYZL1, SMC3, SMC4, SLC36A1, Decorin, HKR1, ERC1, S100A6, RIMS1, TMEM67, Mitochondrial_ribosomal_protein_L42, MECP2, RNF111, SULT1A1, MYLK3, TINAG, PRKAR1A, RGPD5, UBE2V1, SAR1B, SLC27A6, ZNF638, RAB33A, TRIOBP, MUCL1, CADPS2, MCF2L, TBCA, SLC17A3, LEO1, IFNA21, RUNX1T1, PRKD2, ATP11B, MORC2, RBM6, KLRD1, MED31, PPHLN1, HMGB2, DNA_repair_and_recombination_protein_RAD54-like, RBM9', ARL11, HuD, SPEF2, CBLL1, SLC38A1, 'Caspase_1', S100G, CA1_, CELA1, PTS, ITM2B, Natriuretic_peptide_precursor_C, TRPP3, IMPDH2, DPYS, CDCA3, EFCAB6, SLIT2, SIPA1L1, FIP1L1, ATP6V1B2, HSD17B4, HSD17B7, NDUFC1, CROP, CD48, APPBP1, CD44, CD46, Histone_deacetylase_2_type_XI, Interleukin 4, Tricho-rhino-phalangeal_syndrome_Type_1, SEC61G, TR1P12, PLEKHO1, SEC61B, ST6GALNAC1, CPVL, E2F7, UTP20, E2F5, PARD3, EXOC7, HEXB, Caspase_recruitment_domain-containing_protein 8, MBD4, PPP4C, Helicase, Phosducin, SPG11, CGGBP1, PSKH1, Cathepsin_S, orexin, IMMP2L, C2orf28, Laminin, EIF3S6, LRRC41_type_XII, Cathepsin_C, HPS6, ARAF, Zinc_finger_and_BTB_domain-containing_protein_16, Sex_hormone-binding_globulin, FBLN2, Suppressor_of_cytokine_signaling_1, TMEM126A, DOM3Z, TSFM_POLQ-like, DYNLT3, CDH9, EAF2, MIPEP, NDUFA12, HDAC8, MKKS, FGG, IL36G, CDCA7, CRISPLD2, Olfactomedin-like_2b, MRPL32, MRPL33, AHI1, SMARCAL1, UTP14A, SSH2, Dystonin, Contactin_6, PPFIBP1, THOC1, CNOT1, RHCE, SLC41A3, SLC2A9, SNAP23, RFX3, GNG4, MRPL40, LSR, Angiogenin, TRIP4, VRK1, COUP-TFII, FOXP2, SNX2, Nucleoporin_85, RPL37A, RPL27A, SEC62, Calcium-activated_potassium_channel_subunit_alpha-1, SMARCE1, RPL17, CEP104, CEP290, VPS29, ANXA4, Zinc_finger_protein_737, DDX59, SAP30, NEK3, Exosome_component_9, Receptor_for_activated_C_kinase_1, Peptidylprolyl_isomerase_A, TINP1, CEACAM1, DISC1, LRRTM1, POP1_Lamin_B1, SREBP_cleavage-activating_protein, COX6C, TLR_1, ARID2, LACTB, MMS22L, UBE2E3, DAP3, ZNF23, SKP2, GPR113, IRF9 Ghrelin_O-acyltransferase, NEIL3, EEF1E1, COX17, ESD_, Dentin_sialophosphoprotein, HDAC9, RFC4, CYLD, RPLP0, EIF2B3, UGT2A1, FABP7, TRIP11, PLA2G4A, AKR1C3, INTS12, MYH1, ZBTB17, MYH4, NLRP2, MECOM, MYH8, Thermogenin_receptor_2, IFI16, THYN1, RAB17, ETFA, Cystic_fibrosis_transmembrane_conductance_regulator, F13B, RAB6A, ST8SIA1, SATB2, SATB1, HMG20B, UHRF1, CNOT3, Prostaglandin_EP2_receptor, FAM65B, Peroxisome_proliferator-activated_receptor_gamma, KvLQT2, GRIK5, SHOC2, Cortactin, FANCI, KIAA1199, Kynureninase, Decoy_receptor_1, NEU3, PHF10, Methyl-CpG-binding_domain_protein_2, RABGAP1, CEP55, SF3B1, MSH5, MSH6, CREB-binding_protein, LIMS1, SLC5A4, CCNB1IP1, RNF34, SORBS2, UIMC1, SOX5, YWHAZ, ICOSLG, NOP58, Zinc_finger_protein 679, PHKB, MED13, ABCB7, COQ9, C14orf104, Zinc_finger_protein_530, KLRC2, LSM8, NBR1, PRKCD, Long-chain-aldehyde_dehydrogenase, MTSS1, Somatostatin, Ubiquitin_carboxyl-terminal_hydrolase_L5, WDR72, FERMT3, Nuclear_receptor_related-1_protein, Citrate_synthase, VPS11, KIZ, ZFYVE27, BCKDHB, Hypocretin, CACNG2, PTCH1, Carbonic_anhydrase_4, Nucleoporin_107, LDL_receptor, LEKTI, FBXO11, NDUFB3, FCHO2, CEP78, RAPGEF6, PPIL3, NIN, RAPGEF2, Growth_hormone_1, Growth_hormone_2, MNAT1, Nav1, MAP3K8, SUGT1, LAIR1, Hyaluronan-mediated_motility_receptor, MAP3K2, MPP2, TFB2M, CRB3, MPP5, CACNA1G, DLGAP2, INHBA, MAGI2, CIP29, SETDB1, Cytochrome_b5, TRPV2, Interleukin_1_receptor, HOXD8, TIMM10, ATXN2L, CLCN2, CREB1, TNIP1, CBLB, Factor_V, USP33, SON, RBBP8, SLC22A18, PTPN12, ADCY8, MYLK, KIF23, REXO2, BST1, TOP3B, COPB1, AXIN2, COPB2, TNRC6B, Guanidinoacetate_N-methyltransferase, Acyl-CoA_thioesterase_9, C4orf21, TSHB, FRS3, EPB41, Cyclin_T2, LAIR2, Nucleoporin_43, APLP2, TNFRSF19, Death-associated_protein_6, Epithelial_cell_adhesion_molecule, CLEC7A, Gephyrin, CLDND1, VPS37A, PCDHAC2, Bone_morphogenetic_protein_4, NVL, RBM33, RNF139, Sperm_associated_antigen_5, PLCB1, Glial_cell_line-derived_neurotrophic_factor, PARP4, PARP1, MAN2A1, Bone_morphogenetic_protein_1, PAX4, BCCIP, MMPI, Decoy_receptor_3, RAMP2, NCAPD3, LRRC37A, RWDD3, UBE2A, UBE2C, SLC3A1, MRPS22, CDC14A, ITSN1, POLE2, MYC-induced_nuclear_antigen, TMLHE, Glutamate_carboxypeptidase_II, GPR177, PPP2R5C, KIAA1333, RPP38, MYO1F, Farnesoid_X_receptor, Caldesmon, FBXO4, FBXO5, OPN1MW, PIGN, ARNTL2, BCAS3, C6orf58, PHTF2, SEC23A, NUFIP2, OAZ1, Osteoprotegerin, ANAPC4, ATP6V0A2, SPAM1, PSMA6, TAS2R30, RABEP1, DPM3, SLC6A15, RPS26, RPS27, RPS24, RPS20, RPS21, ARHGAP24, Catechol-O-methyl transferase, ERCC5, Transcription_initiation_protein_SPT3 homolog, OR1E1, ZNRF1, GMEB1, CCT2_GNAQ, Mucin_6, Mucin_4, LRP5, PDE9A, C2orf3, EZH2, Epidermal_growth_factor_receptor, TMTC2, PDE4A, EPH_receptor_A4, PPIB, DENND4A, ANTXR1, ANTXR2, Nucleoporin_88, SLCO1B3, COG8, RBMS1, MAP7, HIST2H2BE, AEBP2, DCLRE1A, RPL24, HNRPA2B1, RPL21, RPL23, MAPKAP1, NIPBL, ATG7, SERPINI2, GYLTL1B, ATP5G2, DIP2A, AMY2A, CEP63, TDRD7, PIEZO1, CLDN20, GRXCR1, PMEL, NIF3L1, MCC_, PCNX, TMBIM4, DUSP12, ZMYND8, GOSR1, Interferon_gamma_receptor_1, LDB3, PON3, C1D, ABCC8, COQ7, COQ6, AMELY, HAVCR1, PICALM, Sjogren_syndrome_antigen_B, PLK4, HBB, AKT1, PCDHGB7, C6orf10, UBR1, Retinoblastoma-like_protein_1, GRK6, WWC2, GRK4, INPP4B, SLC34A1, GOLGA2, MYCBP2, PTP4A2, NUCB2, MAGOH, RPP40, Alpha-2A_adrenergic_receptor, SPAG11B, Nucleoporin_205, COG1, Motile_sperm_domain_containing_3, KCNMB3, Motile_sperm_domain_containing_1, KLHL7, KCNN2, TSPAN8, GPR21, Translocator_protein, HNRNPLL, ABHD5, CAB39L, Amphiregulin, GPR1, Interleukin_18, EIF4G3, Interleukin_15, CCDCl80, CD2AP, NFS1, GRB2, ULBP2, Vascular_endothelial_growth_factor_C, RPS3, TLR8, BCL2-related_protein_A1, RHOT1, Collagen, Centromere_protein_E, STMN2, HESX1, RPL7, Kalirin, PCMT1, HLA-F, SUMO2, NOX3, EP400, DNM3, EED, NGLY1, NPRL2, PLAC1, Baculoviral_IAP_repeat-containing_protein_3, C7orf31, TUBA1C, HAUS3, IFNA10, MYST4, DCHS1, SIRT4, EFEMP1, ARPC2, MED30, IFT74, PAK1IP1, DYNC1LI2, POLR2B, POLR2H, KIF3A, PRDM16, PLSCR5, PEX5, Parathyroid_hormone_1_receptor, CDCl23, RBPMS, MAST1, NRD1, BAT5, BAT2, Dock11, GCSH, POF1B, USP5, POT1, MUTYH, CYP2E1, FAM122C, A1_polypeptide, Flavin_containing_monooxygenase_3, HPGD, LGALS13, MTHFD2L, Survival_motor_neuron_domain_containing_1, PSMA3, MRPS35, MHC_class_I_polypeptide-related_sequence_A, SGCE, REPS1, PPP1R12A, PPP1R12B, PABPC1, MAPK8, PDCD5, Phosphoglucomutase_3, Ubiquitin_C, GABPB2, Mitochondrial_translational_release_factor_1, PFDN4, NUB1, SLC13A3, ZFP36L1, Galectin-3, CC2D2A, GCA, Tissue_factor_pathway_inhibitor, UCKL1, ITFG3, SOS1, WWTR1, GPR84, HSPA14, GJC3, TCF7L1, Matrix_metallopeptidase 12, ISG20, LILRA3, Serum_albumin, Phosducin-like, RPS13, UTP6, HP1BP3, IL12A, HtrA_serine_peptidase_2, LATS1, BMF_, Thymosin_beta-4, B-cell_linker, BCL2L11, Coagulation_factor_XIII, BCL2L12, PRPF19, SFRS5, Interleukin_23_subunit_alpha, NRAP, 60S_ribosomal_protein_L14, C9orf64, Testin, VPS13A, DGKD, PTPRB, ATP5C1, KCNJ16, KARS, GTF2H2, AMBN, USP13, ADAMTSL1, TRO_, RTF1, ATP6V1C2, SSBP1, SNRPN_upstream_reading_frame_protein, RPS29, SNRPG, ABCC10, PTPRU, APPL1, TINF2, TMEM22, UNC45A, RPL30, PCDH7, Galactosamine-6_sulfatase, UPF3A, ACTL6A, ACTL6B, IL3RA, SDHB, Cathepsin_L2, TAS2R7, Cathepsin_L1, Pituitary_adenylate_cyclase-activating_peptide, RPN2, DYNLL1, KLK13, NDUFB3, PRPF8, SPINT2, AHSA1, Glutamate_carboxypeptidase_II, DRAP1, RNASE1, Olfactomedin-like_2b, VRK1, IKK2, ERGIC2, TAS2R16, CAMK2G, CAMK2B, Estrogen_receptor_beta, NADH_dehydrogenase, RPL19, NUCB2, KCTD13, ubiquinone, H2AFY, CEP290, PABPC1, HLA-F, DHX38, KIAA0922, MPHOSPH8, DDX59, MIB2, ZBP1, C16orf4, UACA, C6orf142, MRPL39, Cyclin-dependent_kinase_7, Far_upstream_element-binding_protein_1, SGOL1, GTF2IRD1, ATG10, Dermcidin, EPS8L2, Decorin, Nicotinamide_phosphoribosyltransferase, CDC120, MYB, WNT5A, RBPJ, DEFB103A, RPS15A, ATP5H, RPS3, FABP1, SLC4A8, Serum_amyloid_P_component, ALAS1, MAPK1, PDCD5, SULT1A1, CHRNA3, ATXN10, MNAT1, ALG13, Ataxin_3, LRRC39, ADH7, Delta-sarcoglycan, TACC1, IFNA4, Thymic_stromal_lymphopoietin, LGTN, KIAA1333, MSH6, MYOT, RIPK5, BCL2L11, RPL27, Rnd1, Platelet_factor_4, HSD17B7, LSM8, CEP63, INTS8, CTNS, ASAHL, CELA3A, SMARCAL1, HEXB, SLC16A5, MAP3K12, FRMD6.

Additional RDEs are found in the 3'-UTRs of long noncoding RNAs, or primary transcripts encoding miRNAs. For example, RDEs from the 3'-UTR of THRIL (linc 1992), NIKILA lncRNA, SeT lncRNA, lncRNAs uc.197, RP11-172E9.2, LINC00598, lncRNAs LOC100128098, RP11-150012.3, and the primary transcripts encoding miR-146a, miR-let7e, miR-181c, miR-155, miR-125b, and miR-16.

A class of RDEs includes those which are bound by glycolytic enzymes such as glyceraldehyde phosphate dehydrogenase (GAPDH). This group of RDEs includes, for example, AU 19 (TMEM-219), AU 20 (TMEM-219snp), AU 21 (CCR7), AU 22 (SEM-A4D), and AU 23 (CDC142-SE2).

The RDE can be a Class I AU rich element that arises from the 3' UTR of a gene encoding, for example, c-myc, c-fos, betal-AR, PTH, interferon-gamma, MyoD, p21, Cyclin A, Cyclin B1, Cyclin D1, PAI-2, or NOS HANOS. The RDE can also be a Class II AU rich element and arises from the 3' UTR of a gene encoding, for example, GM-CSF, TNF-alpha, interferon-alpha, COX-2, IL-2, IL-3, bc1-2, interferon-beta, or VEG-F. The RDE can be a Class III AU rich element that arises from the 3' UTR of a gene encoding, for example, c-jun, GLUT1, p53, hsp 70, Myogenin, NF-M, or GAP-43. Other RDEs may be obtained from the 3'-UTRs of a T-cell receptor subunit (α, β, γ, or δ chains), cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3), and other checkpoint inhibitors. Still other RDEs may be obtained from the 3'-UTRs of senescence-associated secretory phenotype genes disclosed in Coppe et al., Ann. Rev. Pathol. 5:99-118 (2010), which is incorporated by reference in its entirety for all purposes (e.g., see Table 1).

The RDE can be bound by certain polypeptides including, for example, ARE poly(U) binding/degradation factor (AUF-1), tristetraprolin (TTP), human antigen-related protein (HuR), butyrate response factor 1 (BRF-1), butyrate response factor 2 (BRF-2), T-cell restricted intracellular antigen-1 (TIA-1), TIA-1 related protein (TIAR), CUG triplet repeat, RNA binding protein 1 (CUGBP-1), CUG triplet repeat, RNA binding protein 2 (CUGBP-2), human neuron specific RNA binding protein (Hel-N1, Hel-N2), RNA binding proteins HuA, HuB and HuC, KH-type splicing regulatory protein (KSRP), 3-methylglutaconyl-CoA hydratase (AUH), glyceraldehyde 3-phosphate dehydrogenase (GAPDH), heat shock protein 70 (Hsp70), heat shock protein 10 (Hsp10), heterogeneous nuclear ribonucleoprotein A1 (hnRNP A1), heterogeneous nuclear ribonucleoprotein A2 (hnRNP A2), heterogeneous nuclear ribonucleoprotein A3 (hnRNP A3), heterogeneous nuclear ribonucleoprotein C (hnRNP C), heterogeneous nuclear ribonucleoprotein L (hnRNP L), Bc1-2 AU-rich element RNA binding protein (TINO), Poly(A) Binding Protein Interacting Protein 2 (PAIP2), IRP1, pyruvate kinase, lactate dehydrogenase, enolase, and aldolase. The RDE binding protein also can be an enzyme involved in glycolysis or carbohydrate metabolism, such as, for example, Glyceraldehyde Phosphate Dehydrogenase (GAPDH), enolase (ENO1 or ENO3), Phosphoglycerate Kinase (PGK1), Triosephosphate Isomerase (TPI1), Aldolase A (ALDOA), Phosphoglycerate Mutase (PGAM1), Hexokinase (HK-2), or Lactate Dehydrogenase (LDH). The RDE binding protein can be an enzyme involved in the Pentose Phosphate Shunt, including for example, Transketolase (TKT) or Triosephosphate Isomerase (TPI1). Additional exemplary RNA binding proteins are those described in Castello et al., Molc. Cell 63:696-710 (2016); Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gki1012 (2006); Meisner et al., ChemBioChem 5:1432-1447 (2004); Guhaniyogi et al., Gene 265:11-23 (2001), all of which are incorporated by reference in their entirety for all purposes.

The RDE binding protein can be TTP which can bind to RDEs including for example, one or more of UUAUUUAUU (SEQ ID NO: 12) and AUUUA (SEQ ID NO: 1), or KSRP which binds AU-rich RDEs, or Auf1 which binds RDEs including for example, one or more of UUGA (SEQ ID NO: 13), AGUUU (SEQ ID NO: 11), or GUUUG (SEQ ID NO: 5), or CELF-1 which binds RDEs including for example, one or more of UUGUU (SEQ ID NO: 3), or HuR which binds RDEs including for example, one or more of UUUAUUU (SEQ ID NO: 8), UUUAUUU (SEQ ID NO: 9), or UUUGUUU (SEQ ID NO: 6), or ESRP1 or ESRP2 which binds RDEs including for example, one or more of UGGGGAU (SEQ ID NO: 14), or ELAV which binds RDEs including for example, one or more of UUUGUUU (SEQ ID NO: 6). The RDE binding protein can be an enzyme involved in glycolysis, including for example, GAPDH which binds AU rich elements including for example, one or more of AUUUA (SEQ ID NO: 1) elements, or ENO3/ENO1 which binds RDEs including for example, one or more of CUGCUGCUG (SEQ ID NO: 15), or ALDOA which binds RDEs including for example, one or more of AUUGA (SEQ ID NO: 16).

In an aspect, the RDE can be combined with an RNA control device to make the regulation by the RDE ligand inducible. For example, an RDE can be operably linked to an RNA control device where ligand binding by the RNA control device activates the regulatory element (e.g., a ribozyme or riboswitch) which inhibits the RDE (e.g., a ribozyme cleaves the RDE so RDE binding proteins no longer bind, or the riboswitch alters secondary structure). This places transcripts with the RDE and RNA control device under two types of control from the RDE, first the RDE can regulate the transcript subject to binding of RDE binding proteins as governed by conditions in the cell, and second, the RDE control can be removed by inducing the RNA control device with ligand. When ligand is added, the RNA control device renders the RDE unavailable for binding and RDE regulation is removed. When ligand is removed, new transcripts that are transcribed can be under the control of the RDE (as the RNA control device will not be activated). Alternatively, an RDE can be operable linked to an RNA control device where ligand binding turns off the regulatory element (e.g., a ribozyme). In this example, the presence of ligand inhibits the RNA control device and transcripts can be regulated by the RDE. When ligand is removed, the RNA control device renders the RDE unavailable for binding to RDE binding proteins and RDE regulation of the transcript is removed. The RNA control device could also cleave a polynucleotide that binds to the RDE to form a structure (e.g., a helix) that inhibits RDE proteins from binding to the RDE. In this example, the RNA control device can cleave the inhibitory polynucleotide which then does not bind or is inhibited for binding to the RDE. This cleavage by the RNA control device can be stimulated by ligand binding or inhibited by ligand binding.

Different RDEs have different kinetic parameters such as, for example, different steady expression levels, different $T_{max}$ (time to maximal expression level), different $C_{max}$ (maximum expression level), different dynamic range (expression/basal expression), different AUC, different kinetics of induction (acceleration of expression rate and velocity of expression rate), amount of expression, baseline expression, maximal dynamic range ($DR_{max}$), time to $DR_{max}$, area under the curve (AUC), etc. In addition, these kinetic properties of the RDEs can be altered by making concatemers of the same RDE, or combining different RDEs into regulatory units. Placing RDEs under the control of an operably linked RNA control device can also alter the kinetic properties of the RDE, RDE concatemer, or RDE combinations. Also, small molecules and other molecules that affect the availability of RDE binding proteins for binding RDEs can be used to alter the kinetic response of an RDE, RDE concatemer, and/or RDE combinations. The kinetic response of RDEs, RDE concatemers, and/or RDE combinations can be changed using constructs that express competitive RDEs in a transcript. Such transcripts with one or more competing RDEs can compete for RDE binding proteins and so alter the regulation of the desired gene by an RDE, RDE concatemer, and/or RDE combination. These competitive RDE transcripts can bind to RDE binding proteins reducing the amount of RDE binding protein available for binding to the RDE, RDE concatemer, and/or RDE combination. Thus, RDEs, RDE concatemers, and/or RDE combinations can be selected and/or combined with other conditions (discussed above) to provide a desired kinetic response to the expression of a transgene.

Table 2 in Example 20 shows that different RDEs (e.g., AU elements) provided different kinetics of expression. For example, different RDEs (e.g., AU elements) reached maximal induction (maximal dynamic range also known as fold induction) at different time points. The RDEs AU 2 and AU 101 reached maximal dynamic range ($DR_{max}$) at day 1 and then the dynamic range (DR) decreased showing reduced expression compared to basal expression. The RDEs AU 5 and AU 21 had a $DR_{max}$ at day 3/4 and this expression was maintained out to day 8. The RDEs AU 3, AU 7, AU 10, AU 20 and AU 23 had a $DR_{max}$ on day 6 and expression decreased on day 8. The RDEs AU 19 and AU 22 had $DR_{max}$ on day 8. The RDEs (e.g., AU elements) also had differences in the amount of expression covering a range of about 5500 fold comparing the expression of AU 7 to AU 10 (see Table 1). Thus, RDEs (AU elements) can be selected to provide maximal rates of expression at a desired time point and to provide a desired amount of polypeptide at that time point.

Some RNA binding proteins increase the rate of RNA degradation after binding to the RDE. Some RNA binding proteins decrease the rate of degradation of the RNA after binding to the RDE. More than one RNA binding protein binds can bind to an RDE. In some RDE regulatory units, more than one RNA binding protein binds to more than one RDE. Binding of one or more of the RNA binding proteins to the one or more RDEs can increase the degradation rate of the RNA. Binding of one or more of the RNA binding proteins can decrease the degradation rate of the RNA. RNA binding proteins that increase degradation may compete for binding to an RDE with RNA binding proteins that decrease degradation, so that the stability of the RNA is dependent of the relative binding of the two RNA binding proteins. Other proteins can bind to the RDE binding proteins and modulate the effect of the RNA binding protein on the RNA with the RDE. Binding of a protein to the RNA binding protein can increases RNA stability or decrease RNA stability. An RNA can have multiple RDEs that are bound by the proteins HuR and TTP. The HuR protein can stabilize the RNA and the TTP protein can destabilize the RNA. An RNA can have at least one RDE that interacts with the proteins KSRP, TTP and/or HuR. KSRP can destabilize the RNA and compete for binding with the HuR protein that can stabilize the RNA. The KSRP protein can bind to the RDE and destabilizes the RNA and the TTP protein can bind to KSRP and prevent degradation of the RNA. Different proteins may be bound to the same transcript and may have competing effects on degradation and stabilization rates. Different proteins may be bound to the same transcript and may have cooperative effects on degradation and stabilization rates. Different proteins may be bound to the same transcript at different times, conferring different effects on degradation and stabilization.

The RDE can be a Class II AU rich element, and the RNA binding protein can be GAPDH. The Class II AU rich element bound by GAPDH can be AUUUAUUUAUUUA (SEQ ID NO: 2). The Class II AU rich element and GADPH can be used to control the expression of a transgene, a CAR, Smart CAR (RNA control device—CAR), DE-CAR (destabilizing element—CAR), Smart-DE-CAR, and/or Side-CAR. The Class II AU rich element and GADPH also can be used to effect the expression of a transgene and/or a CAR in a T-lymphocyte. The Class II AU rich element and GADPH can be used to effect the expression of a transgene and/or a CAR in a CD8+T-lymphocyte. The Class II AU rich element and GADPH can be used to effect the expression of a transgene and/or a CAR in a CD4+T-lymphocyte. The Class II AU rich element and GADPH can be used to effect the expression of a transgene and/or a CAR in a natural killer cell.

The RDE may have microRNA binding sites. The RDE can be engineered to remove one or more of these microRNA binding sites. The removal of the microRNA binding sites can increase the on expression from a construct with an RDE by at least 5, 10, 15, 20, 50 or 100 fold. The RDE with the microRNA sites can be an RDE that is bound by GAPDH. The removal of microRNA sites from the RDE bound by GAPDH can increase the on expression of a construct with the GAPDH sensitive RDE by at least 5-10 fold. This GAPDH control through the RDE can be used to deliver a payload at a target site. The GAPDH control can be tied to activation of the eukaryotic cell by a CAR that recognizes an antigen found preferentially at the target site.

The RDE can be the 3'-UTR of IL-2 or IFN-γ, and removal of micro-RNA sites can increase the rate of expression and/or the dynamic range of expression from a transgene RNA with the RDE. The RDE can be the 3'-UTR of IL-2 and the removed micro-RNA sites can be the MIR-186 sites which deletion increases the kinetics of expression and increases the dynamic range of expression by about 50-fold. The RDE also can be the 3'-UTR of IFN-γ and the micro-RNA sites removed can be the MIR-125 sites.

The dynamic range of expression (control) with an RDE can be increased by optimizing the codons of the transgene controlled by the RDE. By increasing the GC content of the wobble position of the codons in a transgene the efficiency of translation can be increased by 1-2 logs (10-100 fold). The increased efficiency of translation means the amount of expression in the "on" state with the RDE is increased. If the "off" state expression rate is not changed or changed less, the overall dynamic range of control with the RDE is increased.

New RDEs can be obtained from synthetic libraries made by combinatorially mixing and matching parts of known RDEs by applying techniques such as molecular breeding and/or directed evolution to the 3'-UTRs of genes known to have an RDE. For example, multiple 3'-UTRs with different RDEs are fragmented and assembled into synthetic 3'-UTRs that are then screened or selected for RDE activity. RDEs with desired properties can be discovered from such libraries using positive and/or negative selections.

Alternative Splicing

Alternative splicing can link a change in metabolic state in a cell to the splicing of a pre-mRNA transcript into a mRNA that encodes and is translated into a desired polypeptide. For example, following a change in metabolic state of a cell, a pre-mRNA transcript can undergo alternative splicing to produce a payload in the cell. Prior to the alternative splicing the pre-mRNA transcript can be spliced into a transcript encoding a nonsense polypeptide or into an mRNA encoding a different polypeptide product.

hnRNPLL (heterogeneous nuclear ribonucleoprotein L like) is a RNA binding polypeptide that is made when immune cells (e.g., T-cells and B-cells) are activated (change in metabolic state). hnRNPLL is a master regulator of activation-induced alternative splicing in lymphocytes, including T cells and B-cells. In T-cells, hnRNPLL effects the splicing of a variety of transcripts including CD45, a tyrosine phosphatase essential for T-cell development and activation.

hnRNPLL binds to CA repeats and also to C rich motifs, A rich motifs, and T rich motifs including, for example, $CACACA(CA)_n$, CTTCCt/c, CATt/a, CATT, and TTTAt/aA. When hnRNPLL binding sites are in the 3'-UTRs of a transcript, binding of hnRNPLL to the site can stabilize the transcript. When hnRNPLL binding sites are within about 1 kilobase on the 5' side of an exon, hnRNPLL binding promotes inclusion of the exon during splicing. When hnRNPLL binding sites are within about 1 kilobase on the 3' side of an exon, hnRNPLL binding promotes exclusion of the exon. When hnRNPLL binds to a transcript it can alter the splicing pattern of the transcript resulting in a new mRNA transcript and new noncoding excision products (excised introns or introns plus exons). This alternative splicing pattern can produce an alternatively spliced mRNA that now encodes a desired polypeptide (e.g., a payload), and/or the new noncoding excision products can encode a miRNA or siRNA that is only produced upon alternative splicing.

hnRNPLL alternative splicing can be used alone or in combination with other regulatory signals such as RDEs. Together hnRNPLL alternative splicing and RDEs can control expression of a payload upon activation of a cell (change in metabolic state) when it reaches a target site having a ligand that binds to a CAR, T-cell receptor (TCR), or other receptor expressed on the cell. Binding of ligand to the receptor (e.g., CAR or TCR) activates the cell, increases expression of a payload by RDE mechanisms, and produces alternative splicing following hnRNPLL expression. Together the RDE control and alternative splicing produce desired amounts of a payload or other transgene.

hnRNPLL alternative splicing can also be used to turn off a gene that is being expressed while the cell is quiescent. When the quiescent cell is activated by ligand binding to a receptor (e.g., CAR or TCR) this changes the metabolic state of the cell and hnRNPLL is expressed. If a gene being expressed while the cell is quiescent has hnRNPLL binding sites the binding of hnRNPLL can alter the splicing of the transcript so that the mRNA no longer encodes the gene product. For example, a cell (e.g., T-cell or B-cell) can be engineered to express a stemness factor (e.g., Tox and/or TCF7) while the cell is quiescent. The nucleic acid encoding Tox and/or TCF7 can include intron(s) with hnRNPLL binding sites so that in the absence of hnRNPLL the transcripts are spliced to make the Tox and/or TCF7 polypeptides, but upon cell activation and expression of hnRNPLL these transcripts now undergo alternative splicing and no longer produce transcripts encoding Tox and/or TCF7.

hnRNPLL alternative splicing also produces new "introns" or noncoding excision products as well as new mRNAs. The new introns can encode active RNAs (e.g., miRNA, siRNA, etc.) that are only expressed in the new introns. This adds yet another level of control to hnRNPLL alternative splicing as the miRNAs or siRNAs can turn off genes in the activated cells that are detrimental to the effector state of the cell including, for example, Tox, SCF7, and other exhaustion factors. miRNAs and siRNAs that could be controlled in this manner include, for example, miR155, mIR-192, mIR-34a, miR-133a, miR-138-5p, miR-342-5p, miR-491-5p, miR-541-3p, hsa-mir-26b-5p (MIRT030248), and hsa-mir-223-3p (MIRT054680).

Chimeric Antigen Receptors

Chimeric antigen receptors (CARs) can be fused proteins comprising an extracellular antigen-binding/recognition element, a transmembrane element that anchors the receptor to the cell membrane and at least one intracellular element. These CAR elements are known in the art, for example as described in patent application US20140242701, which is incorporated by reference in its entirety for all purposes herein. The CAR can be a recombinant polypeptide expressed from a construct comprising at least an extracellular antigen binding element, a transmembrane element and an intracellular signaling element comprising a functional signaling element derived from a stimulatory molecule. The stimulatory molecule can be the zeta chain associated with the T cell receptor complex. The cytoplasmic signaling element may further comprise one or more functional signaling elements derived from at least one costimulatory molecule. The costimulatory molecule can be chosen from 4-1BB (i.e., CD137), CD27 and/or CD28. The CAR may be a chimeric fusion protein comprising an extracellular antigen recognition element, a transmembrane element and an intracellular signaling element comprising a functional signaling element derived from a stimulatory molecule. The CAR may comprise a chimeric fusion protein comprising an extracellular antigen recognition element, a transmembrane element and an intracellular signaling element comprising a functional signaling element derived from a co-stimulatory molecule and a functional signaling element derived from a stimulatory molecule. The CAR may be a chimeric fusion protein comprising an extracellular antigen recognition element, a transmembrane element and an intracellular signaling element comprising two functional signaling elements derived from one or more co-stimulatory molecule(s) and a functional signaling element derived from a stimulatory molecule. The CAR may comprise a chimeric fusion protein comprising an extracellular antigen recognition element, a transmembrane element and an intracellular signaling element comprising at least two functional signaling elements derived from one or more co-stimulatory molecule(s) and a functional signaling element derived from a stimulatory molecule. The CAR may comprise an optional leader sequence at the amino-terminus (N-term) of the CAR fusion protein. The CAR may further comprise a leader sequence at the N-terminus of the extracellular antigen recognition element, wherein the leader sequence is optionally cleaved from the antigen recognition element (e.g., a scFv) during cellular processing and localization of the CAR to the cellular membrane.

Chimeric Antigen Receptor-Extracellular Element

Exemplary extracellular elements useful in making CARs are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element(s) can be obtained from the repertoire of antibodies obtained from the immune cells of a subject that has become immune to a disease, such as for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element may be obtained from any of the wide variety of extracellular elements or secreted proteins associated with ligand binding and/or signal transduction as described in U.S. patent application Ser. No. 15/070,352 filed on Mar. 15, 2016, U.S. patent application Ser. No. 15/369,132 filed Dec. 5, 2016, U.S. Pat. Nos. 5,359,046, 5,686,281 and 6,103,521, all of which are incorporated by reference in their entirety for all purposes.

The extracellular element can also be obtained from a variety of scaffold protein families which share the common feature of a protein scaffold core with protein loops that can confer binding specificity and which loops can be altered to provide different binding specificities. Knottins are one such scaffold protein that has peptide loops which can be engineered to produce different binding specificities. For example, knottins can be engineered to have high affinity for specific integrin peptides. See for example, Silverman et al., J. Mol. Biol. 385:1064-75 (2009) and Kimura et al, Proteins 77:359-69 (2009), which are incorporated by reference in their entirety for all purposes. Some cancers overexpress certain integrin peptides and such cancers can be targeted by CARs that have an extracellular element that is a knottin specific for the overexpressed integrin. One such integrin is the integrin avf3.6 which is upregulated in multiple solid tumors such as those derived from colon, lung, breast, cervix, ovary/fallopian tubes, pancreas, and head and neck. See for example, Whilding et al., Biochem. Soc. Trans. 44:349-355 (2016), which is incorporated by reference in its entirety for all purposes.

The extracellular element can also be derived from knottins, which are a family of peptides containing a disulfide bonded core that confers outstanding proteolytic resistance and thermal stability. Knottins, which naturally function as protease inhibitors, antimicrobials, and toxins, are composed of several loops that possess diverse sequences amongst family members. Knottins can be engineered to include additional diversity of sequence in the loops to increase and create new binding specificities. Engineered knottins can be made to bind desired targets (e.g., desired antigens) with a desired specificity. Some Knottins bind with nM specificity to integrins and can be used to target a CAR to a certain integrins (e.g., $\alpha v \beta 3/\alpha v \beta 5$, $\alpha v \beta 3/\alpha v \beta 5/\alpha 5 \beta 1$, or $\alpha v \beta 6$ integrins). Integrins such as $\alpha v \beta 6$ can be upregulated on solid tumors and so can be suitable targets for a CAR. Such $\alpha v \beta 6$ integrin specific CARs can be made using a knottin specific for the $\alpha v \beta 6$ integrin as the extracellular element of the CAR. Activation of an engineered cell (e.g., a T-cell) through the $\alpha v \beta 6$ knottin-CAR can be used to deliver a pay load to a solid tumor under the control of an RDE that causes expression of the payload upon CAR cell activation.

In an aspect, the extracellular domain can be an antibody or other binding molecule that binds specifically to an onco-sialylated CD43 that is widely found on AML and MDS blasts. See Hazenberg et al., European Hematology Associate abstracts, Abst 5511 (2016), which is incorporated by reference in its entirety for all purposes. The antibody AT14-013 binds a specific sialylated epitope on the onco-sialylated CD43 which epitope is not found on CD43 associated with normal cells and tissue. See WO 2016/209079 and WO 2015/093949, both of which are incorporated by reference in their entirety for all purposes. This antibody or antibodies or other binding molecules which compete for onco-sialylated CD43 binding with AT14-013 are used to make anti-onco sialylated CD43 CARs. For example, the variable regions of the heavy and light chain of AT14-013 can be taken and reformatted as a single chain antibody for use as the extracellular domain of a CAR. Such an extracellular domain on a CAR directs the CAR cell (e.g., anti-onco sialylated CD43 CAR T-lymphocyte) to the AML and/or MDS cells targeting them for cell killing or modification by the CAR cell.

Other tumor associated antigens that can be the target of the CAR include, for example, c-Met (e.g., NSCLC), gpNMB (e.g., melanoma, breast cancer, other solid tumors), TRAP-2 (e.g., epithelial tumors and other solid tumors), CEACAM5 (e.g., colorectal cancer), CD56 (e.g., SCLC), CD25 (e.g., hematological cancers), guanyl cyclase C (e.g., pancreatic cancer), CAG (e.g., solid tumors), LIV-1 (e.g., breast cancer), PTK7 (e.g., lung cancer, colorectal cancer, breast cancer, and ovarian cancer), LAMP-1 (e.g., colorectal cancer, melanoma, laryngeal cancer), P-cadherin 3 (e.g., epithelial tumors), HER-3 (e.g., breast cancer), CD133 (e.g., hepatocellular carcinoma, pancreatic cancer, colorectal cancer, cholangiocarcinoma), BCMA (e.g., multiple myeloma), CD138 (e.g., multiple myeloma), Ig kappa light chain (e.g., leukemia, lymphoma, NHL, and multiple myeloma), CD30 (e.g., NHL, HD), IL13Ra2 (e.g., glioblastoma), and ligands for NKG2D (e.g., using the NKG2D receptor as the binding domain for, e.g., AML, MDS, and MM).

Other tumor associated antigens that can be the target of the CAR include, for example, mesothelin, disialoganglioside (GD2), Her-2, MUC1, GPC3, EGFRVIII, CEA, CD19, EGFR, PSMA, GPC2, folate receptor β, IgG Fc receptor, PSCA, PD-L1, EPCAM, Lewis Y Antigen, L1CAM, FOLR, CD30, CD20, EPHA2, PD-1, C-MET, ROR1, CLDN18.2, NKG2D, CD133, TSHR, CD70, ERBB, AXL, Death Receptor 5, VEGFR-2, CD123, CD80, CD86, TSHR, ROR2, CD147, kappa IGG, IL-13, MUC16, IL-13R, NY-ESO-1, IL13RA2, DLL3, FAP, LMP1, TSHR, BCMA, NECTIN-4, MG7, AFP (alpha-fetoprotein), GP100, B7-H3, Nectin-4, MAGE-A1, MAGE-A4, MART-1, HBV, MAGE-A3, TAA, GP100, Thyroglobulin, EBV, HPV E6, PRAME, HERV-E, WT1, GRAS G12V, p53, TRAIL, MAGE-A10, HPV-E7, KRAS G12D, MAGE-A6, CD19, BCMA, CD22, CD123, CD20, CD30, CD33, CD138, CD38, CD7, SLAMF7, IGG FC, MUC1, Lewis Y Antigen, CD133, ROR1, FLT3, NKG2D, Kappa light chain, CD34, CLL-1, TSLP, CD10, PD-L1, CD44V6, EBV, CD5, GPC3, CD56, integrin B7, CD70, MUCL, CKIT, CLDN18.2, TRBC1, TAC1, CD56, and CD4.

Still other tumor associated antigens that can be the target of the CAR include, for example, CD2, CD18, CD27, CD37, CD72, CD79A, CD79B, CD83, CD117, CD172, ERBB3, ERBB4, DR5, HER2, CS1, IL-1RAP, ITGB7, SLC2A14, SLC4A1, SLC6A11, SLC7A3, SLC13A5, SLC19A1, SLC22A12, SLC34A1, slc45A3, SLC46A2, Fra, IL-13Ra2, ULBP3, ULBP1, CLD18, NANOG, CEACAM8, TSPAN16, GLRB, DYRK4, SV2C, SIGLEC8, RBMXL3, HIST1HIT, CCR8, CCNB3, ALPPL2, ZP2, OTUB2, LILRA4, GRM2, PGG1, NBIF3, GYPA, ALPP, SPATA19, FCRLI, FCRLA, CACNG3, UPK3B, 12UMO4, MUC12, HEPACAM, BPI, ATP6V0A4, HMMR, UPK1A, ADGRV1, HERC5, C3AR1, FASLG, NGB, CELSR3, CD3G, CEACAM3, TNFRSFBC, MS4AB, S1PR5, EDNRB, SCN3A, ABCC8, ABCB1, ANO1, KCND2, HTR4, CACNB4, HTR4, CNR2, 26LRB, EXOC1, ENTPP1, ICAM3, ABCGB, SCN4B, SPN, CD68, ITGAL, ITGAM, SCTR, CYYR1, CLCN2, SLARA3, and JAG3.

Intracellular Element

The intracellular element can be a molecule that can transmit a signal into a cell when the extracellular element of the Smart CAR (RNA control device—CAR), DE-CAR (destabilizing element—CAR), RDE-CAR, Smart-DE-CAR, Smart-RDE-CAR, DE-RDE-CAR, Smart-DE-RDE-CAR, and/or Side-CAR (collectively "CARS") binds to (interacts with) an antigen. The intracellular signaling element can be generally responsible for activation of at least one of the normal effector functions of the immune cell in which the CAR(s) has been introduced. The term "effector function" refers to a specialized function of a cell. Effector function of a T cell, for example, may be cytolytic activity or helper activity including the secretion of cytokines. Thus the term "intracellular signaling element" refers to the portion of a protein which transduces the effector function signal and directs the cell to perform a specialized function. While the entire intracellular signaling domain can be employed, in many cases the intracellular element or intracellular signaling element need not consist of the entire domain. To the extent that a truncated portion of the intracellular signaling domain is used, such truncated portion may be used as long as it transduces the effector function signal. The term intracellular signaling element is thus also meant to include any truncated portion of the intracellular signaling domain sufficient to transduce the effector function signal. Examples of intracellular signaling elements for use in the Smart CAR, DE-CAR, RDE-CAR, Smart-DE-CAR, Smart-RDE-CAR, DE-RDE-CAR, Smart-DE-RDE-CAR, and/or Side-CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

Intracellular elements and combinations of polypeptides useful with or as intracellular elements are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Transmembrane Element and Spacer Element

The CAR, and/or RDE-CAR may comprise a transmembrane element. The transmembrane element can be attached to the extracellular element of CAR, and/or RDE-CAR. The transmembrane element can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). The transmembrane element can be associated with one of the other elements used in the CAR, and/or RDE-CAR. The transmembrane element can be selected or modified by amino acid substitution to avoid binding of such elements to the transmembrane elements of the same or different surface membrane proteins, e.g., to minimize interactions with other members of the receptor complex. The transmembrane element can be modified to remove cryptic splice sites (e.g., CARS made with a CD8 transmembrane domain can be engineered to remove a cryptic splice site) and/or a transmembrane element can be used in the CAR construct that does not have cryptic splice sites. The transmembrane element can be capable of homodimerization with another CAR, and/or RDE-CAR on the cell surface. The amino acid sequence of the transmembrane element may be modified or substituted so as to minimize interactions with the binding elements of the native binding partner present in the same cell.

Transmembrane elements useful in the present invention are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Chimeric Antigen Receptors: Side-CARs

Side CARs, selection of Side CARs, and their use with or without a tether are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Receptors

CARS may be used as the receptor with the cell and the RDE-transgene. CARS are described above. In addition to CARS, other receptors may be used to activate or otherwise change conditions in a cell so that a transgene under the control of an RDE is expressed. Receptors that recognize and respond to a chemical signal can be coupled to expression of the transgene through the RDE. For example, ion channel-linked (ionotropic) receptors, G protein-linked (metabotropic) receptors, and enzyme-linked receptors can be coupled to the expression of the transgene.

One class of receptor that can be coupled to transgene expression are immune receptors such as, for example, T-cell receptors, B-cell receptors (aka antigen receptor or immunoglobulin receptor), and innate immunity receptors.

T-cell receptors are heterodimers of two different polypeptide chains. In humans, most T cells have a T-cell receptor made of an alpha ($\alpha$) chain and a beta ($\beta$) chain have a T-cell receptor made of gamma and delta ($\gamma/\delta$) chains (encoded by TRG and TRD, respectively). Techniques and primers for amplifying nucleic acids encoding the T-cell receptor chains from lymphocytes are well known in the art and are described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. The TCR repertoires can be used as separate chains to form an antigen binding domain. The TCR repertoires can be converted to single chain antigen binding domains. Single chain TCRs can be made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/Aggen_David.pdf?sequence=1, all of which are incorporated by reference in their entirety for all purposes.

B-cell receptors include an immunoglobulin that is membrane bound, a signal transduction moiety, CD79, and an ITAM. Techniques and primers for amplifying nucleic acids encoding human antibody light and heavy chains are well-known in the art, and described in, for example, ProGen's Human IgG and IgM Library Primer Set, Catalog No. F2000; Andris-Widhopf et al., "Generation of Human Fab Antibody Libraries: PCR Amplification and Assembly of Light and Heavy Chain Coding Sequences," Cold Spring Harb. Protoc. 2011; Lim et al., Nat. Biotechnol. 31:108-117 (2010); Sun et al., World J. Microbiol. Biotechnol. 28:381-386 (2012); Coronella et al., Nucl. Acids. Res. 28:e85 (2000), all of which are incorporated by reference in their entirety for all purposes. Techniques and primers for amplifying nucleic acids encoding mouse antibody light and heavy chains are well-known in the art, and described in, for example, U.S. Pat. No. 8,143,007; Wang et al., BMC Bioinform. 7(Suppl):S9 (2006), both of which are incorporated by reference in their entirety for all purposes. The antibody repertoires can be used as separate chains in antigen binding domains, or converted to single chain antigen binding domains. Single chain antibodies can be made from nucleic acids encoding human light and heavy chains using techniques well-known in the art including, for example, those described in Pansri et al., BMC Biotechnol. 9:6 (2009); Peraldi-Roux, Methods Molc. Biol. 907:73-83 (2012), both of which are incorporated by reference in their entirety for all purposes. Single chain antibodies can be made from nucleic acids encoding mouse light and heavy chains using techniques well-known in the art including, for example, those described in Imai et al., Biol. Pharm. Bull. 29:1325-1330 (2006); Cheng et al., PLoS ONE 6:e27406 (2011), both of which are incorporated by reference in their entirety for all purposes.

Innate immunity receptors include, for example, the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105).

G-protein linked receptors also known as seven-transmembrane domain receptors are a large family of receptors that couple receptor binding of ligand to cellular responses through G proteins. These G-proteins are trimers of α, β, and γ subunits (known as Gα, Gβ, and Gγ, respectively) which are active when bound to GTP and inactive when bound to GDP. When the receptor binds ligand it undergoes a conformational change and allosterically activates the G-protein to exchange GTP for bound GDP. After GTP binding the G-protein dissociates from the receptor to yield a Gα-GTP monomer and a Gβγ dimer. G-protein linked receptors have been grouped together into classes which include, for example, Rhodopsin-like receptors, secretin receptors, metabotropic glutamate/pheromone receptors, fungal mating pheromone receptors, cyclic AMP receptors, and frizzled/smoothened receptors. G-protein receptors are used in a wide variety of physiological processes including detection of electromagnetic radiation, gustatory sense (taste), sense of smell, neurotransmission, immune system regulation, growth, cell density sensing, etc.

Enzyme linked receptors also known as a catalytic receptor, is a transmembrane receptor, where the binding of an extracellular ligand causes enzymatic activity on the intracellular side. Enzyme linked receptors have two domains joined together by a transmembrane portion (or domain) of the polypeptide. The two terminal domains are an extracellular ligand binding domain and an intracellular domain that has a catalytic function. There are multiple families of enzyme linked receptors including, for example, the Erb receptor family, the glial cell-derived neurotrophic factor receptor family, the natriuretic peptide receptor family, the trk neurotrophin receptor family, and the toll-like receptor family.

Ion channel linked receptors also known as ligand-gated ion channels are receptors that allow ions such as, for example, $Na^+$, $K^+$, $Ca^{2+}$ and $Cl^-$ to pass through the membrane in response to the binding of a ligand to the receptor. There are multiple families of ligand-gated ion channels including, for example, cationic cys-loop receptors, anionic cys-loop receptors, ionotropic glutamate receptors (AMPA receptors, NMDA receptors), GABA receptors, 5-HT receptors, ATP-gated channels, and $PIP_2$-gated channels.

Eukaryotic Cells

Various eukaryotic cells can be used as the eukaryotic cell. The eukaryotic cells can be animal cells. The eukaryotic cells can be mammalian cells, such as mouse, rat, rabbit, hamster, porcine, bovine, feline, or canine. The mammalian cells can be cells of primates, including but not limited to, monkeys, chimpanzees, gorillas, and humans. The mammalians cells can be mouse cells, as mice routinely function as a model for other mammals, most particularly for humans (see, e.g., Hanna, J. et al., *Science* 318:1920-23, 2007; Holtzman, D. M. et al., *J Clin Invest.* 103(6):R15-R21, 1999; Warren, R. S. et al., *J Clin Invest.* 95: 1789-1797, 1995; each publication is incorporated by reference in its entirety for all purposes). Animal cells include, for example, fibroblasts, epithelial cells (e.g., renal, mammary, prostate, lung), keratinocytes, hepatocytes, adipocytes, endothelial cells, and hematopoietic cells. The animal cells can be adult cells (e.g., terminally differentiated, dividing or non-dividing) or embryonic cells (e.g., blastocyst cells, etc.) or stem cells. The eukaryotic cell also can be a cell line derived from an animal or other source.

The eukaryotic cells can be stem cells. A variety of stem cells types are known in the art and can be used as the eukaryotic cell, including for example, embryonic stem cells, inducible pluripotent stem cells, hematopoietic stem cells, neural stem cells, epidermal neural crest stem cells, mammary stem cells, intestinal stem cells, mesenchymal stem cells, olfactory adult stem cells, testicular cells, and progenitor cells (e.g., neural, angioblast, osteoblast, chondroblast, pancreatic, epidermal, etc.). The stem cells can be stem cell lines derived from cells taken from a subject.

The eukaryotic cell can be a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. The eukaryotic cell can be derived from any of these circulating eukaryotic cells. Transgenes may be used with any of these circulating cells or eukaryotic cells derived from the circulating cells. The eukaryotic cell can be a T-cell or T-cell precursor or progenitor cell. The eukaryotic cell can be a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. The eukaryotic cell can be a natural killer cell, or a precursor or progenitor cell to the natural killer cell. The eukaryotic cell can be a B-cell, or a B-cell precursor or progenitor cell. The eukaryotic cell can be a neutrophil or a neutrophil precursor or progenitor cell. The eukaryotic cell can be a megakaryocyte or a precursor or progenitor cell to the megakaryocyte. The eukaryotic cell can be a macrophage or a precursor or progenitor cell to a macrophage.

The eukaryotic cells can be obtained from a subject. The subject may be any living organisms. The cells can be derived from cells obtained from a subject. Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. Any number of T cell lines available in the art also may be used. T-cells can be obtained from a unit of blood collected from a subject using any number of techniques known to the skilled artisan, such as Ficoll separation. Cells from the circulating blood of an individual can be obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells can be washed with phosphate buffered saline (PBS). In an alternative aspect, the wash solution lacks calcium and may lack magnesium or may lack many if not all divalent cations. Initial activation steps in the absence of calcium can lead to magnified activation.

Enrichment of a T cell population by negative selection can be accomplished with a combination of antibodies directed to surface markers unique to the negatively selected cells. Cells can be enriched by cell sorting and/or selection via negative magnetic immunoadherence or flow cytometry using a cocktail of monoclonal antibodies directed to cell surface markers present on the cells. For example, to enrich for CD4+ cells, a monoclonal antibody cocktail typically includes antibodies to CD14, CD20, CD11b, CD16, HLA-DR, and CD8. It may be desirable to enrich for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference in its entirety for all purposes.

NK cells may be expanded in the presence of a myeloid cell line that has been genetically modified to express membrane bound IL-15 and 4-1BB ligand (CD137L). A cell line modified in this way which does not have WIC class I and II molecules is highly susceptible to NK cell lysis and activates NK cells. For example, K562 myeloid cells can be transduced with a chimeric protein construct consisting of human IL-15 mature peptide fused to the signal peptide and transmembrane domain of human CD8a and GFP. Transduced cells can then be single-cell cloned by limiting dilution and a clone with the highest GFP expression and surface IL-15 selected. This clone can then be transduced with human CD137L, creating a K562-mb15-137L cell line. To preferentially expand NK cells, peripheral blood mononuclear cell cultures containing NK cells are cultured with a K562-mb15-137L cell line in the presence of 10 IU/mL of IL-2 for a period of time sufficient to activate and enrich for a population of NK cells. This period can range from 2 to 20 days, preferably about 5 days. Expanded NK cells may then be transduced with the anti-CD19-BB-ζ chimeric receptor.

Modification of CD3 Epsilon in T-Lymphocytes

T-lymphocytes can be modified to reduce graft versus host reactions. For example, allogenic T-lymphocytes can be modified so that upon transplantation graft versus host reactions are reduced. The allogenic T-lymphocytes can be used in a CAR therapy and/or can carry other transgenes for delivery by the T-lymphocyte at a target site. The T-lymphocytes can be modified by introducing a mutant that has a dominant effect on T-cell receptor function. For example, the mutant can knock out the T-cell receptor, or can disrupt signaling from the T-cell receptor. Mutations of the CD3 epsilon chain can have such dominant negative effects on T-cell receptor signaling. An example of a negative dominant mutant of CD3 epsilon is a C119S/C122S double mutant that alters the C-X-X-C motif in the CD3 epsilon to S-X-X-S. This double mutant is defective for signal transduction from an activated T-cell receptor and so binding of host antigens by a T-lymphocyte (e.g., an allogenic T-lymphocyte) does not activate the T-lymphocyte reducing graft versus host disease.

The CD3 epsilon double mutant (C119S/C122S) can be introduced into the T-lymphocyte by integrating it to the CD3 epsilon locus of the T-lymphocyte, or because this double mutant is a negative dominant it can be introduced at other sites in the T-lymphocyte genome or can be transiently transfected/transduced into the T-lymphocyte. Transient transfection can produce T-lymphocytes with CD3 epsilon double mutant associated with the T-cell receptors of the T-lymphocytes prior to activation by binding of a CAR (or other receptor) at the target site. If the transient expression has ended when the T-lymphocyte reaches target and interacts with its CAR, the CAR T-lymphocytes can kill through CAR reactions and through graft versus host/tumor cell reactions through the allogenic T-cell receptors.

In an example, T-lymphocytes are obtained from a host (e.g., an allogenic host) and activated with CD3/CD28 beads. These activated T-lymphocytes are transfected with a construct encoding a CAR (and/or other desired transgene) and a double mutant CD3 epsilon (C119S/C122S). T-lymphocytes transfected/transduced with the CAR are isolated (e.g., by affinity isolation with the CAR or a selection against active T-lymphocytes with active TCRs can be done) and administered to a subject.

Another mutation of CD3 epsilon can make deletions of one or more of the ITAM portions of the polypeptide. These ITAM deletions reduce the signaling capacity of CARS made with these ITAM mutants. The CD3 epsilon of the CAR can be engineered to have ITAM deletions of one or more ITAM sequences. T-cells engineered with a CAR and these CD3 epsilon genes with the ΔITAM(s) can be used with payloads under control of an RDE. When these T-cells are activated by the CAR the payload is expressed. The ΔITAMs reduce the responsiveness of the cell to the CAR (a crippled CAR) which can reduce or prevent T-cell exhaustion. This allows the T-cell to produce the transgene payload for a longer period of time.

Nucleic Acids

Also described in this disclosure are nucleic acids that encode, at least in part, the individual peptides, polypeptides, proteins, RDEs, and other post-transcriptional control devices described herein. The nucleic acids may be natural, synthetic or a combination thereof. The nucleic acids of the invention may be RNA, mRNA, DNA or cDNA.

The nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not αvailable from complex media, e.g., the gene encoding D-alanine racemase for Bacilli. An exemplary selection scheme can utilize a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a Smart CAR, DE-CAR, RDE-CAR, Smart-DE-CAR, Smart-RDE-CAR, DE-RDE-CAR, Smart-DE-RDE-CAR, and/or Side-CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention is not limited to the use of constitutive promoters.

Inducible or repressible promoters are also contemplated for use in this disclosure. Examples of inducible promoters include, but are not limited to a Nuclear Factor of Activated T-cell inducible promoter (NFAT), a metallothionein promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Macian et al., Oncogene 20:2476-2489 (2001); Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes. Inducible promoter also include promoters with heat shock elements that respond to mild hyperthermia. Heat shock elements are made of multiple inverted repeats of the consensus sequence 5'-nGAAn-3' located upstream of a promoter such as, for example, a promoter from a heat shock gene (e.g., HSPB1).

Expression vectors typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

The expression vector may be a bi-cistronic construct or multiple cistronic construct. The two cistrons may be oriented in opposite directions with the control regions for the cistrons located in between the two cistrons. When the construct has more than two cistrons, the cistrons may be arranged in two groups with the two groups oriented in opposite directions for transcription. Exemplary bicistronic constructs are described in Amendola et al., Nat. Biotechnol. 23:108-116 (2005), which is incorporated by reference in its entirety for all purposes. The control region for one cistron may be capable of high transcription activity and the other may have low transcriptional activity under conditions of use. One or both control regions may be inducible. Examples of high transcription activity control regions include, for example, MND, EF1-alpha, PGK1, CMV, ubiquitin C, SV40 early promoter, tetracycline-responsive element promoter, cell-specific promoters, human beat-actin promoter, and CBG (chicken beta-globin), optionally including the CMV early enhancer. Examples of low transcription activity control regions include, for example, TRE3G (commercially sold by Clontech, a tetracycline-responsive element promoter with mutations that reduce basal expression), T-REx™ (commercially sold by ThermoFisher), and a minimal TATA promoter (Kiran et al., Plant Physiol. 142:364-376 (2006), which is incorporated by reference in its entirety for all purposes), HSP68, and a minimal CMV promoter. Examples of inducible control regions include, for example, NFAT control regions (Macian et al, Oncogene 20:2476-2489 (2001)), and the inducible control regions described above.

The bi-cistronic construct may encode a CAR and a polypeptide that is a payload (or makes a payload) to be delivered at a target site. Exemplary payloads are described above and below. The nucleic acid encoding the CAR can be operably linked to a strong promoter, a weak promoter, and/or an inducible promoter, and optionally, operably linked to a RNA control device, DE, RDE, or combination of the foregoing. The CAR can be encoded by nucleic acids in a Side-CAR format. The nucleic acid encoding the polypeptide can be operably linked to a strong promoter, a weak promoter, and/or an inducible promoter. The nucleic acid encoding the polypeptide that is a payload (or makes the payload) can be under the control of an RDE. The RDE may be one that responds to the activation state of the cell through, for example, glycolytic enzymes such as, for example, glyceraldehyde phosphate dehydrogenase (GAPDH), enolase (ENO1 or ENO3), phosphoglycerate kinase (PGK1), triose phosphate isomerase (TPI1), aldolase A (ALDOA), or phosphoglycerate mutase (PGAM1). The RDE may also be bound and regulated by other energy metabolism enzymes such as, for example, transketolase (TKT), malate dehydrogenase (MDH2), succinyl CoA Synthetase (SUGLG1), ATP citrate lyase (ACLY), or isocitrate dehydrogenase (IDH1/2). The host cell can express a CAR that binds to its antigen at a target site in a subject. This binding of antigen at the target site activates the cell causing the cell to increase glycolysis which induces expression of the nucleic acid encoding the polypeptide under the control of the RDE (bound by glycolytic or other energy metabolism enzymes).

The multicistronic constructs can have three or more cistrons with each having control regions (optionally inducible) and RDEs operably linked to some or all of the transgenes. These cassettes may be organized into two groups that are transcribed in opposite directions on the construct. Two or more transgenes can be transcribed from the same control region and the two or more transgenes may have IRES (internal ribosome entry site) sequences operably linked to the downstream transgenes. Alternatively, the two or more transgenes are operably linked together by 2A elements as described in Plasmids 101: Multicistronic Vectors found at blog.addgene.org/plasmids-101-multicistrnic-vectors. Commonly used 2A sequences include, for example, EGRGSLLTCGDVEENPGP (T2A) (SEQ ID NO: 17), ATNFSLLKQAGDVEENPGP (P2A) (SEQ ID NO: 18); QCTNYALLKLAGDVESNPGP (E2A) (SEQ ID NO: 19); and VKQTLNFDLLKLAGDVESNPGP (F2A) (SEQ ID NO: 20) all of which can optionally include the sequence GSG at the amino terminal end. This allows multiple transgenes to be transcribed onto a single transcript that is regulated by a 3'-UTR with an RDE (or multiple RDEs).

The bicistronic/multicistronic vector can increase the overall expression of the two or more cistrons (versus introducing the cistrons on separate constructs). The bicistronic/multicistronic construct can be derived from a lentivirus vector. The bicistronic/multicistronic construct can encode a CAR and a polypeptide(s) that is encoded on a transgene(s) (e.g., a payload), and the bicistronic construct may increase expression of the polypeptide encoded by the transgene(s) when the cell is activated by the CAR.

Expression constructs can be modified to remove an RNA splice site in a 5'-LTR of the construct so as to increase the transduction frequency of the expression construct. Many lentiviral transduction constructs have a residual splice site in the 5'-LTR that can reduce transduction frequency through splicing events with this site that alter the nucleic acids to be introduced. For example, lentiviral vectors represented by the pCDH vectors (System Biosciences), the lentiviral vectors pLVTH, pRRLSIN, pWPI, and pWPXL, as well as other lentiviral vectors contain a portion of the HIV 5'-LTR that includes a splice acceptor site. Removal of this splice site from the vectors increases transduction frequencies with the modified vectors (compared to the non-modified vectors). The splice donor site in the residual HIV 5'-LTR segment can be disrupted by making two nucleotide changes, G290C and U291A (numbering the HIV splice site according to Keane et al., Science 348:917-921 (2015), which is incorporated by reference in its entirety for all purposes). Other changes in this splice donor site could also be made to knock out this splice site. Other transduction vectors also include residual splice sites that can disrupt the desired sequence after transduction/transfection and removal of these splice sites should increase transduction/transfection frequencies with these vectors.

It may be desirable to modify polypeptides described herein. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, Gene 8:81-97, 1979; Roberts et al., Nature 328:731-734, 1987, which is incorporated by reference in its entirety for all purposes). The recombinant nucleic acids encoding the polypeptides of the invention can be modified to provide preferred codons which enhance translation of the nucleic acid in a selected organism.

The polynucleotides can also include polynucleotides including nucleotide sequences that are substantially equivalent to other polynucleotides described herein. Polynucleotides can have at least about 80%, more typically at least about 90%, and even more typically at least about 95%, sequence identity to another polynucleotide. The nucleic acids also provide the complement of the polynucleotides including a nucleotide sequence that has at least about 80%, more typically at least about 90%, and even more typically at least about 95%, sequence identity to a polynucleotide encoding a polypeptide recited herein. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., Angew Chem Intl Ed. 28:716-34, 1989 (which is incorporated by reference in its entirety for all purposes), may also be used to prepare such nucleic acids.

Amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Also disclosed herein are nucleic acids encoding a transgene, including a transgene encoding a CARS. The nucleic acid encoding the transgene can be easily prepared from an amino acid sequence of the specified CAR combined with the sequence of the RNA control device by a conventional method. A base sequence encoding an amino acid sequence can be obtained from the aforementioned NCBI RefSeq IDs or accession numbers of GenBenk for an amino acid sequence of each element, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acids can be linked to another nucleic acid so as to be expressed under control of a suitable promoter. The nucleic acid can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid is introduced into a cell ex vivo, the nucleic acid of may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful. Particularly, a composition in a form suitable for administration to a living body which contains the nucleic acid of the present invention carried by a suitable vector is suitable for in vivo gene therapy.

Introducing Nucleic Acids into Eukaryotic Cells

A process for producing a cell expressing a transgene includes a step of introducing the nucleic acid encoding the transgene described herein into a eukaryotic cell. This step can be carried out ex vivo. Exemplary methods for introducing nucleic acids to eukaryotic cells are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Virus Payloads

Viruses can be used to deliver transgenes to target cells. Viruses can carry nucleic acid constructs (e.g., transfer plasmids) as payloads and so deliver to a target cell desired nucleic acids for modification of the target cell genotype and/or phenotype (transiently or stably). In many of these transduction applications, the nucleic acid carried by the virus does not include all of the viral genome, and often includes the viral genome signals needed for packaging the nucleic acid construct into the virus without most or all of the rest of the viral genome. For example, lentiviral helper plasmid and transfer plasmids systems for transduction of target cells are available from addgene. Other helper and transfer plasmid systems are commercially available form a number of sources (e.g., Clontech/Takara).

When used as a payload, synthesis of viral capsids, packaging of payload nucleic acids, and release of virus with payload nucleic acids can be restricted to the target site by timing the expression of the virus genes for replication and coat proteins to binding of ligand by a receptor at the target site. Such control can be achieved using RDEs that induce expression when the cell undergoes a change in metabolic state (e.g., activation of glycolysis after receptor binding to target). This RDE control can regulate expression of master switch factors for expression of the virus genes. For example, a transcription regulatory factor can be placed under the control of a suitable RDE, and the viral genes for replication, coat proteins etc can be placed under the control of this transcription factor. When the host cell binds to ligand at the target site through an appropriate receptor (e.g., a CAR) this activates the cell, induces expression of the transcription factor with the appropriate RDE leading to expression of the viral replication proteins, coat proteins, etc.

Transduction with a Viral Vector

Transduction can be accomplished with a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. The virus vector can lack replicating ability so as not to self-replicate in an infected cell.

When a retrovirus vector is used to transduce the host cell, the process can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317

(ATCC CRL-9078), GP+E-86 and GP+envAm-12 (U.S. Pat. No. 5,278,056, which is incorporated by reference in its entirety for all purposes), and Psi-Crip (Proceedings of the National Academy of Sciences of the United States of America, vol. 85, pp. 6460-6464 (1988), which is incorporated by reference in its entirety for all purposes). A retrovirus particle can also be prepared using a 293 cell or a T cell having high transfection efficiency. Many kinds of retrovirus vectors produced based on retroviruses and packaging cells that can be used for packaging of the retrovirus vectors are widely commercially available from many companies.

A number of viral based systems have been developed for gene transfer into mammalian cells. A selected gene can be inserted into a vector and packaged in viral particles using techniques known in the art. The recombinant virus can then be isolated and delivered to cells of the subject either in vivo or ex vivo. A number of viral systems are known in the art. Adenovirus vectors can be used. A number of adenovirus vectors are known in the art and can be used. In addition, lentivirus vectors can be used.

A viral vector derived from a RNA virus can be used to introduce to a cell a RDE-CAR, Smart-RDE-CAR, DE-RDE-CAR, Smart-DE-RDE-CAR, and/or transgene-RDE encoding polynucleotides. The RNA virus vector can encode the reverse complement or antisense strand of the polynucleotide encoding the RNA control device and CAR construct (the complementary strand encodes the sense strand for the RNA control device, DE, RDE, CAR and/or Side-CAR construct). Thus, the RNA control device should not be active in the single stranded, RNA virus vector. The sense strand of the RNA virus construct encoding the RNA control device, DE, RDE, CAR, Side-CAR, and/or transgene can be used, and the viral vector with the RNA control device, DE, RDE, CAR and/or Side-CAR construct is maintained and replicated in the presence (or absence) of ligand for the sensor element of the RNA control device (or under conditions where the RDE is stable) to prevent cleavage of the RNA. The viral vector encoding the sense strand of the RNA control device, DE, RDE, CAR, Side-CAR, and/or transgene construct in the viral vector can then be maintained and replicated with (or without) ligand for the sensor element. Transduction efficiency can be increased by cryopreservation of packaged constructs prior to thawing and transduction. Increased efficiency ranged from about 10% to about 70%.

Pharmaceutical Compositions

Pharmaceutical compositions of the present invention may comprise a CARS and/or transgene-RDE expressing cell, e.g., a plurality of CARS and/or transgene-RDE expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. The pharmaceutically acceptable excipients described in Remington's Pharmaceutical Sciences (Mack Pub. Co., N.J. 1991) (which is incorporated herein by reference in its entirety for all purposes) can be appropriately used. The composition can be formulated into a known form suitable for parenteral administration, for example, injection or infusion. The composition may comprise formulation additives such as a suspending agent, a preservative, a stabilizer and/or a dispersant, and a preservation agent for extending a validity term during storage.

A composition comprising the eukaryotic cells described herein as an active ingredient can be administered for treatment of, for example, a cancer (blood cancer (leukemia), solid tumor (ovarian cancer) etc.), an inflammatory disease/autoimmune disease (pemphigus vulgaris, lupus erythematosus, rheumatoid arthritis, asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR, DE-CAR, and/or Side-CAR polypeptide binds.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, intranasally, intraarterially, intratumorally, into an afferent lymph vessel, by intravenous (i.v.) injection, or intraperitoneally. In one aspect, the T cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection. The administration can be done by adoptive transfer.

When "an immunologically effective amount," "an antitumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). A pharmaceutical composition comprising the eukaryotic cells described herein may be administered at a dosage of $10^4$ to $10^9$ cells/kg body weight, in some instances $10^5$ to $10^6$ cells/kg body weight, including all integer values within those ranges. A eukaryotic cell composition may also be administered multiple times at these dosages. Eukaryotic cells can also be administered by using infusion techniques that are commonly known in immunotherapy (see, e.g., Rosenberg et al., New Eng. J. of Med. 319:1676, 1988, which is incorporated by reference in its entirety for all purposes).

Uses of Eukaryotic Cells

Nucleic acids encoding CARS and/or transgene-RDE(s) can be used to express CAR, DE-CAR, Side-CAR, and/or transgene polypeptides in eukaryotic cells. The eukaryotic cell can be a mammalian cell, including for example human cells or murine cells. The eukaryotic cells may also be, for example, hematopoietic cells including, e.g., T-cells, natural killer cells, B-cells, or macrophages.

T-cells (e.g., CD4+ or CD8+) or natural killer cells can be engineered with a polynucleotide encoding a CAR. Ligand for the RNA control device, DE, or Side CAR is added to the T-cells (e.g., CD4+ or CD8+) or natural killer cells can be added in increasing amounts to obtain a desired amount of effector function. The desired amount of effector function can be an optimized amount of effector function with a known amount (and/or density) of target antigen on target cells. Effector function can be target cell killing, activation of host immune cells, cytokine secretion, production of granzymes, production of apoptosis inducing ligands, production of other ligands that modulate the immune system, etc. The effector function can be secretion of cytokines such as, for example, IL-2, IFN-γ, TNF-α, TGF-β, and/or IL-10. Effector function can be the killing of target cells. Target cells can be killed with granzymes. Target cells can be induced to undergo apoptosis. Eukaryotic cells with CARs can kill target cells through apoptosis and granzymes.

The RDE, DE, RNA control device, or Side CAR regulatory element can be used to control expression of a transgene. This transgene expression can deliver a payload at a target site. These transgenes can also be carried by viral constructs, or viruses when the payload is a virus. Expression of the transgene can cause a desired change in the eukaryotic cell. An RDE regulated by GAPDH can be used for payload delivery, and the eukaryotic cell (e.g., T-cell, natural killer cell, B-cell, macrophage, dendritic cell, or other antigen presenting cell) can be activated (e.g., by a CAR) when it reaches the target site. Upon activation of the eukaryotic cell at the target site through the CAR, the cell induces glycolysis and the GAPDH releases from the RDE allowed payload expression and delivery. The target site can be a tumor or infection and the transgene could encode a cytokine, a chemokine, an antibody, a checkpoint inhibitor, a granzyme, an apoptosis inducer, complement, an enzyme for making a cytotoxic small molecule, an enzyme that cleaves peptides or saccharides (e.g., for digesting a biofilm), other cytotoxic compounds, or other polypeptides that can have a desired effect at the target site. Checkpoint inhibitors include agents that act at immune checkpoints including, for example, cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3). Examples of checkpoint inhibitors that may be used as payloads include, for example, Nivolumab (Opdivo®), Pembrolizumab (Keytruda®), Cemiplimab (Libtayo®), Atezolizumab (Tecentriq®), Avelumab (Bavencio®), Durvalumab (Imfinzi®), Ipilimumab (Yervoy®), Lirilumab, and BMS-986016. Nivolumab, Atezolizumab and Pembrolizumab act at the checkpoint protein PD-1 and inhibit apoptosis of anti-tumor immune cells. Some checkpoint inhibitors prevent the interaction between PD-1 and its ligand PD-L1. Ipilimumab acts at CTLA4 and prevents CTLA4 from downregulating activated T-cells in the tumor. Lirilumab acts at KIR and facilitates activation of Natural Killer cells. BMS-986016 acts at LAG3 and activates antigen-specific T-lymphocytes and enhances cytotoxic T cell-mediated lysis of tumor cells.

The payload can be one or more of an anti-IL33 antibody, anti-LAG3 antibody, anti-TIM3 antibody, anti-TIGIT antibody, anti-MARCO antibody, anti-VISTA antibody, anti-CD39 antibody, anti-41BB antibody, IL-15, IL-21, IL-12, CD40L, and/or Leptin. The IL-33 receptor is upregulated in $T_{regs}$ (regulatory T-cells) and anti-IL33 antibody reduces proliferation and activation of $T_{regs}$. Anti-LAG3 antibody can also decrease activity of $T_{regs}$. Anti-Il33 antibody and anti-LAG3 antibody can be used alone or together to reduce the activity of $T_{regs}$ which can reduce the suppression of CAR T-cells and other anti-cancer T-cells. Anti-TIM-3 antibody allows co-localization of CD8+ T-cells and DC-1 cells (which improves anti-tumor response). MARCO is expressed on macrophages and in the tumor microenvironment this can be suppressive to T-cells. Anti-MARCO antibody prevents this tumor suppression by macrophages. Anti-VISTA antibody reduces the amount of neutrophils in the tumor microenvironment. A high neutrophil to T-cell ratio in the tumor microenvironment correlates with poor patient outcomes. Decreasing the neutrophils in the tumor can improve patient outcomes and tumor cell killing. IL-15 and Il-21 increase the expansion of natural killer cells and Il-15 can rescue CD8+ T-cells and may prevent T-cell exhaustion. CD40L plays a central role in priming, co-stimulation and activation of T-cells in an immune response. Anti-CD39 antibody can reduce adenosine levels in the tumor microenvironment. High levels of adenosine in the tumor microenvironment can induce immunosuppression. Anti-CD39 antibody can reduce this immunosuppression. Anti-41BB antibody can prevent T-cells from undergoing apoptosis and can also cause tumor cells to upregulate expression of PD1 (so can be combined with anti-PD1 therapies).

Cytokines can include, for example, IL-2, IL-12, IL-15, IL-18, IL-21, IFN-γ, TNF-α, TGF-β, and/or IL-10. Cytotoxic agents can include, for example, granzymes, apoptosis inducers, complement, or a cytotoxic small molecule. The payload can be a gene regulatory RNA, such as, for example, siRNA, microRNAs (e.g., miR155), shRNA, antisense RNA, ribozymes, and the like, or guide RNAs for use with CRISPR systems. The payload can be an anti-4-1BB antibody, anti-CD11b antibody, anti-CTLA4 antibody, anti-IL1b antibody, anti-IL33 antibody, anti-LAG3 antibody, anti-TIM3 antibody, anti-TIGIT antibody, anti-MARCO antibody, anti-VISTA antibody, anti-CD39 antibody, PGC-alpha, Leptin, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, Ox40-41BB, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), anti-CD28 antibody (including full length and fragments such as single chain antibodies), IL-21, Leptin, GOT2, NAMPT, CD56, IL-2 superkine, anti-REGNASE-1 payloads (e.g., miRNA), C-jun, cysteinase enzyme, cystinase enzyme, PCBP1 (poly(RC) binding protein 1), complement (one or more of B, C1-C9, D, C5b, C3b, C4b, C2a), BMP-1, anti-TGFb agents (e.g., anti-TGFb antibody, soluble TGFbR, anti-avB6 integrin antibody, natural TGFb binding proteins, small molecules such as GW788388, Tranilast, Losartan, HMG CoA reductase inhibitors, Imatinib mesylate, PPAR-g agonists, rosiglitazone, Pirfenidone, Halofuginone), IL7 combined with CCL19 (e.g., IL7-t2A-CCL19), dnTNFR2, dnTGFBR2, DCN, DKK1, OKT3, NOS2, CCL5, anti-4-1BB agonist Antibody, anti-CD11b, anti-CD28 agonist Ab, anti-CD29/anti-VEGF, anti-CTLA4 Ab, anti-IL1b Ab, BiTE, CCR2, CCR4/CXCL12 disruption, HAC, heparinase, HSP60, HSP70, hyaluronidase, IL-12, IL15, IL18, IL2, anti-CSF1R and anti-IGF1, anti-IL4, IL4 receptor antagonists, IL4 binders (e.g., soluble IL4R), soluble CD40 ligand (e.g., secreted ecto-CD40L), membrane CD40 ligand, a TGFBR antagonist, and/or 4-1BB ligand. The payloads can also include those found in US20190183932, which is incorporated by reference in its entirety for all purposes. The payload delivered at a target site (e.g., non-tumor target site) can be a factor that protects the target site such as, for example, an anti-inflammatory, a factor that attracts T-regulatory cells to the site, or cytokines or other factors that cause suppression and reduction in immune activity. The payload can be an enzyme that cleaves peptides or saccharides, for example hyaluronidase, heparanase, metalloproteinases and other proteinases which can be used, for example, to digest an undesired biofilm. Myeloid modifying payloads ("MM payloads") which reduce immune suppression or inhibition caused by myeloid cells may be delivered including, for example, ApoE3, ApoE4, Hsp60, Hsp70, TNFα, antagonists of CSF1 receptor, CD40L (CD154) and/or IL-12. Two or more MM payloads can also be delivered by the CAR, DE-CAR, side-CAR and/or other receptor cell (e.g., T-cell) using RDEs that produce different pharmacokinetics for delivery. For example, the different MM payloads could be controlled by different RDEs so that the Cmax of delivery for the different MM payloads occurs at different times. For example, Myeloid modifying payloads can promote activated M1 macrophages that are proinflammatory and tumoricidal. A MM payload that promotes M1 phenotypes are antagonists of CSF1R (antagonists that block and do not activate the CSF1 receptor and agents that bind CSF1 and prevent it from interacting with the CSF1R). Such antagonists of CSF1R include, for example, small-molecule inhibitors, PLX3397 (Pexidartinib, Plexxikon), PLX7486 (Plexxikon), ARRY-382 (Array Biopharma), INJ-40346527 (Johnson & Johnson), and BLZ945 (Novartis). Exemplary antibodies which are antagonists of CSF1R include, for example, Emactuzumab (Roche), AMG820 (Amgen), IMC-CS4 (LY3022855, Eli Lilly), and MCS110 (Novartis). Cannarile et al, J. Immunotherp. Cancer 5:53 (2017) which is incorporated by reference in its entirety for all purposes. The payload can be localized to the target cell (e.g., tumor site) by fusing or associating the payload with a Small Leucine Rich Proteoglycans (SLRPs) such as Decorin, Biglycan, or fibromodulaon/Lumican. The Decorin, Biglycan, or Lumican can bind to the collagen near the target cell and this binding will localize the payload at or near the target site. This strategy is particularly useful for keeping cytotoxic payloads localized to the target cells (e.g., a tumor). Decorin and Biglycan can also bind to TGF-beta at or near the target site and reduce suppression of the engineered T-cell, and so these can be used as a payload themselves to reduce TGFb. A Decorin, Biglycan, and/or lumican payload can also be constitutively expressed, or expressed under the control of an RDE with a moderate level of baseline expression (mimicking low level constitutive expression coupled with increased expression upon cell activation). The payload can be one or more of any of the above. The payload can be an imaging agent that allows the target site to be imaged. The payload may be a polypeptide that can be imaged directly, or it can be a polypeptide that interacts with a substrate to make a product that can be imaged, imaging polypeptides include, for example, thymidine kinase (PET), dopamine D2 (D2R) receptor, sodium iodide transporter (NIS), dexoycytidine kinase, somatostatin receptor subtype 2, norepinephrine transporter (NET), cannabinoid receptor, glucose transporter (Glutl), tyrosinase, sodium iodide transporter, dopamine D2 (D2R) receptor, modified haloalkane dehalogenase, tyrosinase, 0-galactosidase, and somatostatin receptor 2. These reporter payloads can be imaged using, for example, optical imaging, ultrasound imaging, computed tomography imaging, optical coherence tomography imaging, radiography imaging, nuclear medical imaging, positron emission tomography imaging, tomography imaging, photo acoustic tomography imaging, x-ray imaging, thermal imaging, fluoroscopy imaging, bioluminescent imaging, and fluorescent imaging. These imaging methods include Positron Emission Tomography (PET) or Single Photon Emission Computed Tomography (SPECT).

AB toxins can be used to engineer fusion payloads that deliver a desired protein product into a target cell. AB toxins include, for example diphtheria toxin, tetanus toxin, exotoxin A of *P. aeruginosa*, iota toxin Ia of *C. perfringens*, C2 toxin CI of *C. botulinum*, ADP-ribosyltransferase of *C. difficile*, etc. The AB toxin can be engineered to replace the catalytic (toxic) component (A domain) of the AB toxin with the desired protein so that the modified AB toxin binds its receptor and delivers the desired protein into a target cell through the B domain of the AB toxin. The B domain of AB toxins generally includes a receptor binding portion that binds to a feature on the target cell, and a transmembrane domain portion that forms a pore and interacts with target cell proteins to transport the A domain into the target cell. The B toxin fusions replace the A domain with a desired protein that the B domain will transport into the target cell through the B domain pore utilizing the cytosolic translocation factor complex (CTF) from the target cell.

These B toxin fusions can also be engineered to replace the receptor binding portion of the B domain with a binding domain (e.g., ligand) that binds to a desired antigen and/or receptor on a desired target cell. These modified B toxin fusions now bind to a desired target cell and then transport the desired protein into the target cell using the B domain pore and the CTF of the target cell. For example, the B toxin fusion could be engineered to bind to the antigen target of a CAR so that the B toxin fusion delivers payload from a CAR cell into a target cell (e.g., a tumor cell). The transgene payload can encode a cell penetrating peptide. The cell penetrating peptide can be fused to another protein to make a chimeric protein (aka fusion protein) in which the CPP portion guides the chimeric protein to the cytoplasm of a target cell.

Multiple systems are envisioned for use that can kill target cells directly. These include, for example, the introduction of a viral or a bacterial gene into target cells. This approach turns a non-toxic pro-drug to a toxic one. There are systems that have been extensively investigated: the cytosine deaminase gene ("CD") of *Escherichia coli*, which converts the pro-drug 5-Fluorocytosine ("5-FC") to 5-Fluorouracil ("5-FU"); and the herpes simplex virus thymidine kinase gene ("HSV-tk"), which converts ganciclovir ("GCV") to ganciclovir monophosphate, converted by the cancer cells' enzymes to ganciclovir triphosphate. The HSV-tk/GCV system useful in killing tumor cells directly, involves adenoviral transfer of HSV-tk to tumor cells, with the subsequent administration of ganciclovir. Specifically, recombinant replication-defective adenovirus is employed to transfer the thymidine, HSV-tk, into hepatocellular carcinoma ("HCC") cells to confer sensitivity to ganciclovir. Three useful HCC cell lines include, for example, Hep3B, PLC/PRF/5 and HepG2, which can efficiently infect, in vitro, by a recombinant adenovirus carrying lacZ reporter gene ("Ad-CMV-lacZ"). Expression of HSV-tk in HCC cells infected with a recombinant adenovirus carrying HSV-tk gene ("AdCMVtk") induces sensitivity to ganciclovir in a dose-dependent manner (Qian et al., Induction of sensitivity to ganciclovir in human hepatocellular carcinoma cells by adenovirus-mediated gene transfer of herpes simplex virus thymidine kinase, Hepatology, 22:118-123 (1995)) doi.org/10.1002/hep.1840220119.

When the payload is a gene regulatory RNA, such as, for example, siRNAs, shRNAs, and/or microRNAs (e.g., miR155), the regulatory RNA (e.g., mir155) can be the transgene or can be included in an intron of a transgene encoding a polypeptide. For example, a mir155 cassette as described in Du et al., FEBs J. 273:5421-27 (2006) and Chung et al., Nucl Acids Res. 34:e53 (2006) can be used as the payload or be engineered into an intron of a transgene that is used as the payload. The mir155 cassette (or cassette for other regulatory RNA) can be engineered into a transgene as an intron or the transgene can be the mir155 cassette, optionally with additional nucleotides. The regulatory RNA transgene (or transgene with regulatory RNA as an intron) can be placed under the control of an RDE. RDEs can impact RNA processing and stability in the nucleus. After the transgene encoding the regulatory RNA (e.g., mir155) or encoding a transgene with a regulatory RNA (e.g., mir155) intron is transcribed, the transcript can be processed in the nucleus by the nuclear microprocessor complex or other nuclear components to make the nucleotide stem-loop precursor regulatory RNA (e.g., pre-mir155). The pre-regulatory RNA (e.g., pre-mir155) stem-loop is exported out of the nucleus where it is processed by Dicer to form a short RNA duplex. The short RNA duplex(es) are bound by Argonaute (Ago) to form the core of the multi-subunit complex called the RNA-induced silencing complex (RISC). By operably linking a RDE to the transgene encoding the regulatory RNA (e.g., mir155) or the transgene with the regulatory RNA (e.g., mir155) intron, the expression of regulatory RNA (e.g., mir155) can be regulated by the RDE. Different RDEs can be operably linked to the regulatory RNA (e.g., mir155) transgene or transgene with regulatory RNA (e.g., mir155) intron to provide different timing and kinetics of expression following activation of a eukaryotic cell (e.g., activation of a T-cell by the TCR or a CAR). RDEs can be used that produce expression quickly after activation of the cell (e.g., AU2 or AU101), produce high expression 72-96 hours after activation (e.g., AU5 or AU21), or produce increasing expression through 192 hours after expression (e.g., AU19 or AU22). RDEs can also be selected that will produce continuous expression of regulatory RNA (e.g., mir155) or that will produce expression for a period of time after activation of the cell followed by reduced expression. Multiple regulatory RNA (e.g., mir155) constructs (e.g., with mir155 as the transgene or a transgene with a mir155 intron) with different RDEs can be used to provide continuous expression of regulatory RNA (e.g., mir155) following activation of a cell (e.g., T-cell) by using RDEs that provide different pharmacokinetic profiles of expression which together produce continuous expression (e.g., see Example 11). Alternatively, select RDEs or combinations of RDEs or combinations of regulatory RNA (e.g., mir155) with different RDEs can be used to provide a desired expression profile of the regulatory RNA (e.g., mir155).

Upregulation of mir155 has been associated with activated CD8+ T-cells and the formation of memory T-cells after an immunological challenge. Upregulation of mir155 expression during activation of T-cells (e.g., CAR T-cells activated by target antigens) will potentiate the CAR T-cell response against target cells. Placing mir155 under control of a heterologous RDE (e.g., an RDE that responds to GAPDH) ties upregulation of mir155 to activation of the T-cell so that mir155 is upregulated in activated T-cells (e.g., CD8+, CAR T-cells). This upregulation can increase proliferation of activated T-cells. The upregulation can also decrease T-cell exhaustion and senescence. The upregulation can also potentiate T-cell effector functions resulting in increased target cell killing.

Effector function of T-cells can also be enhanced by downregulating TCF7 and/or Tox expression and/or by upregulating IL-15 expression. TCF7 is a member of the T-cell factor/lymphoid enhancer-binding factor family of high mobility group (HMG) box transcriptional activators. This gene is expressed predominantly in T-cells and plays a critical role in natural killer cell and innate lymphoid cell development. HMG box protein TCF7 can be a regulator in the switch between self-renewal and differentiation. TCF7 can have a dual role in promoting the expression of genes characteristic of self-renewing CD34+ cells while repressing genes activated in partially differentiated CD34− state. TCF7 can regulate a network of transcription factors that switch cells from a naïve, undifferentiated state to a differentiated, effector cell state. When TCF7 is expressed cells adopt a self-renewal state that is more naïve and less differentiated. TCF7 can be downregulated using miRNAs such as, for example, mIR-192, mIR-34a, miR-133a, miR-138-5p, miR-342-5p, miR-491-5p, and/or miR-541-3p. In an example, one of more of these miRNAs can be encoded in one or more introns of a payload that are spliced out when the transcript is bound by hnRNPLL (see above), and when the payload is expressed in an activated cell making hnRNPLL these miRNAs will downregulate TCF7. Alternatively, a transgene encoding TCF7 can be used as an off switch for activated CAR T-cells. If TCF7 is expressed after the effector, CAR T-cell has killed the target cancer cells, this should push the CAR T-cell into a naïve, undifferentiated state (an off state for the CAR T-cell). The transgene encoding TCF7 could be placed under the control of an inducible promoter (e.g., an inducible promoter that is ligand inducible) or it could be placed under control of an RDE that results in expression after eight days or more of cell activation (e.g., see Example 11). Expression of TCF7 can be turned off by removal of ligand (or other inducing factors for the inducible promoter), and/or the RDE control will turn off expression. This can return the CAR T-cell to state where it can be reactivated by binding to target ligand at other cancer cells.

Thymocyte selection-associated high mobility group box (TOX) protein is a member of a small subfamily of proteins (TOX2, TOX3, and TOX4) that share almost identical HMG-box sequences. TOX can be induced by high antigen stimulation of the T cell receptor and TOX can be a central regulator of $T_{EX}$ (exhausted T-cells). Robust TOX expression can result in commitment to development of the $T_{EX}$ cell type. TOX exhaustion may counteract and balance T-cell overstimulation and activation-induced cell death in settings of chronic antigen stimulation. Effector T-cells (e.g., activated CD8+ T-cells) can have low Tox, whereas higher levels of Tox pushes the effector cells to become $T_{EX}$ cells. TEX cells have reduced effector function but are still effective against low level infections or small numbers of cancer cells.

Effector function of T-cells can be enhanced by including a payload encoding an miRNA for Tox (e.g., hsa-mir-26b-5p (MIRT030248) hsa-mir-223-3p (MIRT054680)) under regulation of an RDE. Following activation of the T-cell, the RDE control will result in expression of the miRNA for Tox. This miRNA will lower levels of Tox in the T-cell inhibiting $T_{EX}$ formation by the activated T-cells resulting in more active, effector T-cells against a target. In addition, a payload can be Tox itself, used as on off-switch that pushes the activated T-cells into a $T_{EX}$ phenotype at a desired time. When used as an off-switch, Tox expression can be under control of an inducible promoter that can be induced to express Tox at a desired time (e.g., by adding an appropriate ligand), Tox can be controlled by an RNA control device or a DE (ligand can induce expression), or Tox can be placed under control of an RDE that produces expression at late time intervals after activation of the cell (e.g., see Example 11). Functional state and type of T-cell can tailored by treating T-cells with electromagnetic radiation. Electromagnetic radiation in the UV range can condition T-cells to become Treg cells. For example, a dose of UVA/UVB can induce formation of Tregs. Electromagnetic radiation in the blue light range can activate T-cells.

An exemplary payload is a transgene encoding ApoE (e.g., ApoE2, ApoE3 and/or APoE4) which is secreted from the cell. ApoE can bind to receptors (e.g., LRP8) on Myeloid Derived Suppressor Cells (MDSC) and reduce the survival of MDSCs. MDSCs are a heterogeneous population of suppressive innate immune cells that can expand in certain disease states. In some cancers (e.g., melanoma, lung, breast and ovarian cancers) MDSC levels can substantially rise in the tumor(s) and in the plasma of patients. Such patients with high levels of circulating MDSCs can respond poorly to checkpoint blockade. MDSCs can mediate immunosuppression in these patients and induce angiogenesis. Payload expression of ApoE (e.g., ApoE4) can reduce the number of MDSCs in tumors and circulating in the serum, and result in suppression of tumor progression and metastatic colonization. The reduction in MDSCs in the tumor also enables other immune cells (e.g., CAR T-cells) to more efficiently kill tumor cells. The ApoE payload can also act directly on myeloid malignancies that express the LRP8 receptor. In such examples, the payload delivery of ApoE to a myeloid cancer cell can suppress and/or kill the cancer cell. Thus, ApoE can be a payload for delivery to myeloid malignancies that are LRP8+, including LRP8+AML. Delivery of the ApoE payload by a eukaryotic cell (e.g., primary T-cell) can be combined with another therapeutic agent such as, for example, an anti-cancer agent (e.g., a CAR T-cell, a chemotherapeutic, radiation, a checkpoint inhibitor, or any of the anti-cancer therapeutics described herein). The ApoE effect on MDSCs can potentiate the action of the other anti-cancer agent.

Another exemplary payload is a transgene encoding NO-synthase (e.g., iNOS, nNOS and eNOS). NO synthase can bind to GAPDH and can sequester the GAPDH allowing RDE (which are bound by GAPDH) controlled transgenes (or native genes) to be expressed, or increasing expression from RDE (which are bound by GAPDH, e.g., AU 19 (TMEM-219), AU 20 (TMEM-219snp), AU 21 (CCR7), AU 22 (SEM-A4D), and AU 23 (CDCl42-SE2)) controlled transgenes (or native genes) once the cell is activated and glycolysis is induced. Expression of NO synthase can induce RDE (which are bound by GAPDH) controlled expression (through binding to GAPDH) and/or can potentiate RDE (which are bound by GAPDH) controlled expression by decreasing the amount of GAPDH that can bind RDEs and/or increasing the time over which GAPDH cannot bind to RDEs. When NO synthase is used to increase the RDE (which are bound by GAPDH) response to cell activation, a transgene encoding NO synthase can be placed under control of an RDE so that when the cell is activated, expression from the transgene encoding the NO synthase is induced. When NO synthase is used to induce expression from RDE (which are bound by GAPDH) controlled genes, the NO synthase can be placed under inducible control (e.g., inducible promoters, RNA control devices, or destabilizing elements as disclosed in U.S. Pat. No. 9,777,064, which is hereby incorporated by reference in its entirety for all purposes) and induction of NO synthase expression induces expression from the RDE (which are bound by GAPDH) controlled genes.

An exemplary payload is a transgene encoding HSV-Thymidine Kinase (HSV-TK). HSV-TK can be used as an adjuvant, and/or as a super antigen that induces an inflammatory response in the patient. When used in this manner, a cell secretes the HSV-TK payload at the target site inducing an inflammatory response. The transgene encoding the HSV-TK can also be used as a kill switch to eliminate the engineered cells (e.g., CAR T-cells with or without a RDE controlled payload). When used as a kill switch, the HSV-TK can be controlled by a late expressing RDE so the HSV-TK is expressed after the CAR T-cell has acted at the target site, or the transgene expressing the HSV-TK can be controlled by a ligand inducible control means so that the HSV-TK protein is expressed in response to the ligand which is introduced at a desired time. In the kill-switch application, ganciclovir can be provided to the cells and the HSV-TK converts the ganciclovir to GCV-triphosphate which kills the cell by a cytotoxic effect. A transgene expressing HSV-TK can also be included in a viral payload so that when the virus infects target cells the target cells express HSV-TK. Ganciclovir is provided to the target cells which use the HSV-TK to convert the ganciclovir to GCV-triphosphate which is toxic to the target cells.

Thymidine kinase can be used with PET reporter probes such as, for example, $[^{18}F]$9-(4-$[^{18}F]$-fluoro-3-hydroxymethylbutyl)-guanine, a fluorine-18-labelled penciclovir analogue, which when phosphorylated by thymidine kinase (TK) becomes retained intracellularly, or is 5-(76) Br-bromo-2'-fluoro-2'-deoxyuridine. The relevant reporter probes for each of the PET reporters are well known to the skilled artisan. An exemplary reporter probe for dopamine D2 (D2R) receptor is 3-(2'-$[^{18}F]$fluoroethyl)spiperone (FESP) (MacLaren et al., Gene Ther. 6(5):785-91 (1999)). An exemplary reporter probe for the sodium iodide transporter is $^{124}$I, which is retained in cells following transport by the transporter. An exemplary reporter probe for deoxycytidine kinase is 2'-deoxy-2'-$^{18}$F-5-ethyl-1-β-d-arabinofuranosyluracil ($^{18}$F-FEAU). An exemplary reporter probe for somatostatin receptor subtype 2 is $^{111}$In-, $^{99m/94m}$Tc-, $^{90}$Y-, or $^{177}$Lu-labeled octreotide analogues, for example $^{90}$Y-, or $^{177}$Lu-labeled DOTATOC (Zhang et al., J Nucl Med. 50(suppl 2):323 (2009)); $^{68}$Ga-DOTATATE; and $^{111}$In-DOTABASS (see. e.g., Brader et al., J Nucl Med. 54(2):167-172 (2013), incorporated herein by reference). An exemplary reporter probe for norepinephrine transporter is $^{11}$C-m-hydroxyephedrine (Buursma et al., J Nucl Med. 46:2068-2075 (2005)). An exemplary reporter probe for the cannabinoid receptor is $^{11}$C-labeled CB2 ligand, $^{11}$C-GW405833 (Vandeputte et al., J Nucl Med. 52(7):1102-1109 (2011)). An exemplary reporter probe for the glucose transporter is $[^{18}F]$fluoro-2-deoxy-d-glucose (Herschman, H. R., Crit Rev Oncology/Hematology 51:191-204 (2004)). An exemplary reporter probe for tyrosinase is N-(2-(diethylamino)ethyl)-$^{18}$F-5-fluoropicolinamide (Qin et al., Sci Rep. 3:1490 (2013)). Other reporter probes are described in the art, for example, in Yaghoubi et al., Theranostics 2(4):374-391 (2012), incorporated herein by reference.

An exemplary photoacoustic reporter probe for β-galactosidase is 5-bromo-4-chloro-3-indolyl-β-D-galactoside (X-gal) (Li et al., J Biomed Opt. 12(2):020504 (2007)). Exemplary X-ray reporter includes, among others, somatostatin receptor 2, or other types of receptor based binding agents. The reporter probe can have a radiopaque label moiety that is bound to the reporter probe and imaged, for example, by X-ray or computer tomography. Exemplary radiopaque label is iodine, particularly a polyiodinated chemical group (see, e.g., U.S. Pat. No. 5,141,739), and paramagnetic labels (e.g., gadolinium), which can be attached to the reporter probe by conventional means. Optical imaging agents include, for example, a fluorescent polypeptide. Fluorescent polypeptides include, for example, green fluorescent protein from *Aequorea victoria* or *Renilla reniformis*, and active variants thereof (e.g., blue fluorescent protein, yellow fluorescent protein, cyan fluorescent protein, etc.); fluorescent proteins from Hydroid jellyfishes, Copepod, Ctenophora, Anthrozoas, and Entacmaea quadricolor, and active variants thereof; and phycobiliproteins and active variants thereof. The optical imaging agent can also be a bioluminescent polypeptide. These include, for example, aequorin (and other Ca' regulated photoproteins), luciferase based on luciferin substrate, luciferase based on Coelenterazine substrate (e.g., *Renilla, Gaussia*, and Metridina), and luciferase from Cypridina, and active variants thereof.

CARS and/or universal-CARs can be designed to include receptors against antigens that are of bacterial, fungal or viral origin. Because CARS can be utilized to fight infections, which are a source of toxicity in immunocompromised patients, such anti-pathogen CARS can be used in conjunction with CARS T-cell therapy specific for a TAA.

A eukaryotic cell can bind to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell can be activated and so express an appropriate RDE-transgene. The activation of the eukaryotic cell expressing the CARS is varied depending on the kind of a eukaryotic cell and the intracellular element of the CARS. The eukaryotic cell can express a RDE transcript that poises the cell for effector function upon stimulation of the eukaryotic cell through a CARS.

A eukaryotic cell expressing the RDE-transgene or RDE transcript, and optionally, a CARS, T-cell receptor, B-cell receptor, innate immunity receptor and/or other receptor or targeting polypeptide can be used as a therapeutic agent to treat a disease. The therapeutic agent can comprise the eukaryotic cell expressing the RDE-transgene or RDE transcript, and optionally, a CARS, T-cell receptor, B-cell receptor, innate immunity receptor and/or other receptor or targeting polypeptide as an active ingredient, and may further comprise a suitable excipient. Examples of the excipient include pharmaceutically acceptable excipients for the composition. The disease against which the eukaryotic cell expressing the RDE-transgene or RDE transcript, and optionally, a CARS, T-cell receptor, B-cell receptor, innate immunity receptor and/or other receptor or targeting polypeptide is administered is not particularly limited as long as the disease shows sensitivity to the eukaryotic cell and/or the product of the RDE-transgene.

Examples of diseases that can be treated include a cancer (blood cancer (leukemia), solid tumor (ovarian cancer) etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis, other immune mediated diseases such as neurodegenerative diseases like Alzheimer's or Parkinson's, and metabolic diseases like diabetes. A receptor (e.g., a CAR) can target the eukaryotic cell to the diseased cell(s) and when the receptor binds to its target at the diseased cell(s) the receptor can send a signal into the eukaryotic cell leading to expression of the RDE-transgene. The RDE-transgene encodes a polypeptide that is useful in treating or killing the diseased cell(s). A cancer and/or solid tumor can be treated with a eukaryotic cell expressing receptor that binds to a tumor associated (or cancer associated) antigen, such as those described above. When the receptor binds to the tumor associated antigen the receptor sends a signal into the cell that causes the RDE-transgene to be expressed (e.g., the signal effects an RDE binding protein leading to expression of the RDE-transcript). The RDE-transcript can encode a polypeptide that activates the eukaryotic cell so that the eukaryotic cell treats the cancer and/or the RDE-transcript encodes a polypeptide that itself treats the cancer (e.g., a cytotoxic polypeptide).

An autoimmune disease (e.g., pemphigus vulgaris, lupus erythematosus, rheumatoid arthritis, multiple sclerosis, Crohn's disease) can be treated with a eukaryotic cell expressing a RDE-transgene or RDE transcript, and optionally, a CARS, T-cell receptor, B-cell receptor, innate immunity receptor and/or other receptor or targeting polypeptide that binds to the immune proteins associated with the autoimmune disease. The receptor or targeting polypeptide can trigger expression of the RDE-transgene that encodes a polypeptide useful in treating the autoimmune disease (e.g., the polypeptide can regulate the cells causing the autoimmune disease or kill these cells). The eukaryotic cell expressing the RDE-transgene or RDE transcript, and receptor or targeting polypeptide can target cells that make an antibody involved with the autoimmune disease (e.g., the RDE-transgene can encode a polypeptide that kills the antibody producing cells or that inhibits the production of antibody by these cells). The eukaryotic cell expressing the RDE-transgene or RDE transcript, and receptor or targeting polypeptide can target T-lymphocytes involved with the autoimmune disease (e.g., the RDE-transgene can encode a polypeptide that kills the target T-lymphocytes or that regulates the activity of the T-lymphocytes).

Eukaryotic cells expressing the RDE-transgene or RDE transcript, and optionally, a CARS, T-cell receptor, B-cell receptor, innate immunity receptor and/or other receptor or targeting polypeptide can be used as a therapeutic agent to treat an allergy. Examples of allergies that can be treated include, for example, allergies to pollen, animal dander, peanuts, other nuts, milk products, gluten, eggs, seafood, shellfish, and soy. The eukaryotic cell expressing the RDE-transgene or RDE transcript, and receptor or targeting polypeptide can target cells that make an antibody which causes the allergic reaction against, for example, pollen, animal dander, peanuts, other nuts, milk products, gluten, eggs, seafood, shellfish, and soy. The targeted cells can be one or more of B-cells, memory B-cells, plasma cells, pre-B-cells, and progenitor B-cells. Targeted cells can also include T-lymphocytes which cause the allergic reaction against, for example, pollen, animal dander, peanuts, other nuts, milk products, gluten, eggs, seafood, shellfish, and soy. Eukaryotic cells expressing the RDE-transgene or RDE transcript, and receptor or targeting polypeptide can bind to the idiotypic determinant of the antibody or T-cell receptor.

The eukaryotic cell expressing the RDE-transgene or RDE transcript, and optionally, a CARS, T-cell receptor, B-cell receptor, innate immunity receptor and/or other receptor or targeting polypeptide can be administered for treatment of a disease or condition. For example, the eukaryotic cell can be utilized to treat an infectious disease. The eukaryotic cell can express a receptor or targeting polypeptide that binds to an antigen found on the infectious disease causing agent or a cell infected with such an agent. The receptor or targeting polypeptide binds the antigen associated with the infectious disease and sends a signal into the eukaryotic cell that leads to expression of the RDE-transgene. The RDE-transgene encodes a product that can activate the eukaryotic cell for treating the infectious disease (e.g., the eukaryotic cell can produce a cytotoxic polypeptide or a cytokine that activates immune cells). The RDE-transgene can also encode a polypeptide that itself is a cytotoxic polypeptide or a cytokine. The eukaryotic cell can also be utilized for prevention of an infectious disease (used prophylactically), for example, after bone marrow transplantation or exposure to radiation, donor lymphocyte transfusion for the purpose of remission of recurrent leukemia, and the like.

The therapeutic agent comprising the eukaryotic cell expressing the CARS, T-cell receptor, B-cell receptor, innate immunity receptor and/or other receptor or targeting polypeptide as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

The RDE-transgene or RDE transcript, and optionally, CARS, T-cell receptor, B-cell receptor, innate immunity receptor and/or other receptor or targeting polypeptide can be used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. The RDE transcript can encode a polypeptide that causes aggressive anti-tumor properties in the T-lymphocyte.

A transgene, a CAR, DE-CAR, and/or Side CAR polypeptides can be controlled by an RDE from the 3'-UTR of the gene encoding IL-2 or the 3'-UTR of IFN-γ. These RDEs can be modified to inactivate microRNA sites found in the RDE. Using these control elements makes expression of the CAR, DE-CAR, Side-CAR, and/or transgene sensitive to changes in the glycolytic state of the host cell through the interaction of the RDE with glyceraldehyde-3-phosphate dehydrogenase (GAPDH). When the host cell is in a quiescent state a large proportion of the GAPDH is not involved in glycolysis and is able to bind to the RDE resulting in reduced translation of the transcript encoding the CAR, DE-CAR, Side-CAR, and/or transgene polypeptides. When the host cell is induced to increase glycolysis, e.g., by providing the host cells with glucose, or other small molecules that will increase glycolytic activity, GAPDH becomes enzymatically active and is not able to bind to the RDE. The reduction in GAPDH binding to the RDE increases translation of the transcripts (e.g., by increasing half-life of the transcript and/or by increasing the translation rate) encoding the CAR, DE-CAR, Side-CAR, or other transgene. The glycolytic activity of GAPDH can be increased by increasing the amount and/or activity of triose isomerase. The host cell can be induced to over-express a recombinant triose isomerase, and this over-expression increases the glycolytic activity of GAPDH. A glycolysis inhibitor can be added to decrease expression of the transcript with the RDE. Such glycolysis inhibitors include for example, dimethylfumarate (DMF), rapamycin, 2-deoxyglucose, 3-bromophyruvic acid, iodoacetate, fluoride, oxamate, ploglitazone, dichloroacetic acid, quinones (e.g., chloroquine, hydroxychloroquine, etc.), or other metabolism inhibitors such as, for example, dehydroepiandrosterone. Expression from the RDE controlled transcript can be increased by the addition of GAPDH (or other RDE binding protein) inhibitor that inhibits binding of the RDE by GAPDH (or other RDE binding protein). Such GAPDH inhibitors include, for example, CGP 3466B maleate or Heptelidic acid (both sold by Santa Cruz Biotechnology, Inc.), pentalenolactone, or 3-bromopyruvic acid. Quinones such as, for example, chloroquine and hydroxychloroquine, can de-acidify the endosome impairing antigen processing by APCs, decrease signaling from toll-like receptors, reduces T-cell proliferation, T-cell metabolic activity, T-cell cytokine secretion, interferes with IL-2 production, and interferes with T-cell response to IL-2.

Constructs encoding transcripts with RDEs can be expressed in eukaryotic cells to bind to RDE binding proteins and so reduce the ability of those RDE binding proteins to interact with native transcripts in the cell. The recombinant transcripts can compete for binding of RDE binding proteins and this can reduce the inhibition and/or activation of native transcripts within the eukaryotic cell by the RDE binding proteins. The constructs encoding transcripts with the RDEs can be used in this way to change when and how native transcripts are expressed in the eukaryotic cell. The eukaryotic cell can be a T-cell, natural killer cell, or B-cell and the recombinant transcript has RDEs that are shared with cytokine or cytotoxic transcripts (e.g., in their 3' untranslated regions). The recombinant transcript can compete for binding with the RDE binding proteins (e.g., GAPDH and/or other glycolytic enzymes described above) that regulate expression of the cytokine or cytotoxic polypeptide and change the threshold (e.g., glycolysis activity for GAPDH) needed to express the cytokine or cytotoxic polypeptide. This can be used to create super T-cell (aka Angry T-cells or Hornet T-cells) that will secrete higher amounts of cytokines and/or cytotoxic proteins (greater $C_{max}$) in response to stimulation of the immune cell (e.g., through a CAR or T-cell receptor). T-cells can be reprogrammed with a recombinant transcript encoding an RDE from an IL-2 transcript so that when the T-cell is stimulated by its T-cell receptor it produces more IL-2 and other effector polypeptides with faster kinetics. These reprogrammed T-cells can also produce other inflammatory cytokines and cytotoxic polypeptides (e.g., granzymes and/or perforins) in larger amounts and with faster kinetics. Reprogramming T-cells and natural killer cells into such Angry/Hornet states can be useful for treating disease and disorders, including, for example, tumors, other cancers, and infectious diseases.

RDEs can be used to reduce CAR expression in immune cells until those immune cells are activated by target or at a desired time. This can result in expression of the CAR at desired times for therapeutic effect while reducing the systemic exposure of a subject to the CAR. The reduced systemic exposure can reduce and/or inhibit the development of an immune response against the CAR as the subject's immune system will see less CAR over time.

Control of receptor (e.g., CAR and/or TCR) expression can be used to modulate the PK-PD axis of an immunotherapy. The amount of receptor expressed on the surface of cell can be modulated with the strength of a promoter, the inducibility of the promoter, the use of bicistronic constructs with different promoter strengths expressing the two cistrons, RDEs (selection of RDE impacts dynamic range and timing of expression), GC3 content of the transcript, RNA control devices, degrons and/or Side-CARs. These control elements used singly or in combination change the amount of receptor on the surface of the cell which changes the input signal (e.g., amount of ligand for the receptor) needed to activate the cell so that it produces an output (e.g., payload delivery or target cell killing). Using this control, the input signal needed for the receptor cells can be optimized for a given target, compartment of the body, reduction of side effects, etc. as desired. RDEs can also be used to change the timing of the output from the cell after activation at the receptor (e.g., CAR and/or TCR).

Some neural degenerative diseases and syndromes are associated with inflammation, as are a number of other non-neural diseases and syndromes. Such inflammation associated diseases can be treated, at least in part, by providing a subject with small molecules (or other molecules) that increase the availability of inhibitory RDE binding proteins within immune cells. Such small molecules include, for example, glycolysis inhibitors (e.g., dimethylfumarate (DMF), rapamycin, 2-deoxyglucose, 3-bromophyruvic acid, iodoacetate, fluoride, oxamate, ploglitazone, dichloroacetic acid), other metabolic inhibitors (e.g., dehydroepiandrosterone), etc. For example, glycolytic inhibitors reduce glycolysis in the cell and can increase the amount of free GAPDH (not involved in glycolysis) for binding to RDEs reducing the expression of these transcripts. A number of inflammatory gene products in immune cells (e.g., gene products that activate the immune system) are regulated by RDEs that can bind GAPDH. Decreasing glycolysis increases the amount of free GAPDH for RDE binding, increases the amount of GAPDH bound to the RDEs of these inflammatory genes and reduces the expression of these inflammatory genes. Inflammatory genes include proinflammatory cytokines such as, for example, IL-1, TNF-α, INF-g, and GM-CSF. These cytokines have 3'-UTRs with RDEs that can bind RDE binding proteins, including GAPDH, to regulate their expression. The increased GAPDH can bind to these RDEs and decrease the expression of these proinflammatory cytokines. Reduced expression of proinflammatory cytokines could reduce activity of the immune system in these subjects reducing inflammation. The reduction in inflammation can have positive therapeutic effects alleviating symptoms and/or treating the underlying disease state in these inflammation related neural diseases, as well as in other inflammation associated diseases and syndromes.

RDEs (e.g., AU elements) can be selected to provide maximal expression at a desired time point and to provide a desired amount of polypeptide at that time point. RDEs can also be selected to provide a desired area under the curve for a polypeptide. As shown in Table 2 of Example 20, different RDEs (e.g., AU elements) reached maximal rates of expression at different times. Also as shown in Table 1, different RDEs provided different amounts of expression with different profiles over time providing different AUC. Using these RDEs in combination with different transgenes allows temporal programming of when the different transgenes reach maximal rates of expression in relation to one another following activation of a cell. In addition, using different RDEs one can program the transgenes to express a desired amount of transgene encoded polypeptide and/or a desired amount of AUC or exposure to the polypeptide encoded by the transgene. Thus, RDEs can be used to provide control that produces desired amounts of different transgene polypeptides at a different (or the same) desired times.

This temporal control can be used to provide desired timing for the production of different transgene polypeptides within a cell. Using this temporal control, a cell can be programmed to express a first transgene that alters the state of the cell so that is prepared to be affected by the polypeptide of a second transgene that is expressed at a later time. For example, the first expressed polypeptide could induce the cell to make and store cytotoxic polypeptides (e.g., granzymes and/or perforins) and the second expressed polypeptide could be involved in the release of the cytotoxic polypeptides. Another example of temporal expression involves it use to program a cell to undergo changes (e.g., differentiation or changing a state of the cell) that requires temporal expression of two or more gene products. RDEs can be used to mimic this temporal expression allowing one to control when the cell changes its state or differentiates (e.g., programmed differentiation of stem cells). In a stem cell example, the temporal and induction control can be used to program a stem cell to differentiate when (and where) it is desired to have the stem cell differentiate into a desired cell type.

The temporal control can also be used to provide desired timing of the production of different transgene polypeptides outside of the cell. Using this temporal control, a cell can be activated and secrete a first transgene polypeptide that conditions and/or alters a target cell so that the target cell is prepared to be acted upon by a polypeptide expressed at later time from a second transgene. For example, the first polypeptide could induce a target cell to express a receptor on the target cell surface (e.g., FasR, Her2, CD20, CTLA-4, PD-L1, etc.) or a polypeptide in the cell. The first transgene could also induce the cell to secrete a factor that induces the target cell to change its state (e.g., the first transgene could induce the cell to secrete CpG which causes the target cell to express OX40 on the target cell surface). The second transgene that reaches maximal rate of expression at a later time can encode a polypeptide that acts on the induced surface receptor (e.g., FasL, Herceptin, Rituximab, Ipilimumab, Nivolumab, anti-OX40 antibody, etc.). The temporal and induction control can also be used to change the state or differentiation of a target cell by providing to the target cell polypeptides in a timed manner where the first polypeptide induces the target cell to alter its state (e.g., differentiation) so that it can be acted upon by the second polypeptide (etc. for additional transgene polypeptides which reach maximal rate of expression at later times).

Autoimmune diseases and other disease states involving an overactive immune system (e.g., SARS-CoV-2 infection) can be treated with a AITAM CAR T-cell targeted against autoimmune disease antigen(s). The AITAM CAR T-cell can include a payload of IL-4, IL-10 or other immunosuppressive. The AITAM CAR T-cell with or without a payload can induce the formation of Tregs that can inhibit the autoimmune disease and/or reduce the toxicity caused by overstimulation or chronic stimulation of the immune system.

Some examples of diseases and payloads that can be treated using RDEs (Gold elements) with different kinetic parameters (e.g., an RDE that gives rapid expression early after activation of the cell followed by a rapid decline in expression or an RDE that delays expression after cell activation for 2-3 days) include the following: DLL3 positive cancers (such as IDH1mut gliomas, melanoma, and SCLC) using an anti-DLL3 CAR and a payload of one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-12, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-DLL3 CAR with an RDE controlled payload is combined or administered in succession with another therapy as described above. The combined or sequenced therapy can be an ADC where the antibody binds to a tumor associate antigen, e.g., DLL3. The combination therapy can be provided to a subject prior to, at the same time, or after the administration of the anti-DLL3 CAR with an RDE controlled payload. CD19 positive lymphomas (e.g., NHL) using an anti-CD19 CAR and a payload of IL-12, or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-CD19 CAR with an RDE controlled payload is combined or administered in succession with another therapy as described above. The combined or sequenced therapy can be an ADC where the antibody binds to a tumor associate antigen, e.g., CD19. The combination therapy can be provided to a subject prior to, at the same time, or after the administration of the anti-CD19 CAR with an RDE controlled payload. AML with onco-CD43 (sialylation mutant) using an anti-onco-CD43 CAR that recognizes the mutated sialylation and a payload of one or more of anti-CXCL12 antibody, anti-anti-CXCR4 antibody, or IL-12, and/or one or more of anti-4-1BB antibody, anti-CD11b antibody, anti-CTLA4 antibody, anti-IL1b antibody, a BiTE, CCL2, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-onco-CD43 CAR with an RDE controlled payload is combined or administered in succession with another therapy as described above. The combined or sequenced therapy can be an ADC where the antibody binds to a tumor associated antigen, e.g., onco-CD43. The combination therapy can be provided to a subject prior to, at the same time, or after the administration of the anti-onco-CD43 CAR with an RDE controlled payload. PSCA positive prostate cancer, bladder cancer or pancreatic cancer using an anti-PSCA CAR and a payload of heparinase or IL-12, and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-PSCA CAR with an RDE controlled payload is combined or administered in succession with another therapy as described above. The combined or sequenced therapy can be an ADC where the antibody binds to a tumor associated antigen, e.g., PSCA. The combination therapy can be provided to a subject prior to, at the same time, or after the administration of the anti-PSCA CAR with an RDE controlled payload. Triple negative breast cancer with a CAR that recognizes cancer testis antigen, misfolded or mutant EGFR (associated with triple negative breast cancer), and/or folate receptor alpha peptide and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-cancer testis antigen CAR, anti-misfolded or mutant EGFR CAR, or anti-folate receptor alpha CAR with an RDE controlled payload is combined or administered in succession with another therapy as described above. The combined or sequenced therapy can be an ADC where the antibody binds to a tumor associated antigen, e.g., cancer testis antigen, misfolded or mutant EGFR (associated with triple negative breast cancer), and/or folate receptor alpha peptide. The combination therapy can be provided to a subject prior to, at the same time, or after the administration of the anti-cancer testis antigen CAR, anti-misfolded or mutant EGFR CAR, or anti-folate receptor alpha CAR with an RDE controlled payload. SEZ6 positive small cell lung cancer (SCLC), neuroendocrine cancers (e.g., medullary thyroid cancer), large cell lung cancer (LCLC), and malignant pheochromocytoma with a CAR that recognizes SEZ6 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-SEZ6 CAR with an RDE controlled payload is combined or administered in succession with another therapy as described above. The combined or sequenced therapy can be an ADC where the antibody binds to a tumor associated antigen, e.g., SEZ6. The combination therapy can be provided to a subject prior to, at the same time, or after the administration of the anti-SEZ6 CAR with an RDE controlled payload. RNF43 positive colorectal cancer, colon cancer, and endometrial cancers with a CAR that recognizes RNF43 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-RNF43 CAR with an RDE controlled payload is combined or administered in succession with another therapy as described above. The combined or sequenced therapy can be an ADC where the antibody binds to a tumor associated antigen, e.g., RNF43. The combination therapy can be provided to a subject prior to, at the same time, or after the administration of the anti-RNF43 CAR with an RDE controlled payload. TnMUC1 positive breast cancer or pancreatic cancer with a CAR that recognizes TnMUC1 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-TnMUC1 CAR with an RDE controlled payload is combined or administered in succession with another therapy as described above. The combined or sequenced therapy can be an ADC where the antibody binds to a tumor associated antigen, e.g., TnMUC1. The combination therapy can be provided to a subject prior to, at the same time, or after the administration of the anti-TnMUC1 CAR with an RDE controlled payload. Nectin4 positive urothelial cancer, NSCLC, breast cancer, ovarian cancer, bladder cancer, pancreatic cancer, and other solid tumors with a CAR that recognizes Nectin4 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-Nectin4 CAR with an RDE controlled payload is combined or administered in succession with another therapy as described above. The combined or sequenced therapy can be an ADC where the antibody binds to a tumor associated antigen, e.g., Nectin4. The combination therapy can be provided to a subject prior to, at the same time, or after the administration of the anti-Nectin4 CAR with an RDE controlled payload. EFNA4 positive triple negative breast cancer, ovarian cancer, colorectal cancer, liver cancer, lung cancer, and other solid tumors with a CAR that recognizes EFNA4 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-EFNA4 CAR with an RDE controlled payload is combined or administered in succession with another therapy as described above. The combined or sequenced therapy can be an ADC where the antibody binds to a tumor associated antigen, e.g., EFNA4. The combination therapy can be provided to a subject prior to, at the same time, or after the administration of the anti-EFNA4 CAR with an RDE controlled payload. GPC3 positive hepatocellular carcinoma, lung cancer and other solid tumors with a CAR that recognizes GPC3 and a payload of IL-12 and/or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies). Optionally, the anti-GPC3 CAR with an RDE controlled payload is combined or administered in succession with another therapy as described above. The combined or sequenced therapy can be an ADC where the antibody binds to a tumor associated antigen, e.g., GPC3. The combination therapy can be provided to a subject prior to, at the same time, or after the administration of the anti-GPC3 CAR with an RDE controlled payload.

In general, any of the above CAR cells with or without an RDE controlled transgene(s) can be used in combination or administered in succession with another molecule (e.g., another therapy). For example, the other molecule can be a polypeptide, lipid, carbohydrate, nucleic acid, small molecule drug, antibody, antibody-drug-conjugate, biological drug, or any combination of the foregoing. The antibody drug conjugate (ADC) includes those described herein. The ADC can bind to the same antigen as the CAR or it can bind to a different antigen. When the ADC and CAR bind to the same antigen, they may bind to the same or different epitopes on the same antigen. The ADC and CAR therapy (with or without a RDE controlled payload) can be provided at the same time, or one can be administered to a subject before the other. For example, the ADC and CAR can target a tumor associate antigen and the ADC can be administered the subject first to reduce the tumor burden, and then the CAR therapy is administered to clear the remaining cancer cells.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1. Control of T-Cell Effector Activity with an RDE-CAR

A RDE Car is made using the third generation anti-CD19 CAR cassette described in WO 2012/079000, which is hereby incorporated-by-reference in its entirety for all purposes), and the 3'-UTR of the gene encoding IL-2 (NCBI Reference Sequence Number: NM 000586.3), which is hereby incorporated by reference in its entirety for all purposes). A nucleic acid encoding the IL-2 3'-UTR is engineered into the anti-CD19 CAR cassette in an appropriate expression vector. The IL-2, 3'-UTR sequence used was:

(SEQ ID NO: 21)
taattaagtgcttcccacttaaaacatatcaggccttctATTTATTTAaa tATTTAaattttatATTTAttgttgaatgtatggtttgctacctattgta actattattcttaatcttaaaactataaatatggatcttttatgattctt tttgtaagccctaggggctctaaaatggtttcacttATTTAtcccaaaat ATTTAttattatgttgaatgttaaatatagtatctatgtagattggttag taaaactATTTAataaatttgataaatataaa The anti-CD19 RDE CAR and anti-CD19 CAR constructs are transfected by routine methods into different populations of T-cells (primary human T-cells), and stable populations of T-cells are selected using appropriate antibiotics (or other selection schemes). T-cell populations with anti-CD19 RDE CARs (CD19$^-$/CD22$^-$/CD3$^+$) and T-cell populations with anti-CD19 CARs (CD19$^-$/CD22$^-$/CD3$^+$) are activated by co-incubation with anti-CD3/CD28 beads and allowed to return to quiescent state after debeading.

Quiescent anti-CD19 RDE CAR T-cells are co-cultured with CD19$^+$/CD22$^+$/CD3$^-$ Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The RDE-CAR T-cells and the Raji cells are grown together for 24 hours. Cultures are washed, and then stained with anti-CD22 and anti-CD3 reagents, followed by counting of CD22$^+$ (Raji target cells) and CD3$^+$ cells (Smart CAR T-cells). These measurements will identify the target cell killing rate (e.g., half-life) and the proliferation rate of the RDE-CAR T-cells at different levels of RDE-CAR expression.

Activated anti-CD19 RDE CAR T-cells are co-cultured with CD19$^+$/CD22$^+$/CD3$^-$ Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2, mM, 3 mM, 4 mM, 5 mM, 7.5 mM and 10 mM). The RDE-CAR T-cells and the Raji cells are grown together for 24 hours. Samples from culture media are taken and tested for IL-2 by ELISA.

As a control activated anti-CD19 CAR T-cells are co-cultured with CD19$^+$/CD22$^+$/CD3$^-$ Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 24 hours. Cultures are washed, and then stained with anti-CD22 and anti-CD3 reagents, followed by counting of CD22$^+$ (Raji target cells) and CD3$^+$ cells (CAR T-cells).

As a control, activated anti-CD19 CAR T-cells are co-cultured with CD19$^+$/CD22$^+$/CD3$^-$ Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 48 hours. Samples from culture media are taken and tested for IL-2 by ELISA.

Example 2: Removal of MicroRNA Binding Sites from an RDE

The AU-rich element from the 3'-UTR of IL-2 has mir-181 and mir 186 microRNA binding sites. Different combinations of the microRNA sites were removed from the 3'-UTR of IL-2. When the MIR186 micro-RNA sites were removed from the 3'-UTR of IL-2 the dynamic range of expression from constructs with this UTR increased 50 fold. The modified IL-2, 3'-UTR replaces CTT in the sequence with GAA and is shown below (the new GAA is underlined in the sequence):

(SEQ ID NO: 22)
taattaagtgcttcccacttaaaacatatcaggccttctATTTATTTAaa tATTTAaattttatATTTAttgttgaatgtatggtttgctacctattgta actattattcttaatcttaaaactataaatatggatcttttatgatt<u>GAA</u> tttgtaagccctaggggctctaaaatggtttcacttATTTAtcccaaaat

ATTTAttattatgttgaatgttaaatatagtatctatgtagattggttag taaaactATTTAataaatttgataaatataaa The AU-rich element from the 3'UTR of IFNg also has micro-RNA binding sites characterized as mir-125. The sequence of the IFNg RDE is:

(SEQ ID NO: 23)
tggttgtcctgcctgcaatatttgaattttaaatctaaatctATTTAtta atATTTAacattATTTAtatggggaatatattttagactcatcaatcaa ataagtATTTAtaatagcaacttttgtgtaatgaaaatgaatatctatta atatatgtattATTTAtaattcctatatcctgtgactgtctcacttaatc ctttgttttctgactaattaggcaaggctatgtgattacaaggctttatc tcaggggccaactaggcagccaacctaagcaagatcccatgggttgtgtg tttatttcacttgatgataccaatgaacacttataagtgaagtgatactat

```
ccagttactgccggtttgaaaatatgcctgcaatctgagccagtgcttta atggcatgtcagacagaacttgaatgtgtcaggtgaccctgatgaaaaca tagcatctcaggagatttcatgcctggtgcttccaaatattgttgacaac tgtgactgtacccaaatggaaagtaactcatttgttaaaattatcaatat ctaatatatgaataaagtgtaagttcacaacta
```

Different combinations of the micro-RNA sites were removed from the 3'UTR of IFNg and tested for increased expression. When the mir125 micro-RNA sites were removed from the 3'-UTR of IFN-γ the expression rate from constructs with this UTR is increased.

Expression of GFP in T-cells, transfected with the RDE-GFP plus the microRNA sites, is compared to expression of GFP in T-cells with the RDE-GFP in which the microRNA sites have been removed, following activation with CD3/CD28 beads for 24 hours. The removal of the microRNA sites increased expression of the GFP by a factor of between 2-5 after 24 hours, relative to the cells with microRNA sites.

Example 3: Payload Delivery to DLBCL Using an Anti-CD19 CAR T-Cell

The anti-CD19 Smart CAR T-lymphocytes and anti-CD19 CAR T-cell lymphocytes of Example 6 are used in this example. These CAR T-lymphocytes are further engineered to include a construct encoding a PD-1 inhibitor under the control of the 3'-UTR of IL2 that has been modified by removal of the MIR186 sites. PD-1 inhibitors expressed by the construct include, for example, Pembrolizumab (Keytruda®), Nivolumab (Opdivo®), Cemiplimab (Libtayo®), Atezolizumab (Tecentriq®), Avelumab (Bavencio®), Durvalumab (Imfinzi®), BMS-936558, Lambrolizumab, or polypeptides derived from these drugs. Other PD-1 inhibitors that may be expressed by the construct include those disclosed in Herbst et al., J Clin Oncol., 31:3000 (2013); Heery et al., J Clin Oncol., 32:5s, 3064 (2014); Powles et al., J Clin Oncol, 32:5s, 5011(2014); Segal et al., J Clin Oncol., 32:5s, 3002 (2014), or U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and 8,217,149.

T-cell populations with anti-CD19 Smart CARs/PD-1 (CD19-/CD22-/CD3+) and T-cell populations with anti-CD19 CARs/PD-1 (CD19-/CD22-/CD3+) are activated by co-incubation with anti-CD3/CD28 beads. T-cells with anti-CD19 Smart CARs/PD-1 inhibitor or anti-CD19 CARs/PD-1 inhibitor were incubated with theophylline at 0, 75 and 250 μM for 72 hours. Activated anti-CD19 Smart CAR/PD-1 T-cells or anti-CD19 CAR/PD-1 T-cells were co-cultured with CD19+/CD22+/CD3-Raji target cells at Smart CAR/PD-1 T-cell:Raji target ratios of 2:1, 5:1, and 10:1. Ligand for the RNA control device, theophylline is maintained in the culture medium at concentrations of 0 μM, 75 μM, and 250 μM. The Smart-CAR/PD-1 T-cells or CAR/PD-1 T-cells and the Raji cells are grown together for 18 hours. Cultures are washed, and then stained with anti-CD22 and anti-CD3 reagents, followed by counting of CD22+(Raji target cells) and CD3+ cells (Smart CAR T-cells). Samples from culture media are also taken at 6, 12 and 18 hours, and tested for PD-1 inhibitor by ELISA.

Example 4: Payload Delivery to AML Using an Anti-CD133 CAR T-Cell

A CAR is made using the anti-CD20 CAR cassette described in Budde 2013 (Budde et al. PLoS1, 2013 doi: 10.1371/journal.pone.0082742, which is hereby incorporated-by-reference in its entirety for all purposes), with the anti-CD133 mAb 293C3-SDIE is used for the extracellular element (Rothfelder et al., 2015, ash.confex.com/ash/2015/webprogram/Paper81121.html, which is incorporated by reference in its entirety for all purposes) replacing the anti-CD20 extracellular domain. The anti-CD133 CAR also can encode the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the anti-CD20 CAR cassette is engineered to replace the anti-CD20 extracellular domain with the anti-CD133 element, and optionally the RNA control device is also engineered into the cassette. The anti-CD133 CAR with or without the RNA control device are cloned into appropriate expression vectors.

These anti-CD133 CAR and anti-CD133 Smart CAR constructs are transfected by routine methods into T-lymphocytes (Jurkat cells and/or primary human T-lymphocytes), and stable populations of T-lymphocytes are selected using appropriate antibiotics (or other selection schemes).

These CAR T-lymphocytes are further engineered to include a construct encoding a PD-1 inhibitor under the control of the RDE from the 3'-UTR of IL2 that has been modified by removal of a MIR186 site. PD-1 inhibitors expressed by the construct include, for example, Pembrolizumab (Keytruda®), Nivolumab (Opdivo®), Cemiplimab (Libtayo®), Atezolizumab (Tecentriq®), Avelumab (Bavencio®), Durvalumab (Imfinzi®), BMS-936558, Lambrolizumab, or polypeptides derived from these drugs. Other PD-1 inhibitors that may be expressed by the construct include those disclosed in Herbst et al., J Clin Oncol., 31:3000 (2013); Heery et al., J Clin Oncol., 32:5s, 3064 (2014); Powles et al., J Clin Oncol, 32:5s, 5011(2014); Segal et al., J Clin Oncol., 32:5s, 3002 (2014), or U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and 8,217,149.

T-lymphocyte populations with anti-CD133 CAR/PD-1 inhibitor or anti-CD133 Smart CAR/PD-1 inhibitor (CD20−/CD22−/CD3+) are activated by co-incubation with anti-CD3/CD28 beads.

Activated anti-CD133 CAR/PD-1 inhibitor or anti-CD133 Smart CAR/PD-1 inhibitor T-lymphocytes are co-cultured with CD133+/CD3− AML target cells (e.g., U937, MV4-11, MOLM-14, HL-60 and/or KG1a) at anti-CD133 CAR and/or anti-CD133 Smart CAR T-lymphocyte:AML target ratios of 2:1, 5:1, and 10:1. Ligand for the RNA control device, theophylline, is added to the culture medium at concentrations in the range of 500 μM to 1 mM (lower or greater concentrations can be used to titrate Smart-CAR activity to the desired level). The anti-CD133 CAR/PD-1 inhibitor and/or anti-CD133 Smart CAR/PD-1 inhibitor T-lymphocytes and the AML cells are grown together for 48 hours. Cultures are washed, and then stained with anti-CD133 and anti-CD3 reagents, followed by counting of CD133+ (AML target cells) and CD3+ cells (anti-CD133 CAR, anti-CD133 DE-CAR, anti-CD133 Smart CAR, and/or the anti-CD133 DE-Smart CAR T-lymphocytes). These measurements will identify the target cell killing rate (e.g., half-life) and the proliferation rate of the anti-CD133 CAR/

PD-1 inhibitor and/or anti-CD133 Smart CAR/PD-1 inhibitor T-lymphocytes at different levels of CAR expression. Samples from culture media are also taken at 12, 24, 26 and 48 hours, and tested for PD-1 inhibitor by ELISA.

Example 5: An RDE Construct for Expressing a Second Transgene

Constructs were made using an anti-CD19 CAR cassette as described in WO 2012/079000, which is hereby incorporated-by-reference in its entirety for all purposes), and a GFP-RDE1 (3'-UTR from IFNg) insert. These two inserts/cassettes were placed in the same lenti virus construct. The anti-CD19 CAR cassette and the insert with the GFP-RDE are transcribed in opposite directions, and the control regions for each are located in between the two insert/cassettes. The control region for the GFP-RDE insert was MinP and the RDE was the endogenous 3'-UTR of IFNg. The control region of the anti-CD19 CAR cassette was MND (as described above). CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed an increase in fluorescence when cultured with Raji target cells (activate CAR) of 1.0% to 6.5% (about 6.5 fold), and increase in fluorescence when cultured with CD3/CD28 beads (activate TCR) of 1.0% to 4.4% (about 4.4 fold). The transformed T-cells showed a change in activated cells in the population when cultured with Raji cells of 0.9% to 84.8%, and when cultured with CD3/CD28 beads of 0.9% to 90.8%.

Example 6: A Modified RDE2 Construct for Expressing a Second Transgene

Constructs were made using an anti-CD19 CAR cassette as described in Examples 11 and 12, and a GFP-RDE2.1 (IL-2 RDE) insert. The RDE2.1 was modified to remove the MIR186 microRNA sites, altering nucleotides from the 3'-UTR of IL-2 which was used as RDE2.

These two inserts/cassettes were placed in the same lenti virus construct. The anti-CD19 CAR cassette and the insert with the GFP-RDE are transcribed in opposite directions, and the control regions for each are located in between the two insert/cassettes. The control region for the GFP-RDE insert was a MinP. The control region of the anti-CD19 CAR cassette in was MND (as described above). CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed a change in activated cells in the population when cultured with Raji cells of 3.9% to 12.1%, and when cultured with CD3/CD28 beads of 3.9% to 11.1%.

Example 7: An RDE Construct for Expressing a Luciferase Transgene

Constructs were made using an anti-CD19 CAR cassette as described in WO 2012/079000, which is hereby incorporated-by-reference in its entirety for all purposes), and a Luciferase-RDE1 (3'-UTR of IFNg, Gold1) insert or a Luciferase-3'-UTR (a 3'-UTR that does not confer differential transgene translation in response to metabolic state of the cell, 3'-UTR). The anti-CD19 CAR cassette and the insert with the luciferase-RDE1 are transcribed in opposite directions, and the control regions for each are located in between the two insert/cassettes. The control region for the Luciferase-RDE1 insert and Luciferase-3'-UTR were either a MinP promoter or an NFAT promoter having the sequences of:

(MinP)
SEQ ID NO: 24
TAGAGGGTATATAATGGAAGCTCGACTTCCAG (NFAT)
SEQ ID NO: 25
GGAGGAAAAACTGTTTCATACAGAAGGCGTGGAGGAAAAACTGTTTCATA

CAGAAGGCGTGGAGGAAAAACTGTTTCATACAGAAGGCGTAGATCTAGAC

TCTAGAGGGTATATAATGGAAGCTCGAATTC

The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and luciferase expression in the T cells.

Figure 2:
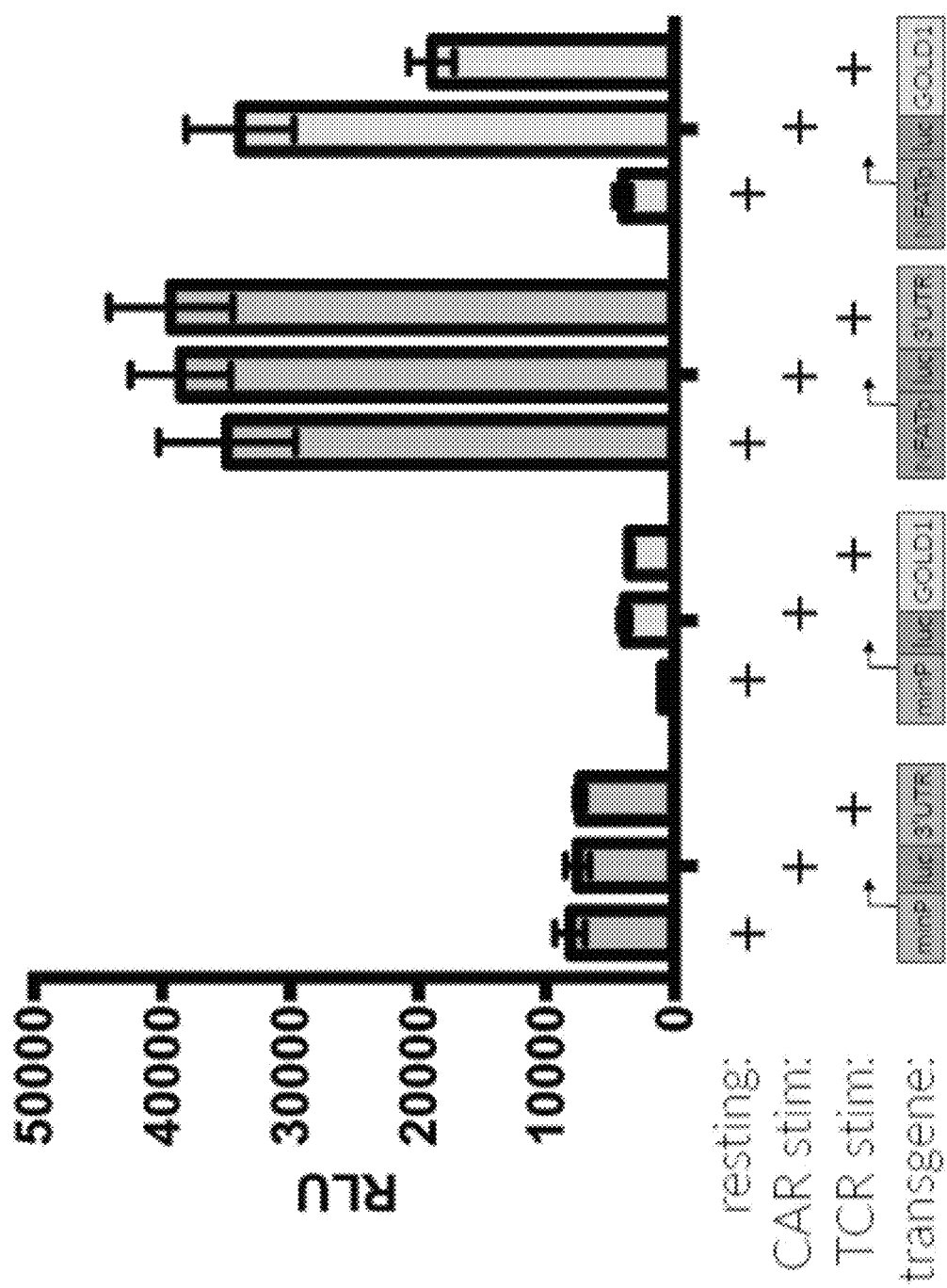

FIG. 2 shows that the transduced T-cells had an increase in bioluminescence when cultured with Raji target cells (activate CAR) or when cultured with CD3/CD28 beads (activate TCR) as compared to bioluminescence of T-cells at resting. The T-cells with a NFAT promoter and the 3'-UTR of IFNg (Gold1) showed a larger on-off response from CAR stimulation versus TCR stimulation. Under all conditions, T-cells with Gold1 had lower amounts of bioluminescence than T-cells under the same conditions (and same promoter) with Luciferase that was not controlled by the 3'UTR of IFNg (3'-UTR).

Example 8: Comparison of RDEs Controlling Luciferase

Constructs were made using an anti-CD19 CAR cassette as described in WO 2012/079000, which is hereby incorporated-by-reference in its entirety for all purposes), and a Luciferase-RDE1 (3' UTR of IFNg, Gold1) insert, a Luciferase-RDE2 (3'-UTR of IL-2, Gold2) insert, a Luciferase-RDE3 (3'-UTR of IL-2 modified as described above to remove the mir186 sites, Gold3), or a Luciferase-3'-UTR (a 3'-UTR that does not confer differential transgene translation in response to metabolic state of the cell, 3'-UTR). Combinations of these inserts/cassettes shown in FIG. 3 were placed in the similar lenti virus constructs. The anti-CD19 CAR cassette and the insert with the luciferase-RDE are transcribed in opposite directions, and the control regions for each are located in between the two insert/cassettes. The control region for the Luciferase-RDE insert and Luciferase-3'-UTR were either a MinP promoter or an NFAT promoter. The control region of the anti-CD19 CAR cassette was the MND promoter, and CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set CD19+ Raji B cells were incubated with the transduced T cells for 24 h. At 24 h, the T cells were stained for CD25 and CD69, which are activation markers, and subject to flow cytometry to measure these markers and luciferase expression in the T cells.

Figure 3:
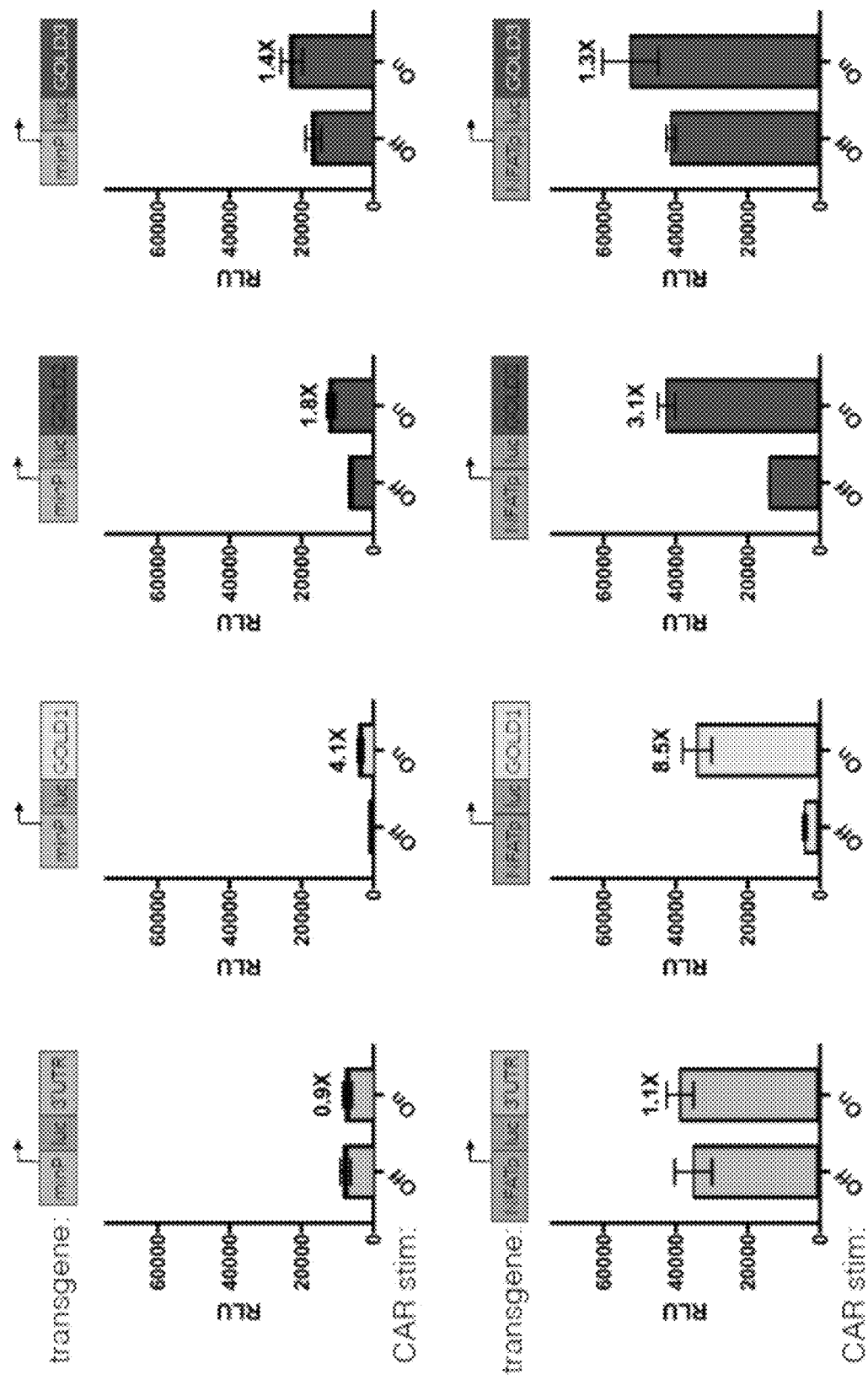

FIG. 3 shows that the transduced T-cells had an increase in bioluminescence when cultured with Raji target cells (activate CAR) as compared to bioluminescence of T-cells at resting for constructs with RDE1 (Gold1), RDE2 (Gold2), or RDE3 (Gold3). The T-cells with a NFAT promoter and the RDE1 showed a larger on-off response than T-cells with a MinP promoter and the corresponding RDE. Under all conditions, T-cells with an RDE controlling luciferase had lower amounts of bioluminescence than T-cells with luciferase cassettes that were not controlled by an RDE. Combined with the MinP promoter, RDE1 gave a 4.1-fold increase in bioluminescence with CAR stimulation, RDE2 gave a 1.8-fold increase in bioluminescence, and RDE3 gave a 1.4-fold increase. Combined with the NFAT promoter, RDE1 gave a 8.5-fold increase in bioluminescence with CAR stimulation, RDE2 gave a 3.1-fold increase in bioluminescence, and RDE3 gave a 1.3-fold increase. With either promoter, the RDE3 construct gave the highest amount of bioluminescence, the RDE1 construct gave the lowest amount of bioluminescence, and the RDE2 construct gave an amount of bioluminescence between RDE3 and RDE1.

Example 9: An RDE Construct for Expressing IL-12

Constructs were made using an anti-CD19 CAR cassette as described in WO 2012/079000, which is hereby incorporated-by-reference in its entirety for all purposes), and an IL-12-RDE1 (3'-UTR of IFNg) insert or an IL-12 3'-UTR (a 3'-UTR that does not confer differential transgene translation in response to metabolic state of the cell). The anti-CD19 CAR cassette and the insert with the IL-12-RDE1 are transcribed in opposite directions, and the control regions for each are located in between the two insert/cassettes. The control region for the IL-12-RDE1 insert and IL-12 3'-UTR were either a minP promoter or an NFAT promoter. The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set, CD19+ Raji B cells were incubated with the transduced T cells for 24 h. At 24 h, the T cells were stained for CD25 and CD69, which are activation markers, and subject to flow cytometry to measure these markers. IL-12 expression in the T cells was measured by ELISA.

Figure 4:
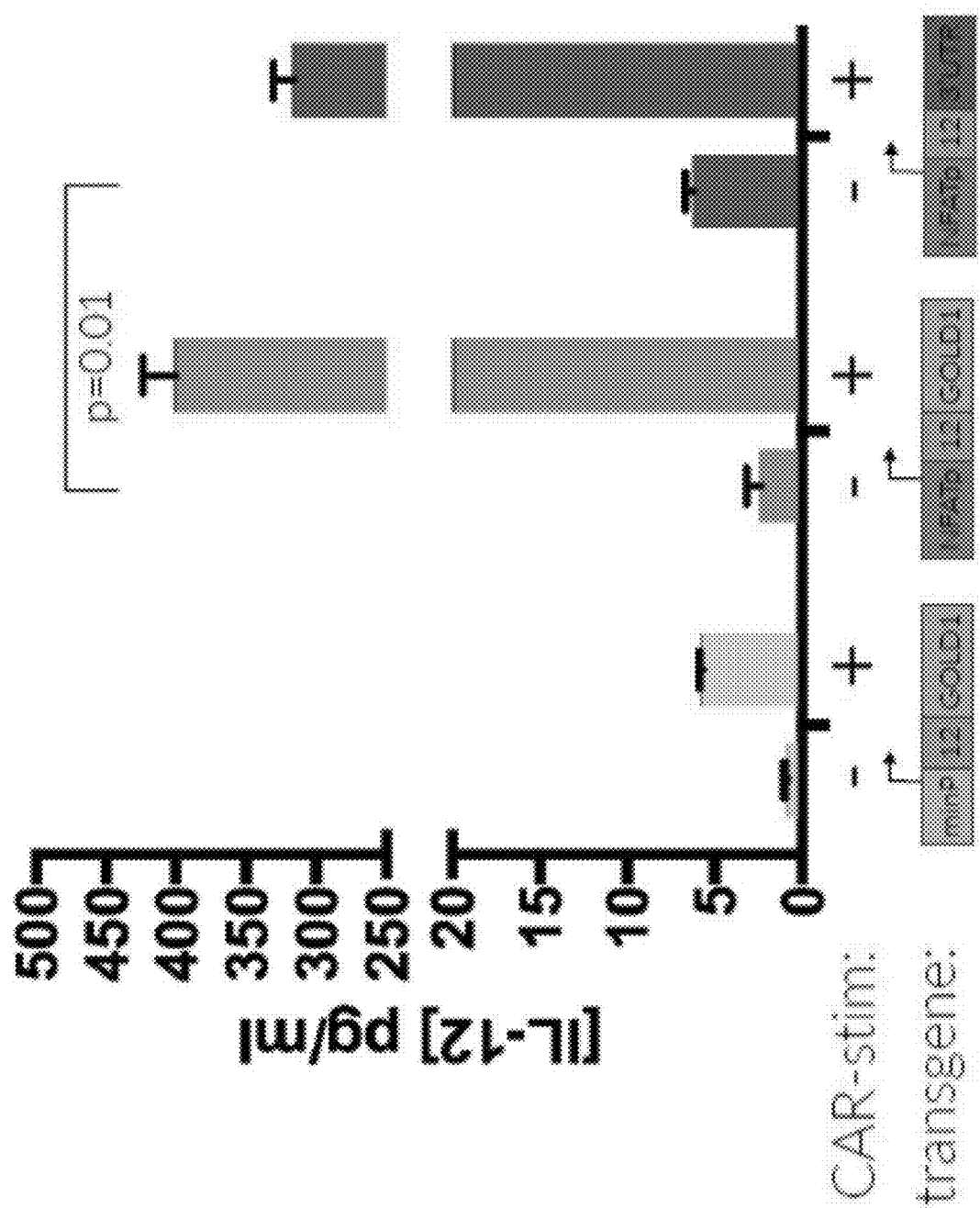

FIG. 4 shows that the transduced T-cells had an increase in IL-12 expression when cultured with Raji target cells (activate CAR) as compared to IL-12 expression of T-cells at resting using constructs controlled by the MinP promoter or NFAT promoter. T-cells with the NFAT promoter and RDE1 (Gold1) showed a 168-fold change in IL-12 expression form resting to CAR stimulation. T-cells with the NFAT promoter and a 3'-UTR (not responsive to CAR stimulation, 3'-UTR) showed a 50-fold change in expression, and a minP promoter with RDE1 (Gold1) showed a 6.3 fold change in expression.

Example 10: AU Elements and Steady State Expression

Figure 5:
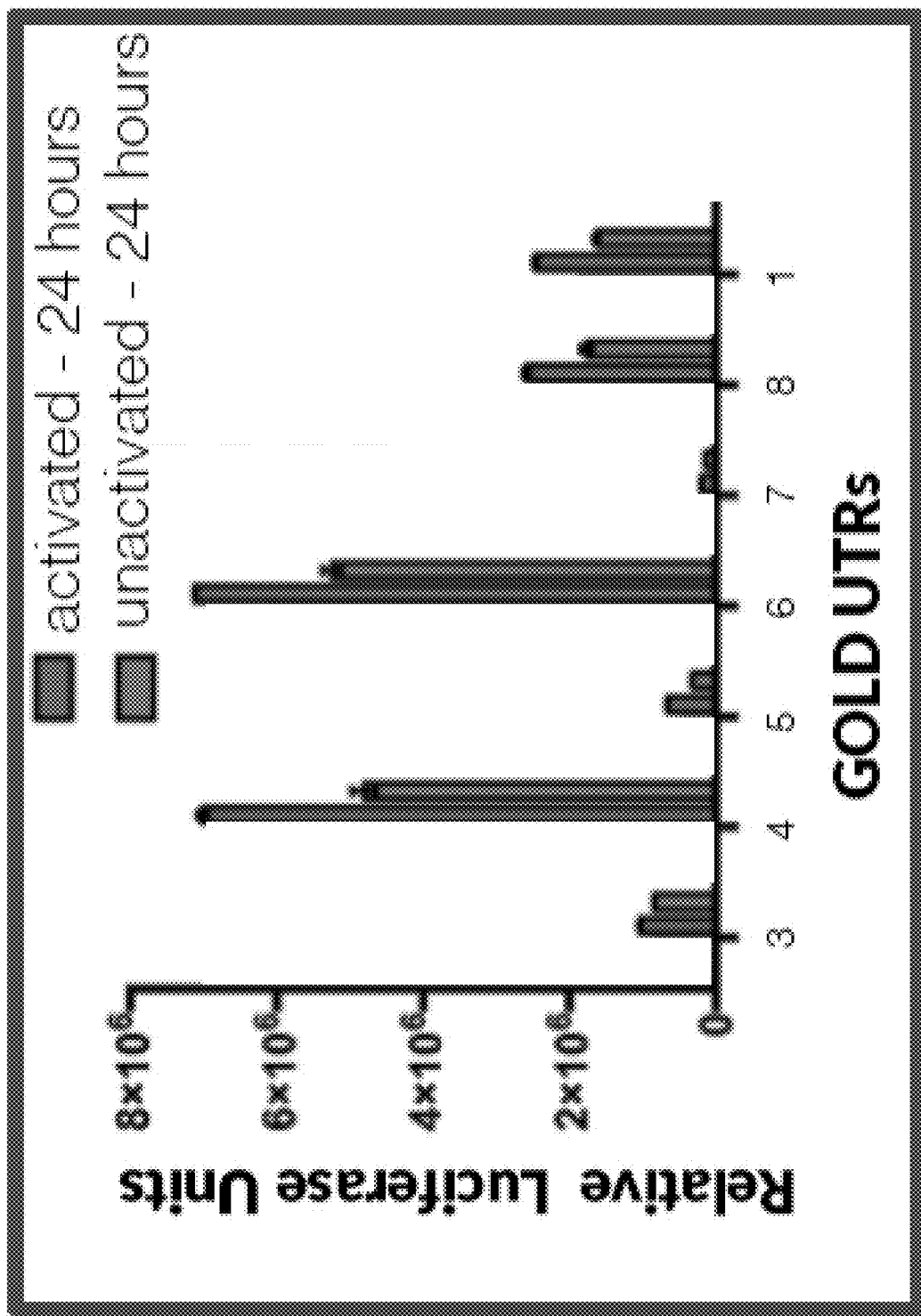

Constructs were made with different RDEs operably linked to a nucleic acid encoding luciferase. The different RDEs used were AU 4 (CTLA4), AU 13 (IL-5), AU 14 (IL-6), AU 15 (IL-9), AU 16 (IL-10), AU 17 (IL-13), and AU 101 (IFNg). These luciferase-AU constructs were transduced into primary T-cells. After the cells returned to the resting stage they were plated and sham induced (basal) or induced with anti-CD3 and anti-CD28 antibody (activated). At 24 hours post activation the amount of luciferase units in each was measured. These amounts are plotted in the bar graph of FIG. 5.

The AU elements in this example had different basal expression levels, different induced expression levels (at 24 hours), and different levels of fold induction. The AU constructs showed different amounts of basal expression, different amounts of induced expression and different amounts of fold induction (or dynamic range).

Example 11: AU Elements and Expression Parameters

Constructs were made with different RDEs operably linked to a nucleic acid encoding luciferase. The different RDEs used were AU 2 (CSF2), AU 3 (CD247), AU 5 (EDN1), AU 7 (SLC2A1), AU 10 (Myc), AU 19 (TMEM-219), AU 20 (TMEM-219snp), AU 21 (CCR7), AU 22 (SEM-A4D), AU 23 (CDC142-SE2), and AU 101 (IFNg). These luciferase-AU constructs were transduced into primary T-cells. After the cells returned to the resting stage they were plated and either not treated (basal) or activated with anti-CD3 and anti-CD28 antibody (activated). At 24 hours post activation the amount of luciferase units in each was measured. These amounts are plotted in the bar graph of FIG. 6. Alternatively, after the cells returned to resting stage they were plated into 96-well plates in quadruplicate for measuring at each time point: 1 day, 3 days, 6 days and 8 days. The cells were either not treated or activated with anti-CD3 and anti-CD28 antibody, and luciferase activity was measured at 1 day, 3 days, 6 days and 8 days. These results are plotted in the bar graph of FIG. 7, and shown in Table 1 below. FIG. 8 shows selected data plotted in a bar graph. The numbers in parentheses in Table 1 below are the Luciferase Units on Days 3, 6, and 8 divided by the Luciferase Units of Day 1.

TABLE 1

| | Luciferase Units | | | |
|---|---|---|---|---|
| AU Construct | Day 1 | Day 3 | Day 6 | Day 8 |
| AU 2 (CSF2) | 60051 | 306035 (5) | 578305 (10) | 591953 (10) |
| AU 101 (IFNg) | 85816 | 473395 (6) | 724129 (8) | 817447 (10) |
| AU 5 (EDN1) | 69391 | 613921 (9) | 838040 (12) | 1023000 (15) |
| AU 3 (CD247) | 44939 | 595753 (13) | 961839 (21) | 1116000 (25) |
| AU 20 (TMEM-219snp) | 1135000 | 10750000 (9) | 21020000 (19) | 25480000 (22) |
| AU 10 (Myc) | 1233000 | 16020000 (13) | 26780000 (22) | 27800000 (23) |
| AU 7 (SLC2A1) | 4914 | 80906 (16) | 132974 (27) | 136537 (28) |
| AU 21 (CCR7) | 27128 | 465140 (17) | 604016 (22) | 692715 (26) |
| AU 23 (CDC42-SE2) | 71105 | 1215000 (17) | 2012000 (28) | 2110000 (30) |
| AU 22 (SEM-A4D) | 226815 | 2829000 (12) | 6106000 (27) | 7396000 (33) |
| AU 19 (TMEM-219) | 833146 | 11260000 (14) | 22560000 (27) | 27500000 (33) |

Figure 6:
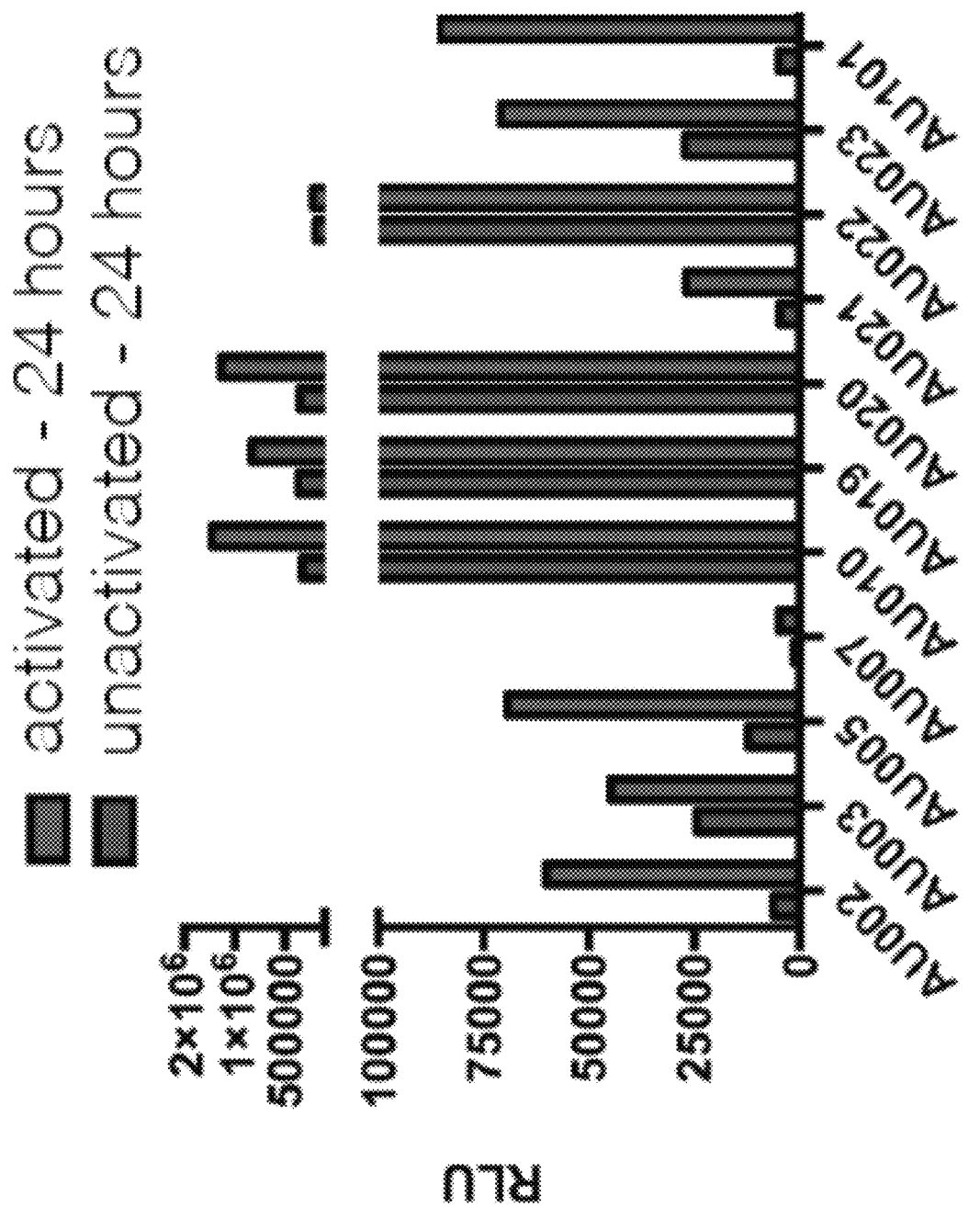
FIG. 6 shows basal luciferase expression and activated luciferase expression for luciferase constructs utilizing different RDEs as control elements in primary T-cells.
Figure 7:
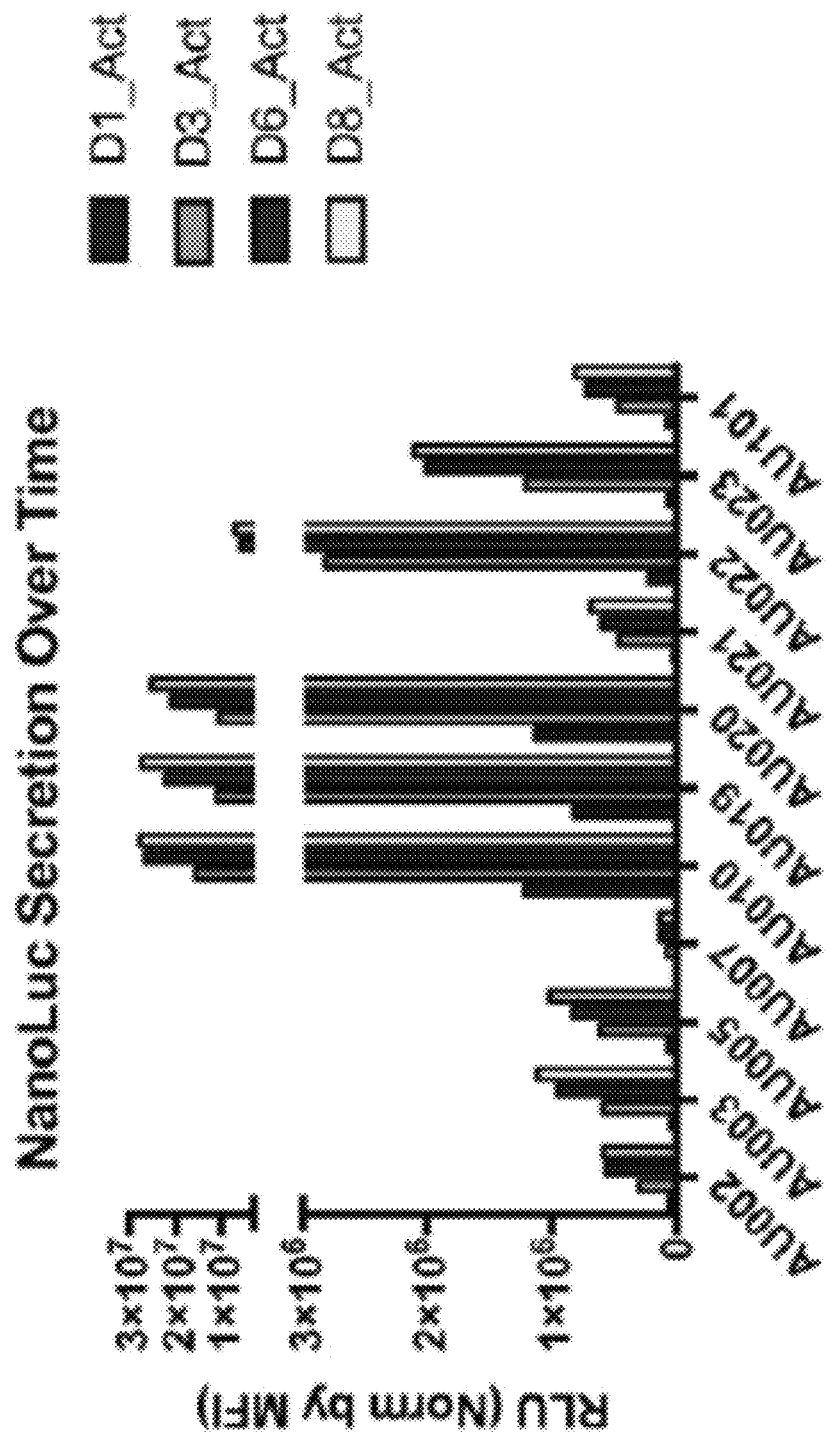
FIG. 7 shows activated luciferase/basal luciferase expression after 1, 3, 6, and 8 days for luciferase constructs utilizing different RDEs as control elements.
Figure 8:
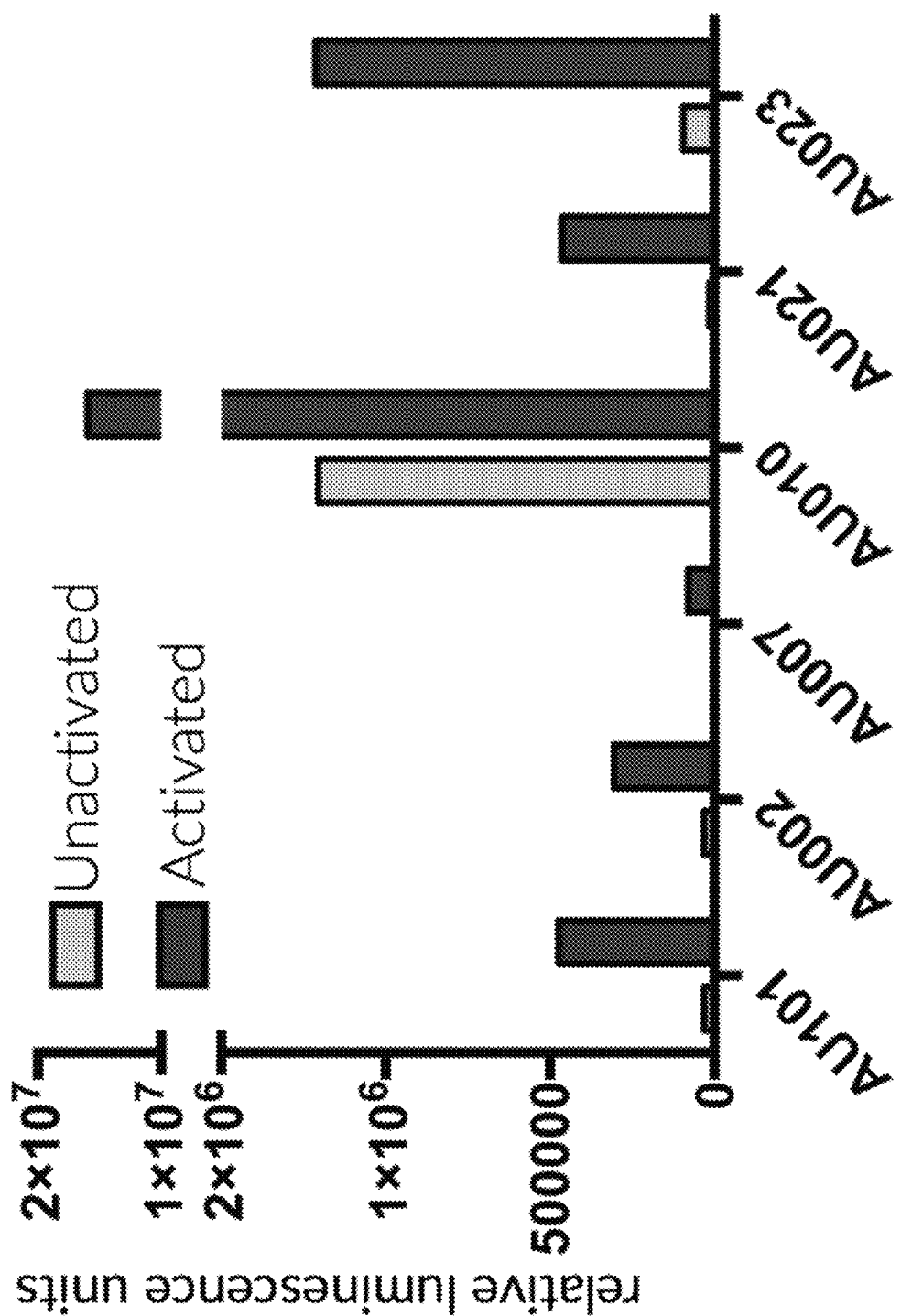
FIG. 8 shows basal luciferase expression and activated luciferase expression for luciferase constructs utilizing different RDEs as control elements.

The AU elements in FIG. 6, FIG. 7 and Table 1 had different basal expression levels, different induced expression levels (at 24 hours), and different levels of fold induction. The basal expression levels differed over an about 2000 fold range for these AU elements (AU 7 to AU 20), and the induced expression levels differed over an about 5500 fold range (AU 7 to AU 10). Basal expression for the constructs ranged from 1390 for AU 7 (SLC2A1) to 2,927,000 for AU 20 (TMEM-219snp). Activated expression ranged from 4914 for AU 7 (day 1) to 27,800,0000 for AU 10 (day 8). FIG. 8 and Table 1 show that some AU elements had lower levels of output, for example, AU 101 (IFNg), AU 2 (CSF2), AU 5 (EDN1), AU 7 (SLC2A1), AU 21 (CCR7), and AU 23 (CDCl42-SE2). Some AU elements had intermediate amounts of output: AU 19 (TMEM-219) and AU 22 (SEM-A4D). And some AU element had high output: AU 20 (TMEM-219snp) and AU 10 (Myc).

Figure 9:
FIG. 9 shows the dynamic range (activated luciferase/basal luciferase) measured 1, 3/4, 6, and 8 days after activation for luciferase constructs utilizing different RDEs as control elements.
Figure 10:
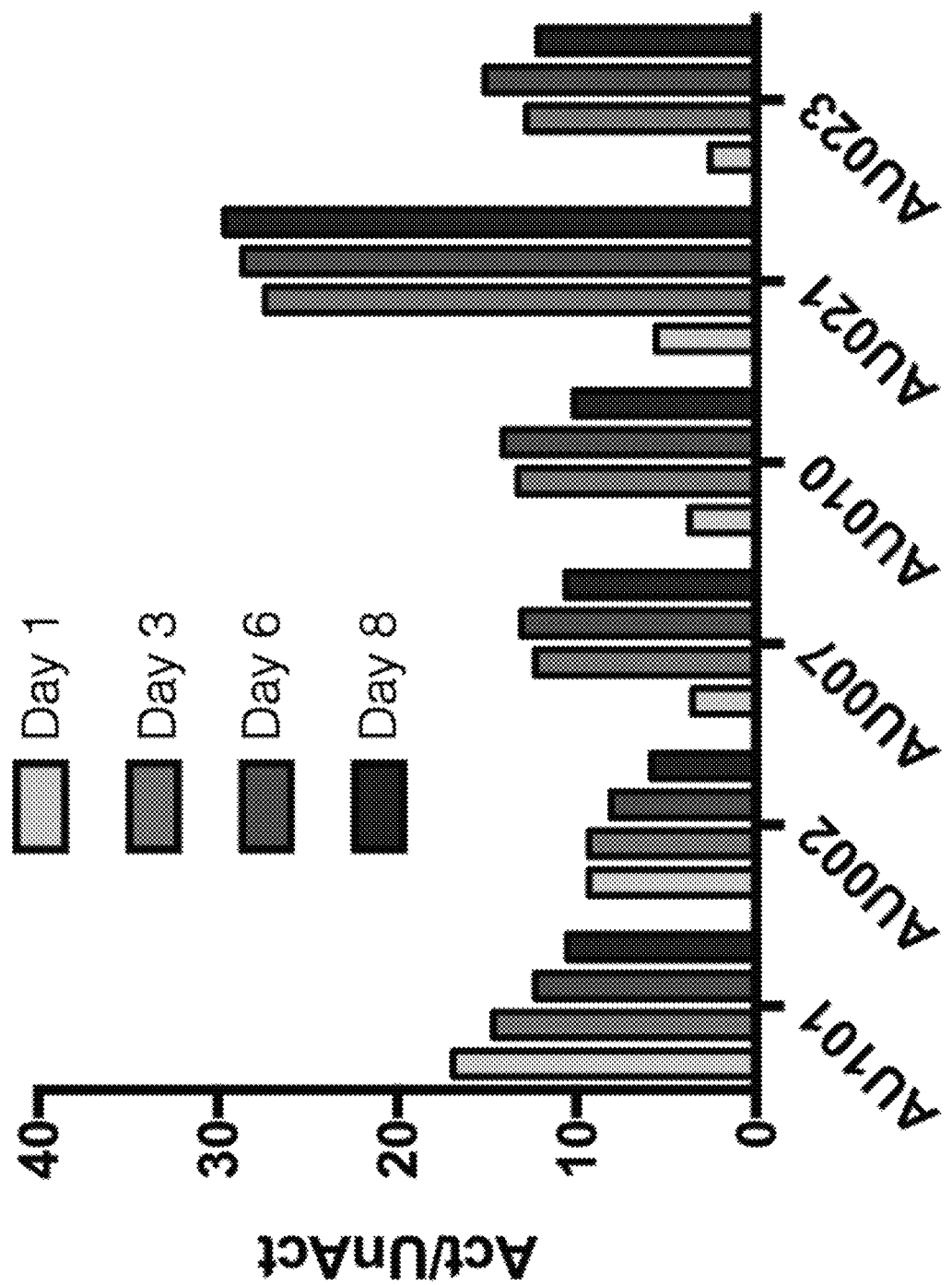
FIG. 10 shows the dynamic range (activated luciferase/basal luciferase) measured 1, 3/4, 6, and 8 days after activation for luciferase constructs utilizing different RDEs as control elements.

The Luciferase data was also analyzed for dynamic range (fold induction or luciferase activated/luciferase basal) of each luciferase-AU construct. The dynamic range (fold induction) for each AU construct at Days 1, 3/4 (activated expression was measured on Day 3 and basal expression was measured on Day 4), 6 and 8. This data is shown below in Table 2, and plotted in bar graphs in FIG. 9 and FIG. 10.

TABLE 2

| | Fold Induction | | | |
|---|---|---|---|---|
| AU Construct | Day 1 | Day 3/4* | Day 6 | Day 8 |
| AU 2 | 9.3 | 9.3 | 8.1 | 5.8 |
| AU 101 | 16.9 | 14.6 | 12.3 | 10.5 |
| AU 5 | 5.7 | 11.9 | 10.1 | 9.4 |
| AU 21 | 5.6 | 27.3 | 28.6 | 29.6 |
| AU 3 | 1.8 | 6.7 | 8.1 | 6.8 |
| AU 20 | 3.1 | 7.3 | 9.3 | 8.7 |
| AU 10 | 3.7 | 13.2 | 14.1 | 10.2 |
| AU 7 | 3.5 | 12.3 | 13.1 | 10.6 |
| AU 23 | 2.6 | 12.8 | 15.1 | 12.2 |
| AU 19 | 2.3 | 9.3 | 12.9 | 13.8 |
| AU 22 | 1.2 | 4.6 | 6.9 | 7.1 |

*Induction was measured on Day 3 and basal was measured on Day 4.

At Day 1 dynamic range (fold induction=activated/basal) ranged from about 1 (AU 22) to about 17 (AU 101). At Day 3/4, dynamic range varied from about 4.5 (AU 22) to about 27 (AU21). At Day 6, dynamic range varies from about 7 (AU 22) to about 29 (AU 21). On Day 8, dynamic range varied from about 7 (AU22) to about 30 (AU 21). The AU constructs showed a number of related patterns. AU 2 and AU 101 showed a rapid increase in dynamic range on Day 1, and then the dynamic range decreased on days 6 and 8.

AU 5 and AU 21 show increasing dynamic range from day 0 to day 3/4, and then the dynamic range is maintained through days 6 and 8. AU 3, AU 20, AU 10, AU 7 and AU 23 showed rising dynamic range from day 0 to day 6, and then the dynamic range decreased on day 8. AU 19, and AU 22, showed rising dynamic ranges from day 0 to day 8.

AU 21 and AU 23 showed accelerating dynamic range and these AU constructs also had low basal expression (day 1=4865 and 27363, respectively). AU 2 and AU 101 showed decreasing dynamic range from 24 hours to 72 hours and these AU elements also had low basal expression. AU 5 and AU 20 also showed decreasing dynamic range from day 1 to day 3/4 (though more expression than AU 2 and AU 101) and AU 5 had low basal expression whereas AU 20 had high basal expression. AU 10, AU 19 and AU 22 showed consistent dynamic range from day 1 to day 3/4 and had high basal levels of expression. AU 3 and AU 7 also had consistent dynamic range from day 1 to day 3/4 and had low basal expression levels.

The above data shows that different AU elements have different temporal effects on expression from days 1-8. Some AU elements show accelerating dynamic range over different portions of the time range. The AU elements show different amounts of total expression ($C_{max}$) and different times to maximum expression ($T_{max}$). The AU elements also show different maximum dynamic ranges and time to reach these maximums. These differing kinetics of expression can be used to provide customized basal, $C_{max}$, $T_{max}$, dynamic range, and time to max dynamic range for a desired transgene. These differing kinetics can also be used to provide temporally distinct expression for two transgenes in a cell after activation of the cell.

Example 12: AU Element Control with Glucose and Galactose

Figure 11:
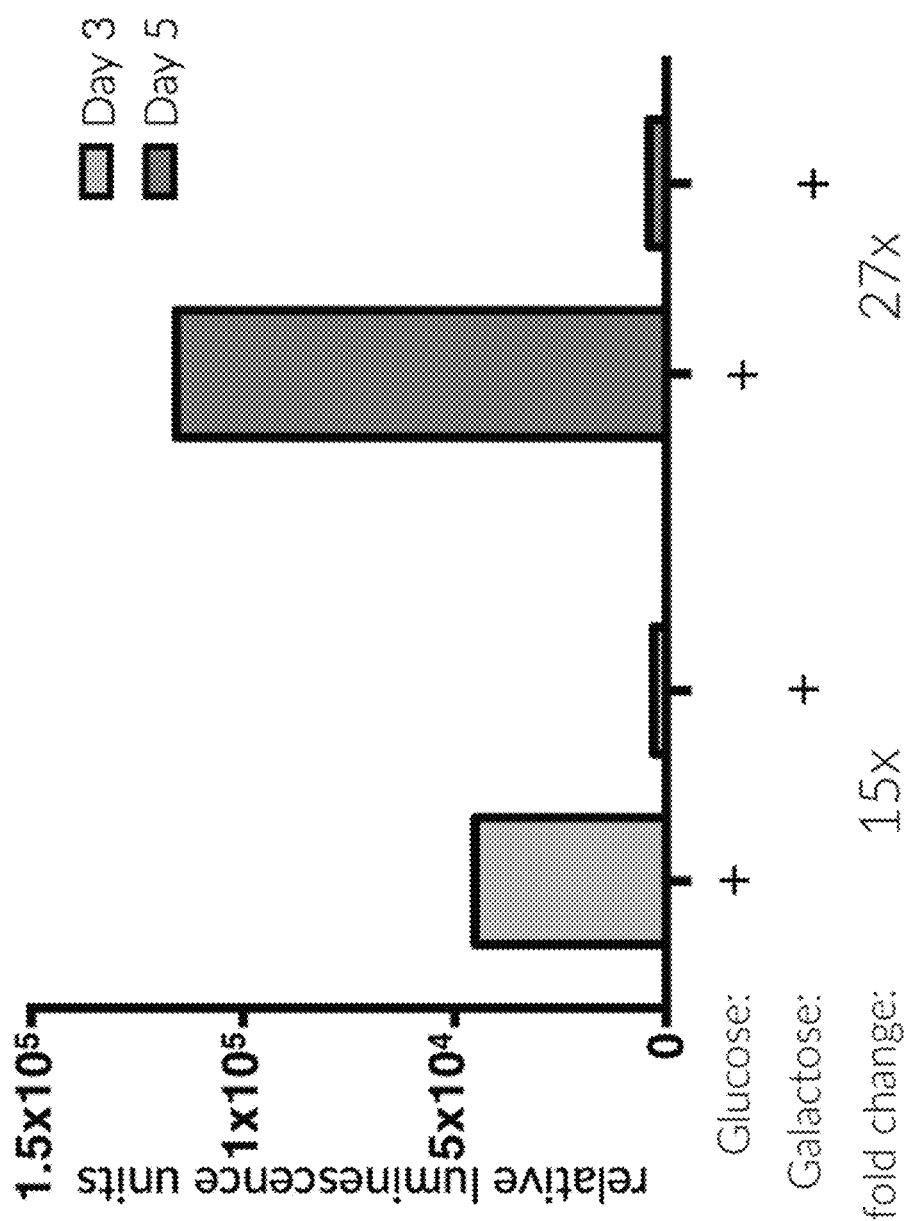
FIG. 11 shows the impact on luciferase expression for luciferase constructs utilizing an RDE as a control element in the presence of glucose and galactose.

Constructs were made with different RDEs operably linked to a nucleic acid encoding luciferase. The RDE was an AU element responsive to glycolytic state of the cell. The AU element—luciferase constructs were transduced into T-cells. After the cells reached the resting state, they were split into wells and fed media including either glucose or galactose. Luciferase activity was measured on days 3 and 5. These results are shown in the bar graph of FIG. 11. The results show that glucose increased expression of luciferase compared to galactose and the amount of expression increased from days 3 to 5. On day 3 the glucose treated cells had 15× more expression of luciferase than the galactose treated cells and on day 5 this had grown to 27× more expression.

Example 13: Delivery and Design of a Viral Payload

A Smart Car is made using the third generation anti-CD19 CAR cassette described in WO 2012/079000, which is hereby incorporated-by-reference in its entirety for all purposes), and the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the 3XL2bulge9 control device is engineered into the anti-CD19 CAR cassette in an appropriate expression vector. The anti-CD19 Smart CAR and anti-CD19 CAR constructs are transfected by routine methods into different populations of T-cells (Jurkat cells and/or primary human T-cells), and stable populations of T-cells are selected using appropriate antibiotics (or other selection schemes). T-cell populations with anti-CD19 Smart CARs (CD19$^-$/CD22$^-$/CD3$^+$) and T-cell populations with anti-CD19 CARs (CD19$^-$/CD22$^-$/CD3$^+$) are activated by co-incubation with anti-CD3/CD28 beads.

Third generation Lentiviral packaging, envelope, and transfer plasmids are obtained from addgene. The Rev encoding packaging plasmid is engineered to include the AU101 (INFg) RDE in the 3'-UTR of Rev. The modified Rev packaging plasmid, the Gag Pol packaging plasmid, and the envelope plasmid are transfected into anti-CD19 T-lymphocyte cells. A transfer plasmid is engineered to include GFP as the transgene in the transfer plasmid. This transfer plasmid is also transfected into the anti-CD19 CAR T-lymphocyte cells.

Anti-CD19 Smart CAR T-lymphocytes are co-cultured with CD19+/CD22+/CD3-Ramos target cells at Smart CAR T-lymphocyte:Raji target ratios of 2:1, 5:1, and 10:1. Ligand for the RNA control device, theophylline is added to the culture medium at concentrations in the range of 2 μM to 2 mM (2 μM, 10 μM, 20 μM, 100 μM, 200 μM, 1 mM, and 2 mM). The Smart-CAR T-cells and the Raji cells are grown together for 48 hours.

At the end of the incubation period, the culture media is separated from the T-lymphocytes and Raji cells. Viral titer in the supernatant is measured using an ELISA with anti-lentivirus antibody reagents. Infectivity and payload delivery by the viruses is tested by infecting HEK 293 cells with the virus, and after a suitable incubation time measuring GFP fluorescence from the transduced HEK 293 cells.

Example 14: Payload Delivery Using Gold in a Mouse Lymphoma Model

Constructs were made using an anti-CD19 CAR cassette as described in WO 2012/079000, which is hereby incorporated-by-reference in its entirety for all purposes, and a Luciferase-AU (3' UTR of IL-6) insert. These constructs were placed in a bicistronic *lenti* virus construct. The anti-CD19 CAR cassette and the insert with the luciferase-RDE are transcribed in opposite directions on the bicistronic vector, and the control regions for each are located in between the two insert/cassettes. The control region for the Luciferase-RDE insert was a MinP promoter. The control region of the anti-CD19 CAR cassette was the MND promoter. CD4+ T-cells were transduced with the bicistronic construct.

A second construct was made using the anti-CD19 CAR cassette described above and a Luciferase insert (without the RDE element so that expression was constitutive). Both constructs were separately transduced into different groups of T-cells.

The transduced T cells were allowed to return to resting state, and then were tested after stimulation as follows. For the 'no stimulation' set, transduced T-cells were incubated for 24 h alone in medium. For the 'Raji co-culture' set CD19+ Raji B cells were incubated with the transduced T cells for 24 h. At 24 h, the T cells were stained for CD25 and CD69, which are activation markers, and subject to flow cytometry to measure these markers and luciferase expression in the T cells. These in vitro results showed that the anti-CD19 CAR T-cells made luciferase after activation of the T-cells through the CAR.

These anti-CD19 CAR T-cells with the luciferase-RDE were also tested in a mouse model for lymphoma. CD19+ Raji cells were implanted in the flanks of NSG mice. After tumor formation, the anti-CD19 CAR T-cells were injected into the mice and the mice were scanned for luminescence. Imaging of the mice showed luminescence at the tumor sites from anti-CD19 CAR T-cells that have been activated by the CD19 positive tumor. The amount of luminescence increased over time as more T-cells were activated. In contrast, the anti-CD19 CAR T-cells with constitutive expression of luciferase should luminescence throughout the mice as well as at the site of the tumors in the flanks of the mice.

Example 15: Payload Delivery to αvβ6 Positive Solid Tumor

A nucleic acid encoding a knottin as described in Silverman et al., J. Mol. Biol. 385:1064-75 (2009) and Kimura et al, Proteins 77:359-69 (2009), which are incorporated by reference in their entirety for all purposes is operably linked to a nucleic acid encoding the CAR components aCD43z, CD8Hinge, CD8transmembrane, 41BB(CD28 or other costim), and CD3z to make a nucleic acid encoding an anti-αvβ6 CAR.

The nucleic acid encoding the anti-αvβ6 CAR is transfected by routine methods into T-cells (Jurkat cells and/or primary human T-cells), and stable populations of T-cells are selected using appropriate antibiotics (or other selection schemes). T-cell populations with anti-αvβ6 CARs are activated by co-incubation with anti-CD3/CD28 beads. These cells are also engineered with an expression cassette encoding IL-12 operably linked to the Gold element from INFg or AU 21 (CCR7) is placed under the control of the promoter Min P.

The anti-αvβ6 CAR T-cells are incubated in wells with αvβ6 tumor cells. After incubation, the wells are tested for secretion of IL-12 from the anti-αvβ6 CAR T-cells. anti-αvβ6 CAR T-cells secrete IL-12 when incubated with αvβ6 tumor cells, and the controls show low or no secretion when the CAR T-cell is not stimulated.

Example 16: An Anti-Onco CD 43 CAR for AML

A single chain antibody for onco-sialylated CD 43 was made using an anti-onco-sialylated CD 43 antibody. The nucleic acid encoding this single-chain antibody was combined with a nucleic acid encoding the CAR components aCD43z,CD8Hinge,CD8transmembrane,41BB(CD28 or other costim), and CD3z to make a nucleic acid encoding an anti-onco-sialylated CD 43 CAR.

The nucleic acid encoding the anti-onco-sialylated CD 43 CAR is transfected by routine methods into T-cells (Jurkat cells and/or primary human T-cells), and stable populations of T-cells are selected using appropriate antibiotics (or other selection schemes). T-cell populations with anti-onco-sialylated CD 43 CARs are activated by co-incubation with anti-CD3/CD28 beads.

Example 17: Payload Delivery to CD 43 Positive AML

An expression cassette encoding IL-12 operably linked to the Gold element from INFg or AU 21 (CCR7) is placed under the control of the promoter Min P, and engineered into the anti-onco-sialylated CD 43 CAR T-cell.

The anti-onco-sialylated CD 43 CAR T-cells are incubated in wells with AML cells. After incubation, the wells are tested for secretion of IL-12 from the anti-onco-sialylated CD 43 CAR T-cells. Anti-onco-sialylated CD 43 CAR T-cells secrete IL-12 when incubated with AML cells, and the controls show low or no secretion when the CAR T-cell is not stimulated.

Example 18: miRNA as a Payload

A payload transgene encoding IL-12 is engineered to have an artificial intron encoding a mir155 cassette as disclosed in Du et al., FEBs Journal 273:5421-5427 (2006) or Chung et al., Nucl Acids Res 34:e53 (2006). The mir155 cassette is engineered to include an AU element such as, for example, AU101 (IFNg) or AU14 (IL-6), operably linked to it, and the transgene is also engineered with an AU element such as AU101 or AU14. This transgene with the mir155 intron is engineered into primary T-cells. An anti-CD19 CAR as described in Example 14 is also engineered into the primary T-cells.

The anti-CD19 CAR T cells with the IL-12 payload are allowed to return to resting state, and then are tested after stimulation as follows. For the 'no stimulation' set, transduced T-cells are incubated for 24 h alone in medium. For the 'Raji co-culture' set CD19+ Raji B cells are incubated with the transduced T cells for 24 h. At 24 h, the T cells are stained for CD25 and CD69, which are activation markers, and subject to flow cytometry to measure these markers. The cells are also tested for expression of the payload IL-12.

These anti-CD19 CAR T-cells with the IL-12 payload are also tested in a mouse model for lymphoma. CD19+ Raji cells are implanted in the flanks of NSG mice. After tumor formation, the anti-CD19 CAR T-cells with the IL-12 payload are injected into the mice. At every third day starting at day 4 after administration, tumor killing in the mice is measured using calipers.

Example 19: IL-12 Payload Delivery

A construct with an anti-CD19 CAR as described in Example 14 was made. A construct with the NFAT promoter operably linked to a nucleic acid encoding IL-12 followed by AU101 (the RDE from INFg) was also made. The IL-12 transcript made from the construct operably links the coding sequence for IL-12 to the AU101 RDE. A second IL-12 construct was made that provided constitutive expression of IL-12. A third construct placed Luciferase under control of an AU14 (IL-6).

The constructs were transduced into primary T-cells which were then allowed to return to a resting state. This produced anti-CD19 CAR T-cells with payloads of IL-12 (RDE controlled or constitutive) or luciferase.

The primary T-cells with the anti-CD19 CAR and IL-12 payload (RDE controlled or constitutive) or luciferase payload were administered to mice bearing CD19+ tumors in their flanks. Killing of tumor cells was monitored over 42 days. The mice which received T-cells with the anti-CD19 CAR and luciferase payload showed a moderate amount of tumor cell killing (about 3 logs). The mice receiving the IL-12 payloads had a large amount of tumor cell killing (6-7 logs). A comparison of IL-12 serum levels in the mice receiving the constitutive or AU101 controlled IL-12 had 10-fold differences in the systemic IL-12 levels with the AU101 controlled payload having 10 times lower amounts of IL-12 than the constitutive IL-12 payload.

The RDE control of IL-12 expression lowered systemic IL-12 levels in the mice but gave localized concentrations of IL-12 that improved tumor cell killing. After the activated CAR T-cells kill the tumor cells these CAR T-cells can migrate from the tumor site to lymph nodes and/or the spleen where they can educate other T-cells and form memory T-cells.

Example 20: Payload Delivery to DLL3+ Cancer Cells

CAR constructs are made using an anti-DLL3 antibody domain such as described in US20170137533 (which is incorporated by reference in its entirety for all purposes) as SC16.15. This anti-DLL3 antibody domain is made into a single chain antibody (scFv), and the anti-DLL3 scFv is combined with the transmembrane and intracellular portions of a CAR (such as those described in WO 2012/079000, which is hereby incorporated-by-reference in its entirety for all purposes) to make an anti-DLL3 CAR.

Payload constructs are made by engineering a transgene with an RDE so that when the transgene is transcribed the transcript for the transgene operably links the transgene to the RDE. The payload transgene can encode an anti-4-1BB antibody, an anti-CD11b antibody, an anti-CTLA4 antibody, an anti-IL1b antibody, a BiTE, a CCL2, an anti-CXCR4 antibody, an anti-CXCL12 antibody, a HAC, a heparinase, a hyaluronidase, a Hsp60, a Hsp70, an IL-2, an IL-12, an IL-15, an IL-18, an INFγ, a miRNA (e.g., mir155), a CD40 ligand, an ApoE3, an ApoE4, an antagonists of CSF1 receptor, a TNFα, and/or an anti-CD28 antibody. The RDE can be AU101 (INFg) or AU14 (IL-6).

The constructs are transduced into primary T-cells which are then allowed to return to a resting state. This produced anti-DLL3 CAR T-cells with one or more of the payloads: anti-CXCL12 antibody, anti-CXCR4 antibody, IL-12, anti-4-1BB antibody, anti-CD11b antibody, anti-CTLA4 antibody, anti-IL1b antibody, a BiTE, CCL2, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies).

An NSG mouse model from Jackson Laboratories is used to establish cancer xenografts of human melanoma, human small cell lung cancer (SCLC), and human IDH1mut glioma. After the cancer xenograft is established in the mice, the mice are treated with the primary T-cells with the anti-DLL3 CAR and one of the payloads. Cancer xenograft killing is then compared between the different payloads of the DLL3-CAR T-cells.

Example 21: B Toxin Fusion Payload Delivery to Target Cell

CAR T-cells are made as described in Example 19, except that the IL-12 payload is replaced with a modified B Toxin fusion as described below.

The B Toxin fusion is made using tetanus toxin as described in Toivonen et al., Toxins 2:2622-44 (2010) and fusing the B domain of tetanus toxin to the payload encoding luciferase from *Gaussia princeps* (a secreted luciferase). This B Toxin payload is modified to provide for targeting to the CD19 antigen by replacing the tetanus B domain receptor binding portion with the anti-CD19 CAR portion which binds to CD19 (e.g., an anti-CD19 scFv). This can be done as described in Kelley et al., Proc. Natl Acad. Sci. 85:3980-84 (1988) for the B domain of diphtheria toxin.

The primary T-cells with the anti-CD19 CAR and modified B Toxin payload (RDE controlled or constitutive) are administered to mice bearing CD19+ tumors in their flanks. Killing of tumor cells and adverse responses are monitored in the treated mice. The mice treated with the CAR T-cells with RDE controlled, modified B Toxin payload show increased tumor cell killing.

Example 22: hnRNPLL Control of Payload Expression

A nucleic acid encoding GFP is engineered to have extra introns and an extra exon at the 3'end of the coding region. The nucleic acids encoding GFP are followed by intron 1 from betaglobin, exon 4 of CD45 (has hnRNPLL binding sites) and another intron of betaglobin (engineered to have hnRNPLL CA repeat binding sites). This engineered GFP encoding nucleic acid is operably linked to a constitutive promoter.

The expression cassette with the nucleic acid encoding this engineered GFP is transduced into primary T-cells which are then allowed to express the GFP in a quiescent state. This should produce a GFP protein with the amino acids of exon 4 of CD45 on carboxyl terminal end. This fusion polypeptide should have reduced GFP activity. The primary T-cells with the expression cassette for GFP are then activated with anti-CD3/CD28 beads. These activated cells should produce hnRNPLL which should lead to exclusion of exon 4 of CD45 from the GFP transcript which now encodes active GFP. Translation of this transcript produces active GFP that can be detected.

Example 23: Coordinated Delivery of CXCL9 and an Anti-PD1 Therapy to DLL3+ Cancer Cells An anti-DLL3 CAR is made as described in Example 20. This CAR construct is engineered into T-cells also as described in Example 20.

Two payload cassettes are made for delivery by the anti-DLL3 CAR T-cell. First, a construct is made that encodes CXCL9 as a secreted payload operably linked to an RDE with an early expression profile (early maximal expression after activation of the cell) such as AU2 (CSF-2, maximal fold induction on day 1), AU101 (IFNg, maximal fold induction on day 1), or AU5 (EDN1, maximal fold induction on day 3/4). Second, a construct is made that encodes an anti-PD1 antibody (e.g., Pembrolizumab (Keytruda®)) as a secreted payload operably linked to an RDE with a late expression profile (late maximal expression after activation of the cell) such as AU22 (SEM-A4D, maximal fold induction on day 8) or AU19 (TMEM-219, maximal fold induction on day 8). The two payloads can be placed into a bicistronic construct, placed on the same construct, or the payloads can be expressed from separate constructs. The payload construct(s) are engineered into the anti-DLL3 CAR T-cell as described above in Example 20.

When this engineered CAR T-cell is administered to NSG mouse model as described in Example 20. The CAR T-cells are activated by DLL3 at the tumor target, and the RDE constructs with the CXCL9 express this payload first, and then at a later time the anti-PD1 antibody payload is expressed. The AU2, AU5 or AU101 RDE of the CXCL9 construct has an early maximal expression of about 1 day after activation of the cell by DLL3 at a cancer target. The CXCL9 can be secreted early after activation of the T-cell by DLL3 and the CXCL9 can potentiate the T-cell responses to tumors treated with anti-PD1 antibodies. After CXCL9 secretion, anti-PD1 is maximally secreted at a later time (about 8 days) and the effect of this antibody can be increased by the pretreatment with CXCL9.

The early expression of CXCL9 potentiates the activity and cancer killing from the anti-PD1 antibody.

Example 24: Combination Therapy

CAR constructs are made using an anti-DLL3 antibody domain such as described in US20170137533 (which is incorporated by reference in its entirety for all purposes) as SC16.15 or SC16.25. This anti-DLL3 antibody domain is made into a single chain antibody (scFv), and the anti-DLL3 scFv is combined with the transmembrane and intracellular portions of a CAR (such as those described in WO 2012/079000, which is hereby incorporated-by-reference in its entirety for all purposes) to make an anti-DLL3 CAR.

Payload constructs are made by engineering a transgene with an RDE so that when the transgene is transcribed the transcript for the transgene operably links the transgene to the RDE. The payload transgene can encode an anti-4-1BB antibody, an anti-CD11b antibody, an anti-CTLA4 antibody, an anti-IL1b antibody, a BiTE, a CCL2, an anti-CXCR4 antibody, an anti-CXCL12 antibody, a HAC, a heparinase, a hyaluronidase, a Hsp60, a Hsp70, an IL-2, an IL-12, an IL-15, an IL-18, an INFγ, a miRNA (e.g., mir155), a CD40 ligand, an ApoE3, an ApoE4, an antagonists of CSF1 receptor, a TNFα, and/or an anti-CD28 antibody. The RDE can be AU101 (INFg) or AU14 (IL-6).

The constructs are transduced into primary T-cells which are then allowed to return to a resting state. This produced anti-DLL3 CAR T-cells with one or more of the payloads: anti-CXCL12 antibody, anti-CXCR4 antibody, IL-12, anti-4-1BB antibody, anti-CD11b antibody, anti-CTLA4 antibody, anti-ILlb antibody, a BiTE, CCL2, HAC, heparinase, hyaluronidase, Hsp60, Hsp70, IL-2, IL-15, IL-18, INFγ, miRNA (e.g., mir155), CD40 ligand, ApoE3, ApoE4, TNFα, CCR2, CCR4/CXCL12, CXCR3+CXCL9, CXCL9, ACLY, antagonists of CSF1 receptor, miRNA for Tox (e.g., hsa-mir-26b-5p (MIRT030248) hsa-mir-223-3p (MIRT054680)), miRNA for TCF-7 (e.g., mIR-192, mIR-34a, miR-133a, miR-138-5p, miR-342-5p, miR-491-5p, miR-541-3p), and/or anti-CD28 antibody (including full length and fragments such as single chain antibodies).

An antibody drug conjugate (ADC) is made between an anti-DLL3 antibody such as described in US20170137533 (which is incorporated by reference in its entirety for all purposes) as SC16.15 or SC16.25. This anti-DLL3 antibody domain is converted to an appropriate format (e.g., a Fab, F(ab')2 or full-length IgG) and conjugated to one or more drugs (e.g., etoposide, irinotecan, cisplatin and/or carboplatin).

An NSG mouse model from Jackson Laboratories is used to establish cancer xenografts of human melanoma, human small cell lung cancer (SCLC), and human IDH1mut glioma. After the cancer xenograft is established in the mice, the mice are treated with the primary T-cells with the anti-DLL3 CAR and one of the payloads, anti-DLL3 ADC, or primary T-cells with the anti-DLL3 CAR and one of the payloads and the anti-DLL3 ADC. Cancer xenograft killing is then compared between the ADC, different payloads of the DLL3-CAR T-cells, and the different payloads of the DLL3 CAR T-cells with the anti-DLL3 ADC.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a patient, comprising the steps of: obtaining the patient wherein the patient has a prostate cancer positive for a TnMUC1, a triple negative, breast cancer positive for a TnMUC1 or a pancreatic cancer positive for a TnMUC1;

administering to the patient a therapeutically effective amount of a primary T-cell comprising an anti-TnMUC1 chimeric antigen receptor, and a heterologous nucleic acid comprising a polynucleotide encoding an IL-12 that is operably linked to a polynucleotide encoding a RNA degradation element (RDE), wherein the RDE is an AU rich element; transcribing the heterologous nucleic acid to make a transcript encoding the transgene operably linked to the RDE; binding the anti-TnMUC1 chimeric antigen receptor to the TnMUC1 on the prostate cancer, the breast cancer or the pancreatic cancer, whereby the primary T-cell is activated and the amount of IL-12 made from the polynucleotide is increased, and killing cells of the prostate cancer, the triple negative, breast cancer or the pancreatic cancer.

2. The method of claim 1, wherein the patient has a breast cancer positive for a TnMUC 1.

3. The method of claim 2, wherein the RNA degradation element is from a 3'-UTR of IFNg or a 3'-UTR of IL-6.

4. The method of claim 3, wherein the RNA degradation element is from a 3'-UTR of IFNg.

5. The method of claim 4, further comprising administering a second anti-cancer therapy.

6. The method of claim 5, wherein the second anti-cancer therapy is a chemotherapeutic, an antibody, an antibody-drug conjugate, a radiotherapy, an alkylating agent, a plant alkaloid, an antitumor antibiotic, an antimetabolite, a topoisomerase inhibitor, or an anti-neoplastic.

7. The method of claim 1, wherein the patient has a pancreatic cancer positive for a TnMUC 1.

8. The method of claim 7, wherein the RNA degradation element is from a 3'-UTR of IFNg or a 3'-UTR of IL-6.

9. The method of claim 8, wherein the RNA degradation element is from a 3'-UTR of IFNg.

10. The method of claim 9, further comprising administering a second anti-cancer therapy.

11. The method of claim 10, wherein the second anti-cancer therapy is a chemotherapeutic.

12. The method of claim 11, wherein the chemotherapeutic is a fluorouracil, a leucovorin, an irinotecan, an oxaliplatin, a gemcitabine or a paclitaxel.

13. The method of claim 1, wherein the RNA degradation element is from a 3'-UTR of IFNg or a 3'-UTR of IL-6.

14. The method of claim 1, further comprising administering a second anti-cancer therapy.

15. The method of claim 14, wherein the second anti-cancer therapy is a chemotherapeutic, an antibody, an antibody-drug conjugate, a radiotherapy, an alkylating agent, a plant alkaloid, an antitumor antibiotic, an antimetabolite, a topoisomerase inhibitor, or an anti-neoplastic.

16. The method of claim 15, wherein the second anti-cancer therapy is a chemotherapeutic.

17. The method of claim 16, wherein the chemotherapeutic is a fluorouracil, a leucovorin, an irinotecan, an oxaliplatin, a gemcitabine or a paclitaxel.

18. The method claim 16, wherein the chemotherapeutic is an anthracycline, a taxane, or a capecitabine.

19. The method of claim 15, wherein the second anti-cancer therapy is a chemotherapeutic.

20. The method of claim 15, wherein the second anti-cancer therapy is a chemotherapeutic.

* * * * *

SEQUENCE LISTING

```
<160> NUMBER OF SEQ ID NOS: 25

<210> SEQ ID NO 1
<211> LENGTH: 5
<212> TYPE: RNA
<213> ORGANISM: Artificial Sequence
<220> FEATURE:
<223> OTHER INFORMATION: AU repeat element

<400> SEQUENCE: 1 auuua                                                                    5

<210> SEQ ID NO 2
<211> LENGTH: 13
<212> TYPE: RNA
<213> ORGANISM: Artificial Sequence
<220> FEATURE:
<223> OTHER INFORMATION: AU rich element

<400> SEQUENCE: 2
auuuauuuau uua                                                          13

<210> SEQ ID NO 3
<211> LENGTH: 5
<212> TYPE: RNA
<213> ORGANISM: Artificial Sequence
<220> FEATURE:
<223> OTHER INFORMATION: GU rich repeat element

<400> SEQUENCE: 3 uuguu                                                                    5

<210> SEQ ID NO 4
<211> LENGTH: 7
<212> TYPE: RNA
<213> ORGANISM: Artificial Sequence
<220> FEATURE:
<223> OTHER INFORMATION: GU rich repeat element

<400> SEQUENCE: 4 ugggau                                                                   7

<210> SEQ ID NO 5
<211> LENGTH: 5
<212> TYPE: RNA
<213> ORGANISM: Artificial Sequence
<220> FEATURE:
<223> OTHER INFORMATION: U rich repeat element

<400> SEQUENCE: 5 guuug                                                                    5
```

```
<210> SEQ ID NO 6
<211> LENGTH: 7
<212> TYPE: RNA
<213> ORGANISM: Artificial Sequence
<220> FEATURE:
<223> OTHER INFORMATION: GU rich element

<400> SEQUENCE: 6 uuuguuu                                                                  7

<210> SEQ ID NO 7
<211> LENGTH: 9
<212> TYPE: RNA
<213> ORGANISM: Artificial Sequence
<220> FEATURE:
<223> OTHER INFORMATION: U rich element
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (5)..(6)
<223> OTHER INFORMATION: n is a, c, g, or u

<400> SEQUENCE: 7 nnuunnuuu                                                                9

<210> SEQ ID NO 8
<211> LENGTH: 7
<212> TYPE: RNA
<213> ORGANISM: Artificial Sequence
<220> FEATURE:
<223> OTHER INFORMATION: U rich element

<400> SEQUENCE: 8 uuuauuu                                                                  7

<210> SEQ ID NO 9
<211> LENGTH: 7
<212> TYPE: RNA
<213> ORGANISM: Artificial Sequence
<220> FEATURE:
<223> OTHER INFORMATION: U rich element

<400> SEQUENCE: 9 uuuuuuu                                                                  7

<210> SEQ ID NO 10
<211> LENGTH: 5
<212> TYPE: RNA
<213> ORGANISM: Artificial Sequence
<220> FEATURE:
<223> OTHER INFORMATION: RDE element

<400> SEQUENCE: 10 uuaga                                                                    5

<210> SEQ ID NO 11
<211> LENGTH: 5
<212> TYPE: RNA
<213> ORGANISM: Artificial Sequence
<220> FEATURE:
<223> OTHER INFORMATION: RDE element

<400> SEQUENCE: 11
```

```
aguuu                                                            5

<210> SEQ ID NO 12
<211> LENGTH: 9
<212> TYPE: RNA
<213> ORGANISM: Artificial Sequence
<220> FEATURE:
<223> OTHER INFORMATION: RDE element

<400> SEQUENCE: 12 uuauuuauu                                                        9

<210> SEQ ID NO 13
<211> LENGTH: 4
<212> TYPE: RNA
<213> ORGANISM: Artificial Sequence
<220> FEATURE:
<223> OTHER INFORMATION: RDE element

<400> SEQUENCE: 13 uuga                                                             4

<210> SEQ ID NO 14
<211> LENGTH: 7
<212> TYPE: RNA
<213> ORGANISM: Artificial Sequence
<220> FEATURE:
<223> OTHER INFORMATION: RDE element

<400> SEQUENCE: 14 ugggggau                                                         7

<210> SEQ ID NO 15
<211> LENGTH: 9
<212> TYPE: RNA
<213> ORGANISM: Artificial Sequence
<220> FEATURE:
<223> OTHER INFORMATION: RDE element

<400> SEQUENCE: 15 cugcugcug                                                        9

<210> SEQ ID NO 16
<211> LENGTH: 5
<212> TYPE: RNA
<213> ORGANISM: Artificial Sequence
<220> FEATURE:
<223> OTHER INFORMATION: RDE element

<400> SEQUENCE: 16 auuga                                                            5

<210> SEQ ID NO 17
<211> LENGTH: 18
<212> TYPE: PRT
<213> ORGANISM: Thoseaasigna virus 2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 19
<212> TYPE: PRT
```

<213> ORGANISM: Porcine teschovirus-1

<400> SEQUENCE: 18

Ala Thr Asn Phe Ser Leu Leu Lys Gln Ala Gly Asp Val Glu Glu Asn
1 5 10 15

Pro Gly Pro

<210> SEQ ID NO 19
<211> LENGTH: 20
<212> TYPE: PRT
<213> ORGANISM: Equine rhinitis A virus

<400> SEQUENCE: 19

Gln Cys Thr Asn Tyr Ala Leu Leu Lys Leu Ala Gly Asp Val Glu Ser
1 5 10 15

Asn Pro Gly Pro
20

<210> SEQ ID NO 20
<211> LENGTH: 22
<212> TYPE: PRT
<213> ORGANISM: foot and mouth disease virus

<400> SEQUENCE: 20

Val Lys Gln Thr Leu Asn Phe Asp Leu Leu Lys Leu Ala Gly Asp Val
1 5 10 15

Glu Ser Asn Pro Gly Pro
20

<210> SEQ ID NO 21
<211> LENGTH: 282
<212> TYPE: DNA
<213> ORGANISM: Homo sapiens

<400> SEQUENCE: 21
taattaagtg cttcccactt aaaacatatc aggccttcta tttatttaaa tatttaaatt 60
ttatatttat tgttgaatgt atggtttgct acctattgta actattattc ttaatcttaa 120
aactataaat atggatcttt tatgattctt tttgtaagcc ctaggggctc taaaatggtt 180
tcacttattt atcccaaaat atttattatt atgttgaatg ttaaatatag tatctatgta 240
gattggttag taaaactatt taataaattt gataaatata aa 282

<210> SEQ ID NO 22
<211> LENGTH: 282
<212> TYPE: DNA
<213> ORGANISM: Homo sapiens

<400> SEQUENCE: 22
taattaagtg cttcccactt aaaacatatc aggccttcta tttatttaaa tatttaaatt 60
ttatatttat tgttgaatgt atggtttgct acctattgta actattattc ttaatcttaa 120
aactataaat atggatcttt tatgattgaa tttgtaagcc ctaggggctc taaaatggtt 180
tcacttattt atcccaaaat atttattatt atgttgaatg ttaaatatag tatctatgta 240
gattggttag taaaactatt taataaattt gataaatata aa 282

<210> SEQ ID NO 23
<211> LENGTH: 585
<212> TYPE: DNA
<213> ORGANISM: Homo sapiens

```
<400> SEQUENCE: 23
tggttgtcct gcctgcaata tttgaatttt aaatctaaat ctatttatta atatttaaca        60
ttatttatat ggggaatata tttttagact catcaatcaa ataagtattt ataatagcaa       120
cttttgtgta atgaaaatga atatctatta atatatgtat tatttataat tcctatatcc       180
tgtgactgtc tcacttaatc ctttgttttc tgactaatta ggcaaggcta tgtgattaca       240
aggctttatc tcaggggcca actaggcagc caacctaagc aagatcccat gggttgtgtg       300
tttatttcac ttgatgatac aatgaacact tataagtgaa gtgatactat ccagttactg       360
ccggtttgaa aatatgcctg caatctgagc cagtgcttta atggcatgtc agacagaact       420
tgaatgtgtc aggtgaccct gatgaaaaca tagcatctca ggagatttca tgcctggtgc       480
ttccaaatat tgttgacaac tgtgactgta cccaaatgga aagtaactca tttgttaaaa       540
ttatcaatat ctaatatata tgaataaagt gtaagttcac aacta                      585

<210> SEQ ID NO 24
<211> LENGTH: 32
<212> TYPE: DNA
<213> ORGANISM: Artificial Sequence
<220> FEATURE:
<223> OTHER INFORMATION: MinP promoter

<400> SEQUENCE: 24
tagagggtat ataatggaag ctcgacttcc ag                                      32

<210> SEQ ID NO 25
<211> LENGTH: 131
<212> TYPE: DNA
<213> ORGANISM: Artificial Sequence
<220> FEATURE:
<223> OTHER INFORMATION: NFAT promoter

<400> SEQUENCE: 25
ggaggaaaaa ctgtttcata cagaaggcgt ggaggaaaaa ctgtttcata cagaaggcgt        60
ggaggaaaaa ctgtttcata cagaaggcgt agatctagac tctagagggt atataatgga       120
agctcgaatt c                                                           131
```